United States Patent
Shapiro et al.

(10) Patent No.: US 11,584,718 B2
(45) Date of Patent: *Feb. 21, 2023

(54) ACTIVATORS OF THE UNFOLDED PROTEIN RESPONSE

(71) Applicant: The Board of Trustees of the University of Illinois, Urbana, IL (US)

(72) Inventors: David J. Shapiro, Urbana, IL (US); Paul J. Hergenrother, Champaign, IL (US); Matthew W. Boudreau, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/319,447

(22) Filed: May 13, 2021

(65) Prior Publication Data

US 2021/0340100 A1    Nov. 4, 2021

Related U.S. Application Data

(60) Division of application No. 16/801,839, filed on Feb. 26, 2020, now Pat. No. 11,046,647, which is a continuation of application No. PCT/US2019/040058, filed on Jul. 1, 2019.

(60) Provisional application No. 62/693,641, filed on Jul. 3, 2018.

(51) Int. Cl.
| | | |
|---|---|---|
| *C07D 209/34* | (2006.01) | |
| *A61P 35/00* | (2006.01) | |
| *A61K 9/00* | (2006.01) | |
| *A61K 45/06* | (2006.01) | |

(52) U.S. Cl.
CPC ............ *C07D 209/34* (2013.01); *A61P 35/00* (2018.01); *A61K 9/0019* (2013.01); *A61K 9/0053* (2013.01); *A61K 45/06* (2013.01)

(58) Field of Classification Search
CPC ........ C07D 209/34; A61P 35/00; A61K 45/06
See application file for complete search history.

(56) References Cited

U.S. PATENT DOCUMENTS

| | | |
|---|---|---|
| 8,268,879 B2 | 9/2012 | Halperin |
| 9,316,631 B1 | 4/2016 | Gupta |
| 9,708,247 B2 | 7/2017 | Walter |
| 11,046,647 B2 | 6/2021 | Shapiro |
| 2007/0299102 A1 | 12/2007 | Felding |
| 2010/0029646 A1 | 2/2010 | Christensen |
| 2010/0227863 A1 | 9/2010 | Christensen |
| 2014/0357661 A1 | 12/2014 | Bradbury |
| 2020/0190029 A1 | 6/2020 | Shapiro |

FOREIGN PATENT DOCUMENTS

| | | |
|---|---|---|
| CA | 2963784 A1 | 12/2008 |
| WO | 03078394 A1 | 9/2003 |
| WO | 2005030755 A1 | 4/2005 |
| WO | 2005097107 A2 | 10/2005 |
| WO | 2005097744 A1 | 10/2005 |
| WO | 2007041023 A1 | 4/2007 |
| WO | 2008024492 A2 | 2/2008 |
| WO | 2008024492 A3 | 5/2008 |
| WO | 2008071387 A1 | 6/2008 |
| WO | 2010109008 A1 | 9/2010 |
| WO | 2014047437 A1 | 3/2014 |
| WO | 2014113820 A1 | 7/2014 |
| WO | 2020009958 A1 | 1/2020 |

OTHER PUBLICATIONS

Andruska, N.D. et al. (2015). "Estrogen receptor a inhibitor activates the unfolded protein response, blocks protein synthesis, and induces tumor regression," PNAS, 112(15): 4737-4742.
Dhristensen et al., (2010). "Synthesis and Antitumor Effect in Vitro and in Vivo of Substituted 1,3-Dihydroindole-2-ones," J.Med. Chem., 53(19):7140-7145.
International Search Report and Written Opinion dated Oct. 28, 2019, for PCT/US2019/040058 filed on Jul. 1, 2019, 9 pages.
Livezey, M. et al. (2018). "Strong and sustained activation of the anticipatory unfolded protein response induces necrotic cell death," Cell Death & Differentiation, 25:1796-1807.
Mao et al., (2016). "Antiestrogen Resistant Cell Lines Expressing Estrogen Receptor a Mutations Upregulate the UnfoldedProtein Response and are Killed by BHPI," Sci Rep., 6:1-10.
PUBCHEM, (2008). Substance Record of SIDS 50779888, Available Date: Sep. 5, 2008, [retrieved on Oct. 2, 2019]: 4 pgs.
U.S. Appl. No. 17/254,771, filed Dec. 21, 2020, for Shapiro et al. (A U.S. Patent Application is not submitted herewith pursuant to the waiver of 37 C.F.R § 1 98(a)(2)(iii) issued by the Office on Sep. 21, 2004.).
Uddin et al., (2007). "Syntheses and Antiproliferative Evaluation of Oxyphenisatin Derivatives," Bioorg Med Chem Lett., 17(10):2854-2857.

*Primary Examiner* — Kamal A Saeed
(74) *Attorney, Agent, or Firm* — Haukaas Fortius PLLC; Michael H. Haukaas

(57) ABSTRACT

A set of small molecules ERα biomodulators that kill therapy-resistant ERα positive breast, ovarian, and endometrial cancer cells. These small molecules have increased therapeutic potential because of an increased ability to kill therapy-resistant breast cancer cells compared to BHPI and other conventional therapies (endocrine therapies, tamoxifen and fulvestrant/ICI). The new compounds do not only inhibit proliferation of the cancer cells but actually kills them, which prevents reactivation of tumors years later.

20 Claims, 50 Drawing Sheets

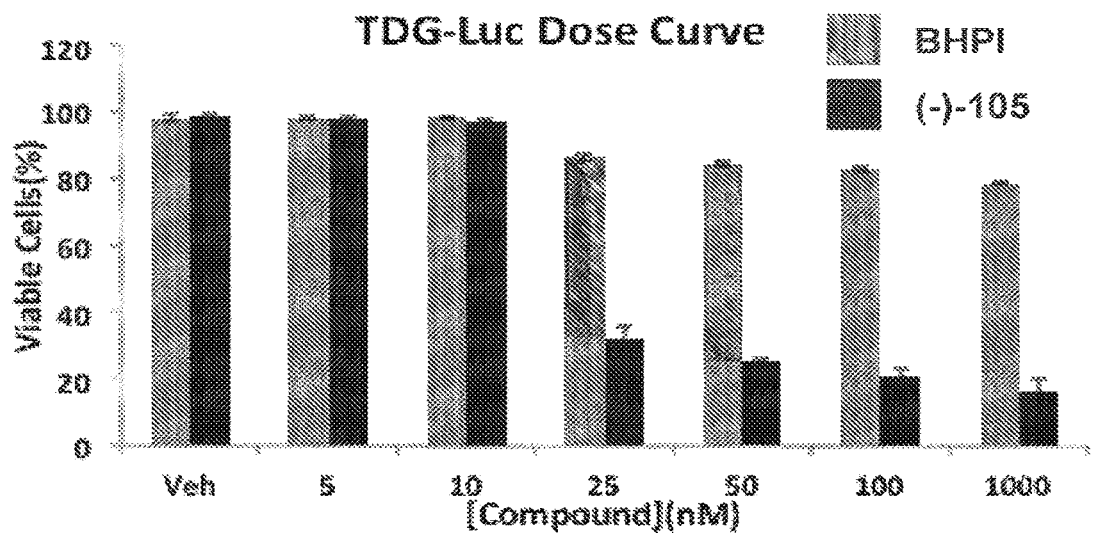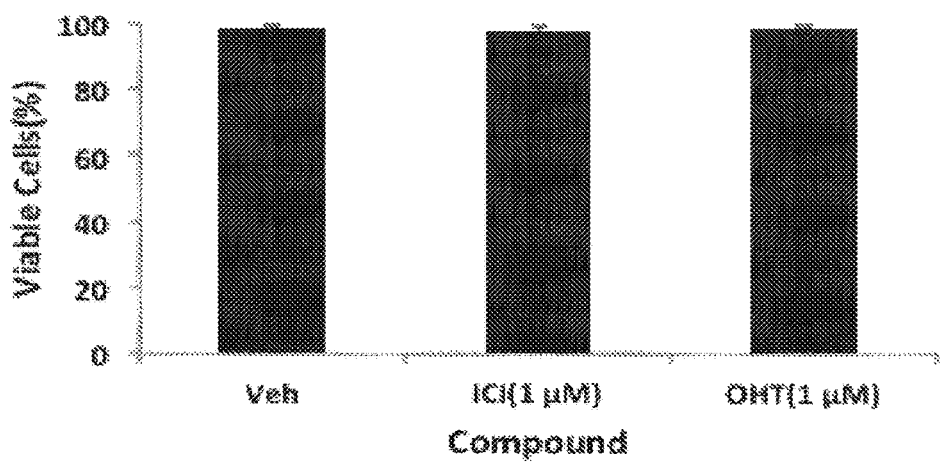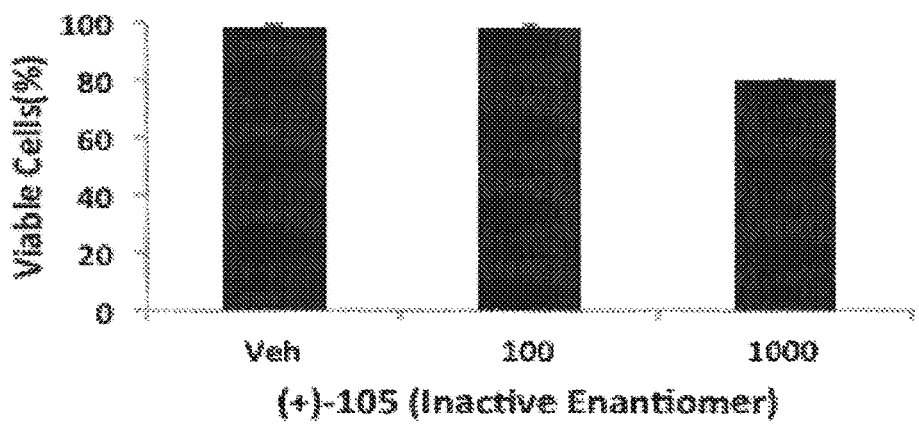
Fig. 13

Fig. 17

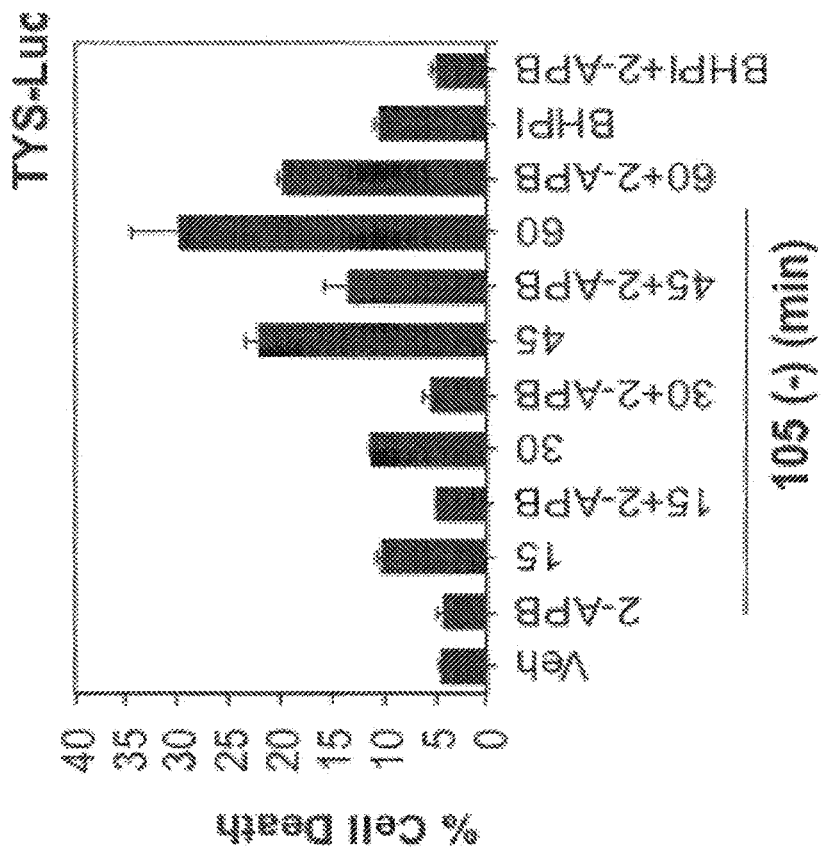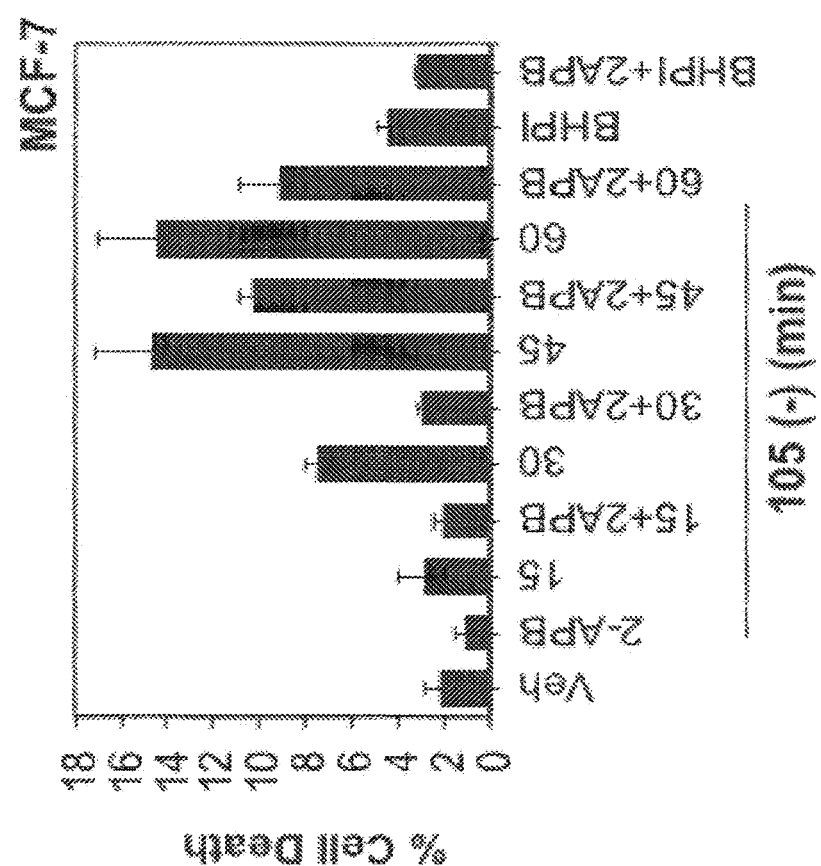
Fig. 21

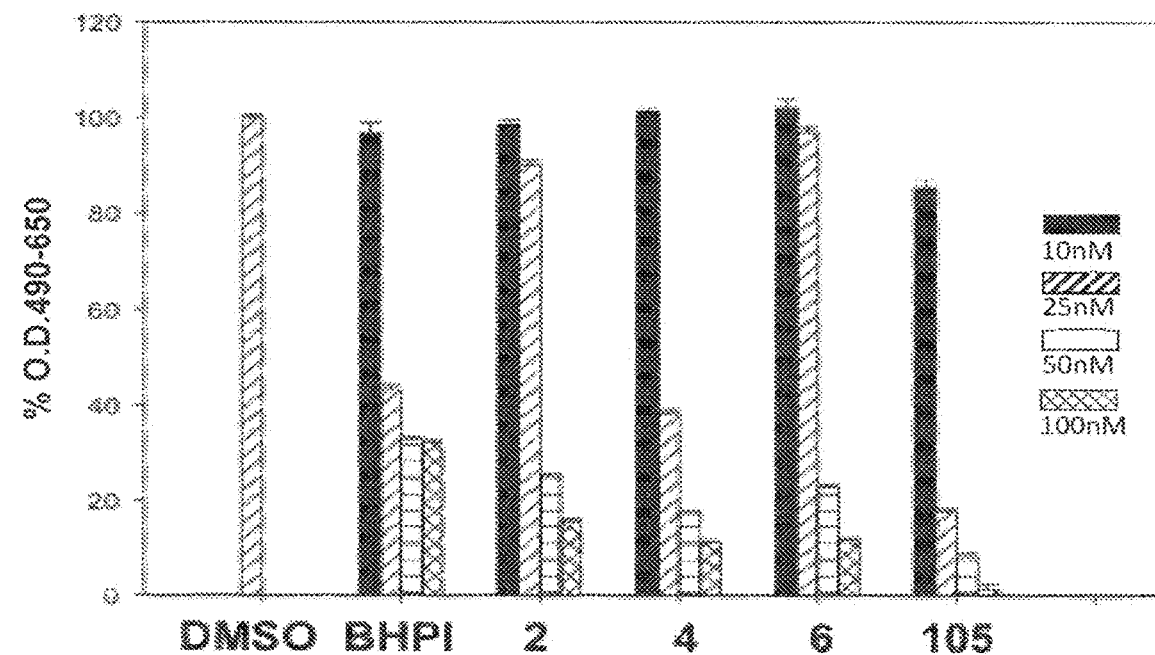
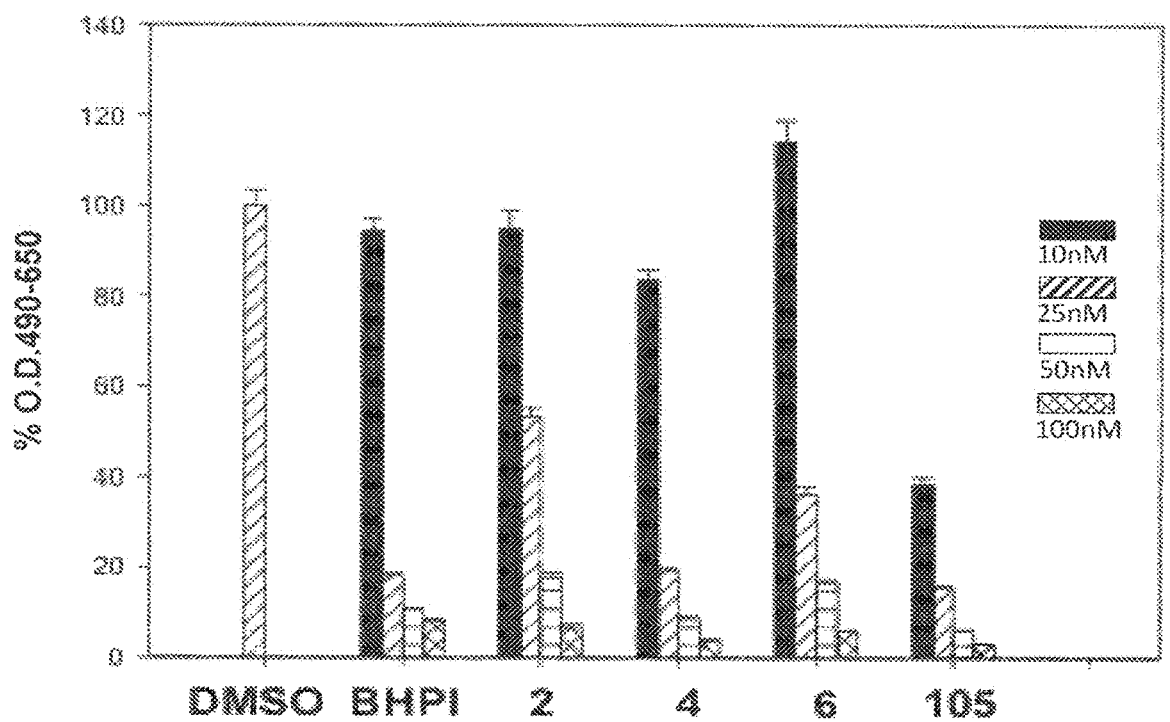
Fig. 30

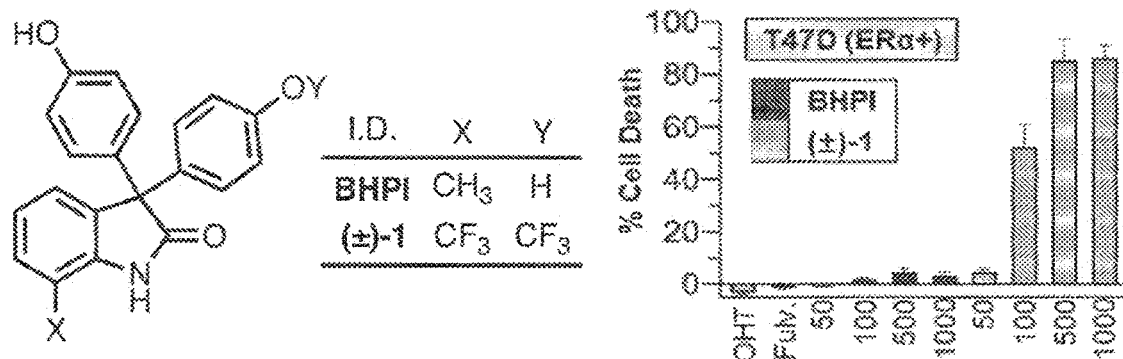
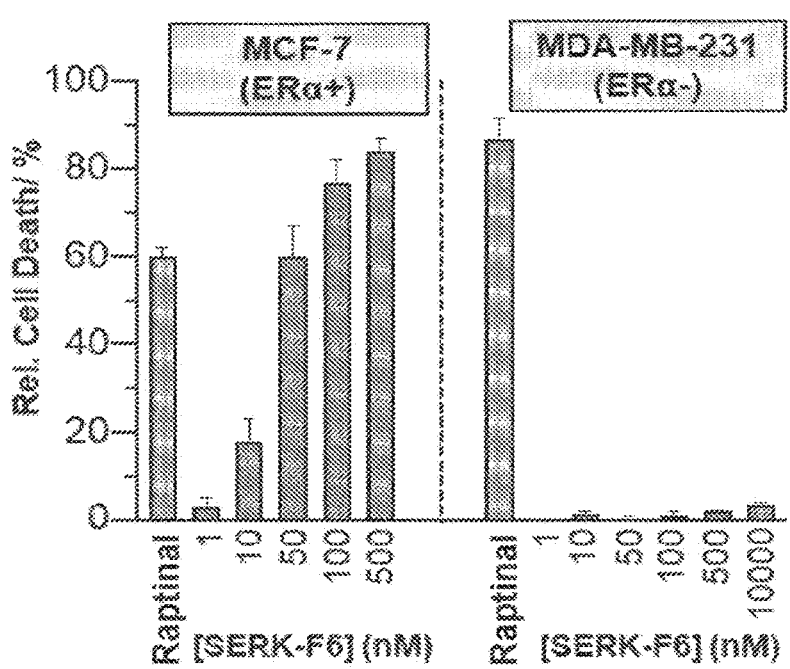
Fig. 36

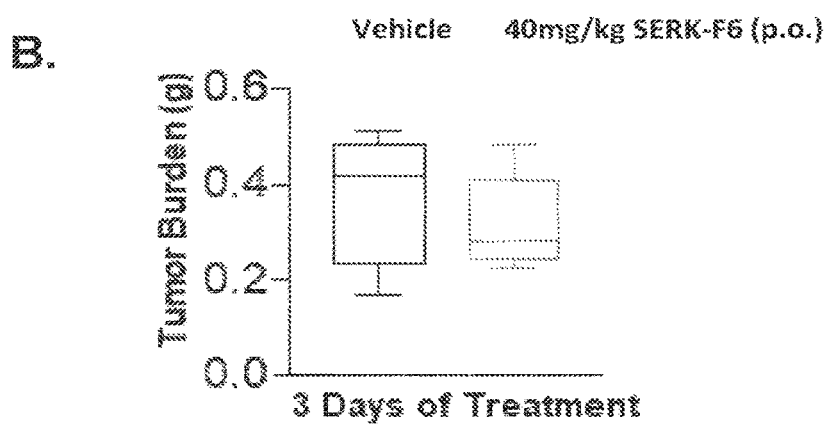
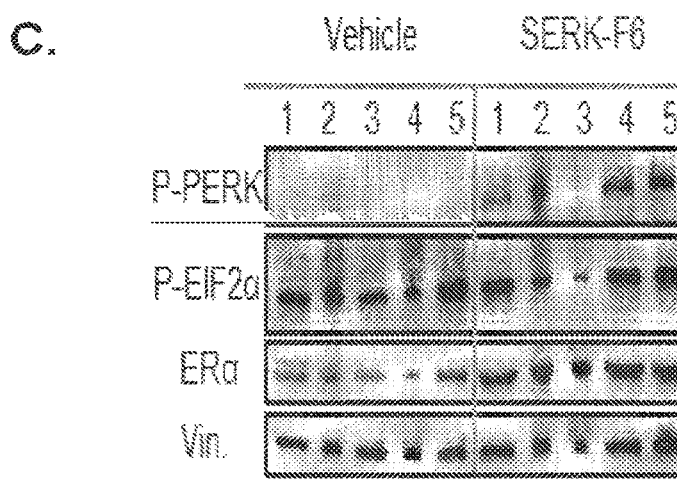
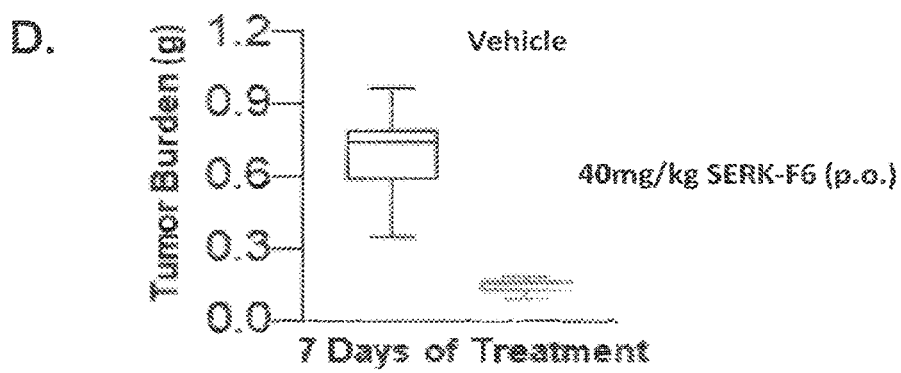
*Fig. 39 (cont.)*

B.
| Parameter | Units | Estimate |
|---|---|---|
| AUC | min*ng/mL | 137077.3 |
| $C_{max}$ | ng/mL | 197.104 |
| $T_{1/2}$ | min | 448 |
| $C_{max}$ | μM | 0.435 |
SERK-F6 40 mg/kg P.O.
| Parameter | Units | Estimate |
|---|---|---|
| AUC | min*ng/mL | 411548.4 |
| $C_{max}$ | ng/mL | 11956.7 |
| $T_{1/2}$ | min | 69.3 |
| $C_{max}$ | μM | 26.39 |
SERK-F6 20 mg/kg I.V.
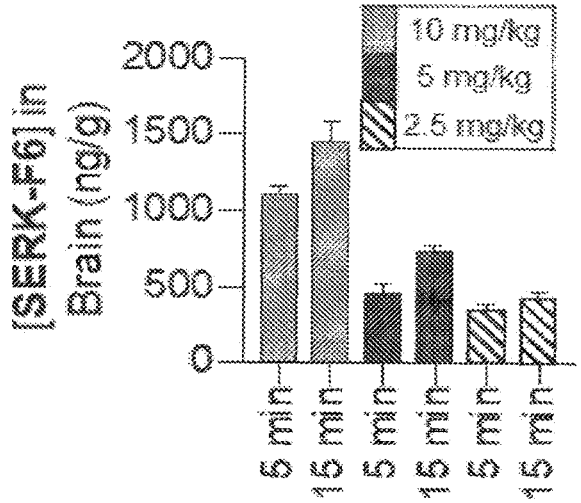
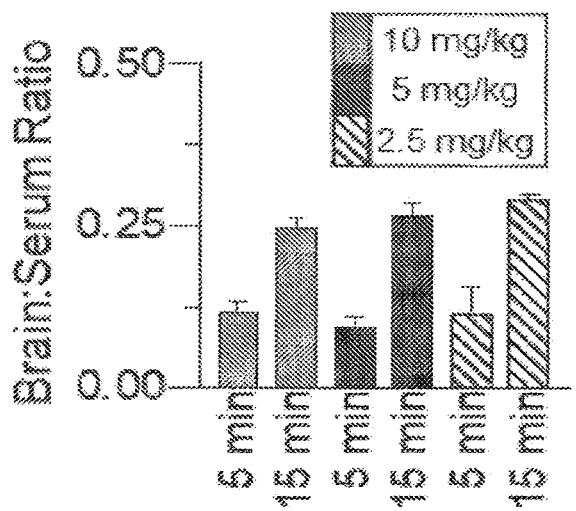
*Fig. 40 (cont.)*

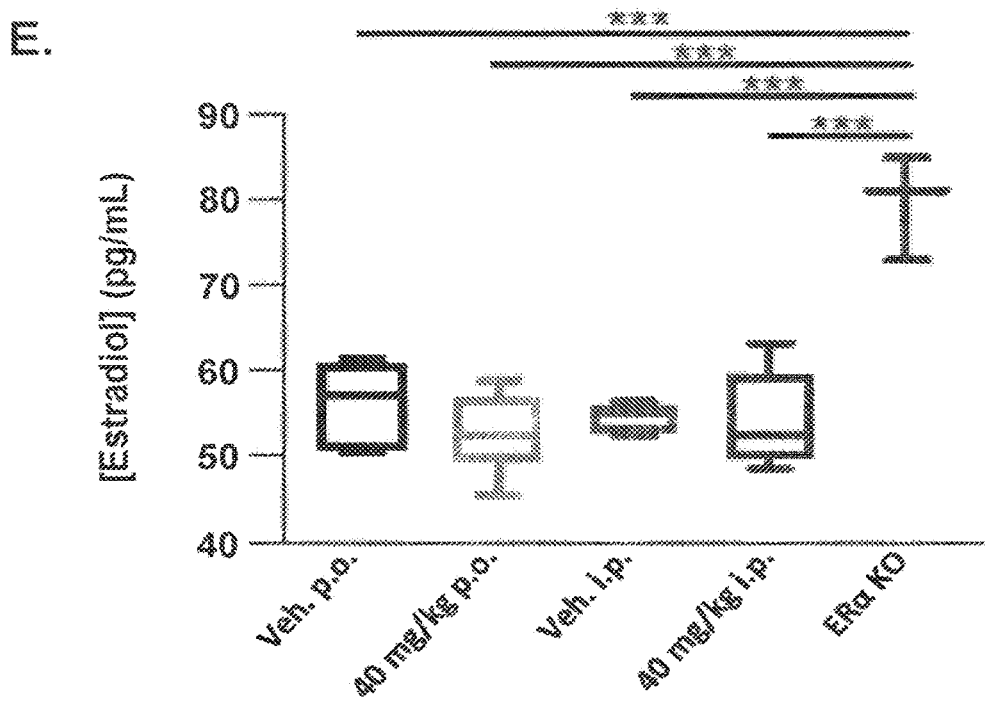
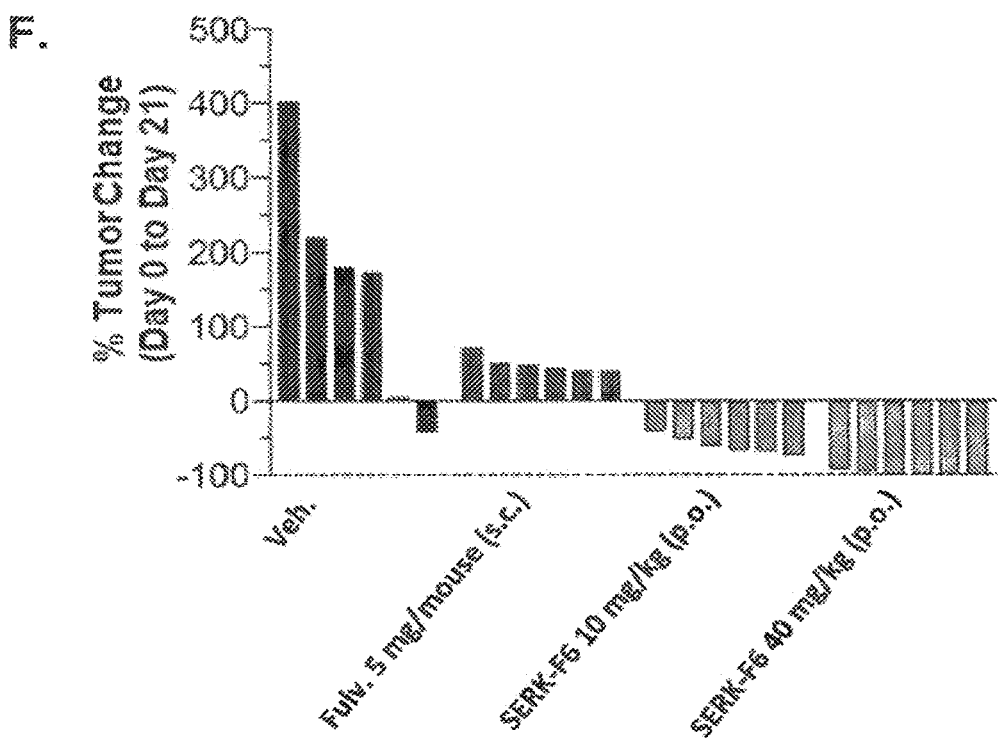
Fig. 40 (cont.)

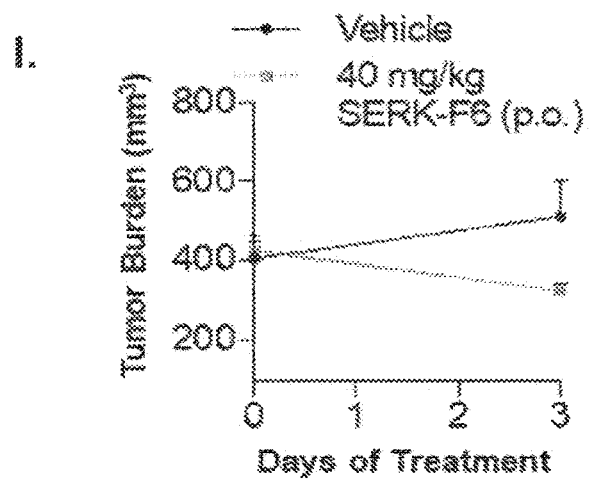
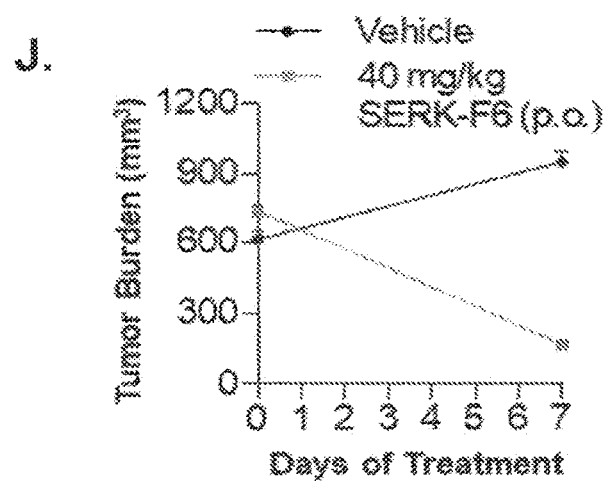
*Fig. 40 (cont.)*
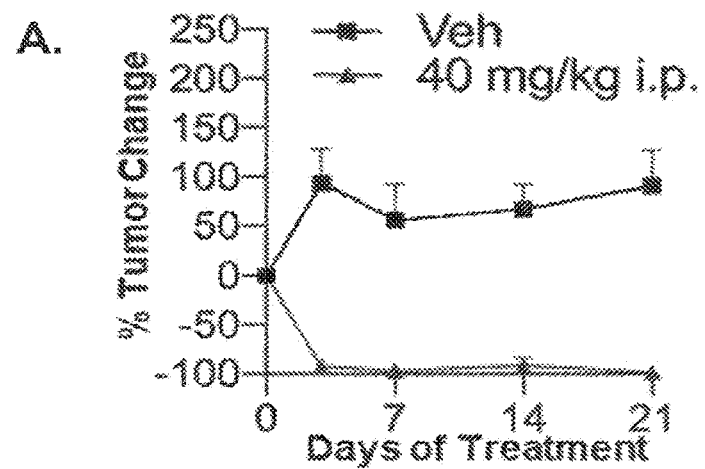
*Fig. 41*

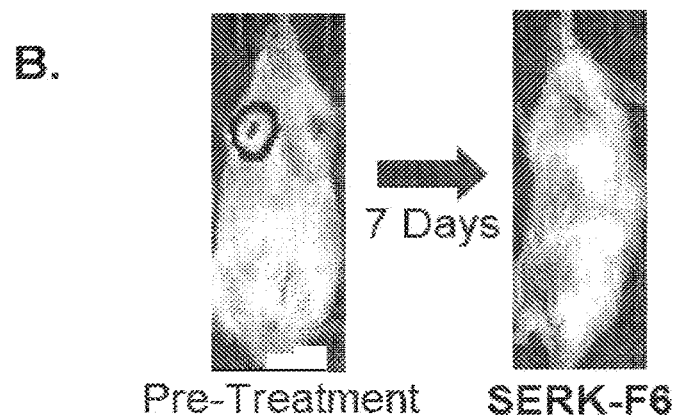
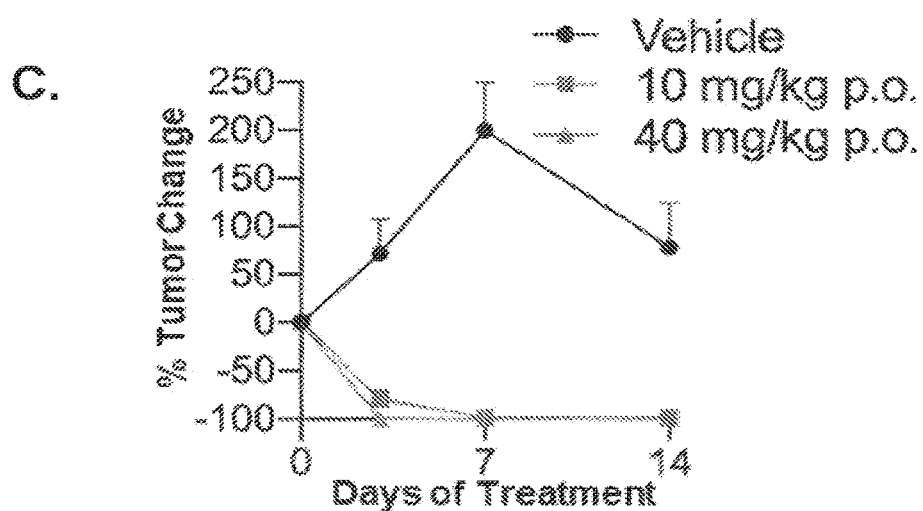
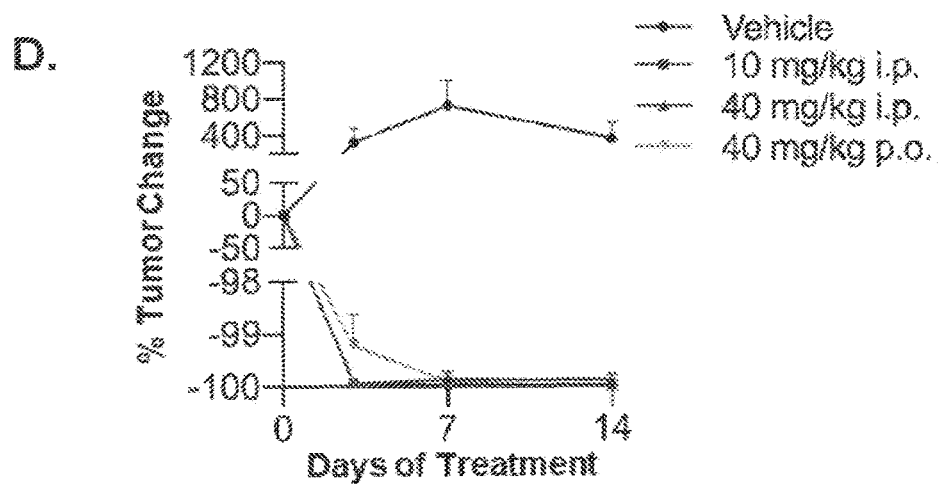
Fig. 41 (cont.)

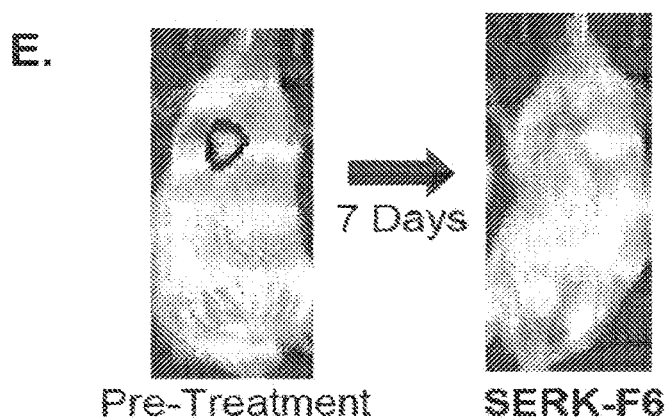
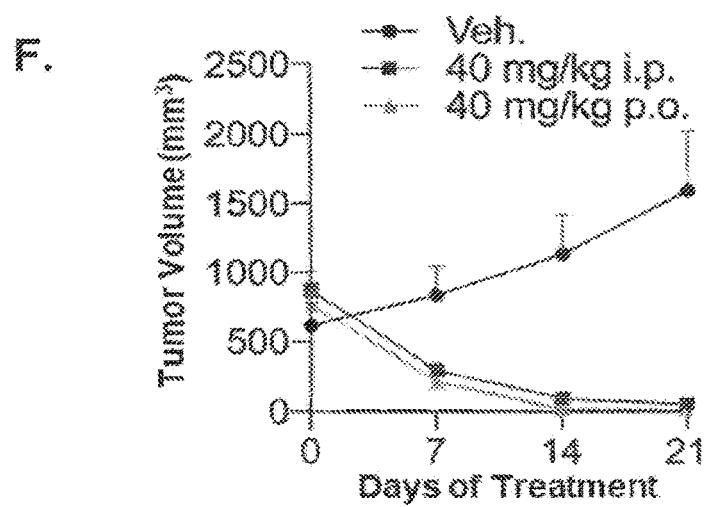
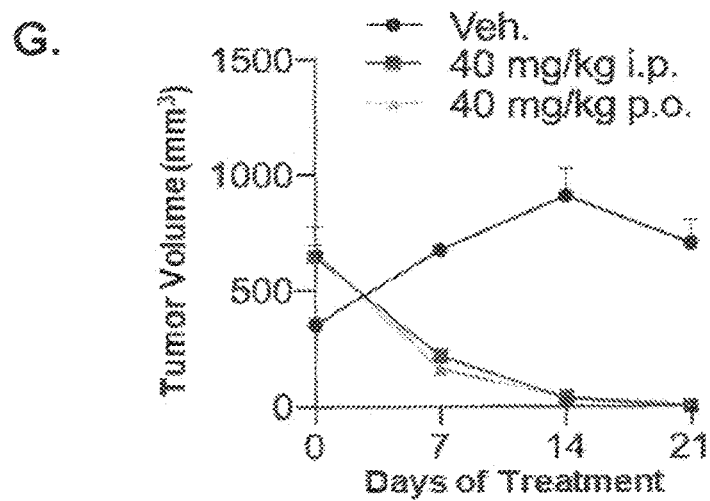
*Fig. 41 (cont.)*

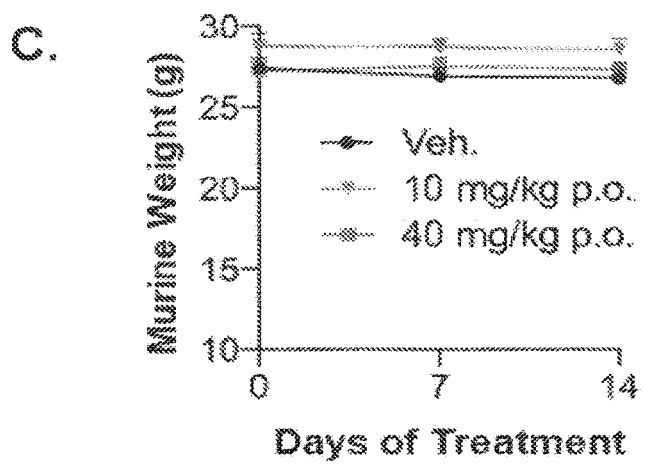
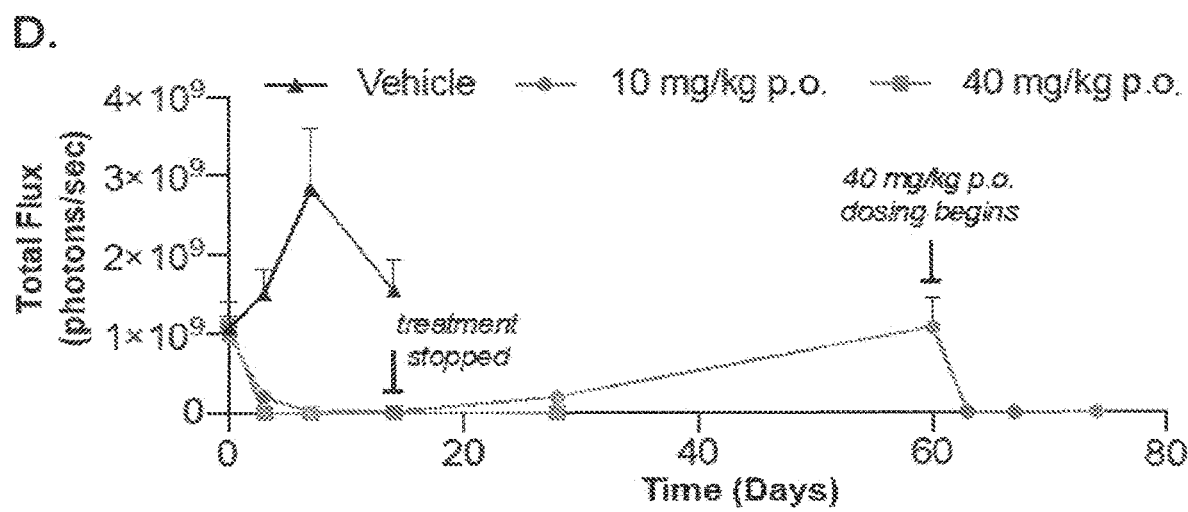
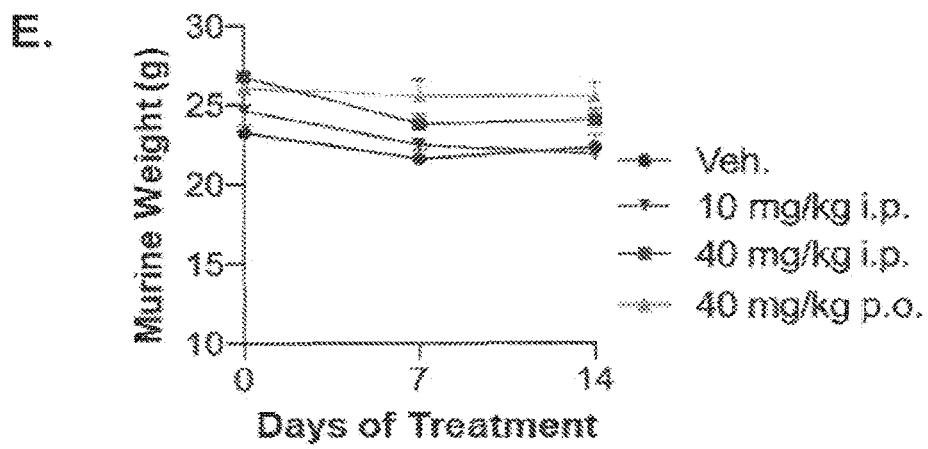
*Fig. 42 (cont.)*

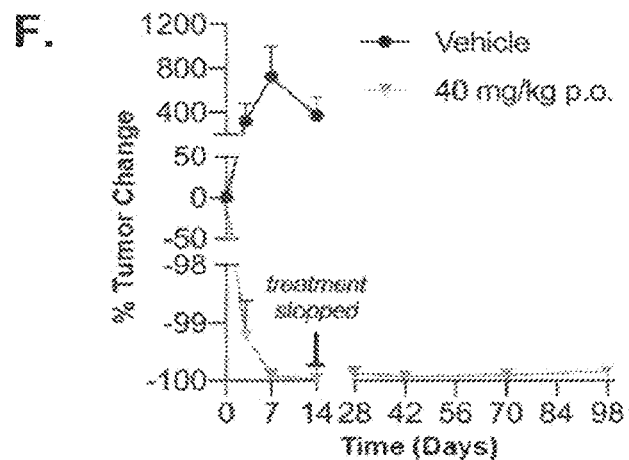
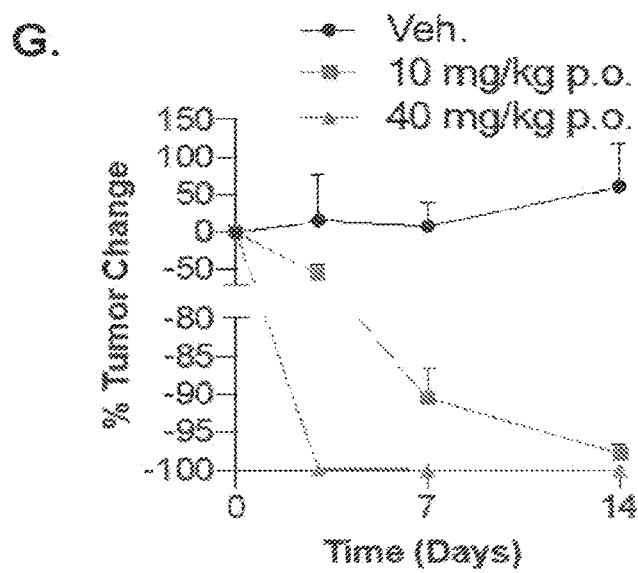
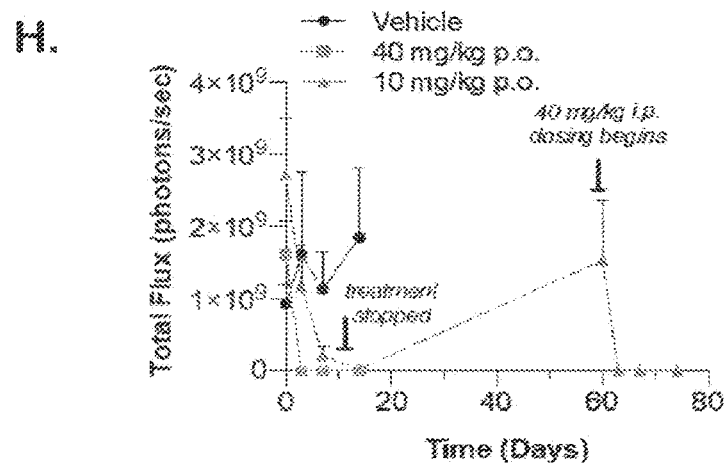
*Fig. 42 (cont.)*

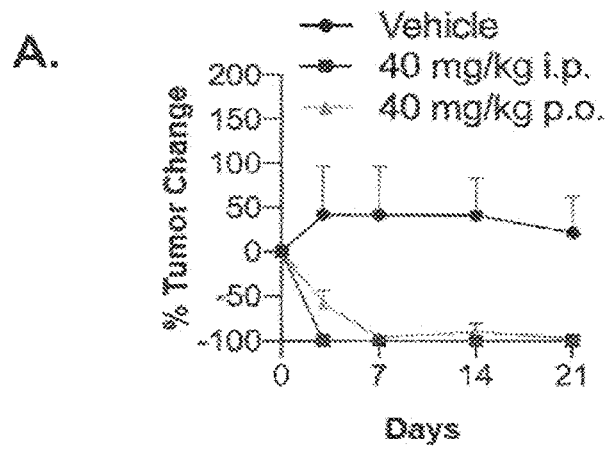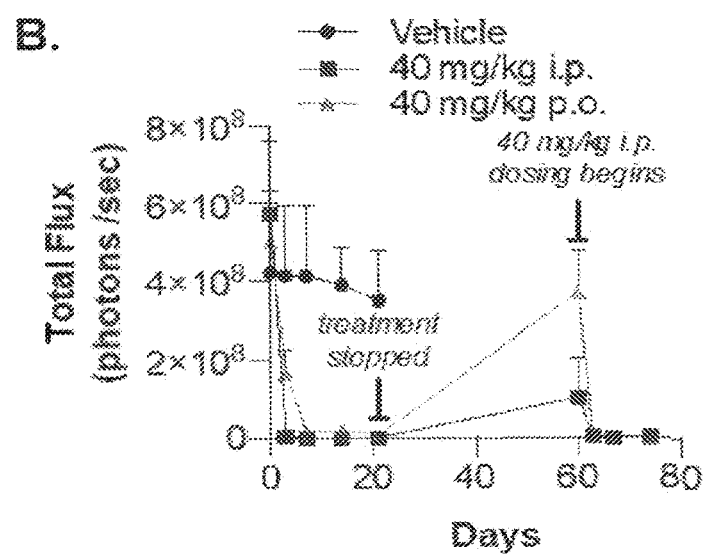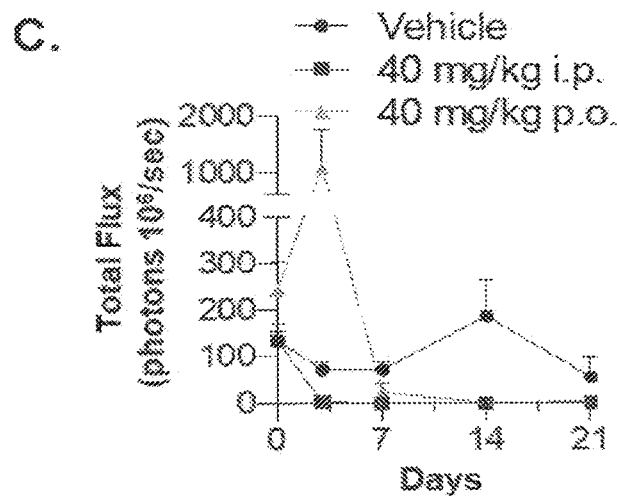
*Fig. 43*

ACTIVATORS OF THE UNFOLDED PROTEIN RESPONSE

RELATED APPLICATIONS

This application is a divisional of U.S. patent application Ser. No. 16/801,839, filed Feb. 26, 2020, which is a continuation under 35 U.S.C. 111(a) of International Application No. PCT/US2019/040058 filed Jul. 1, 2019, which claims priority under 35 U.S.C. § 119(e) to U.S. Provisional Patent Application No. 62/693,641, filed Jul. 3, 2018, which is incorporated herein by reference.

GOVERNMENT SUPPORT

This invention was made with government support under Grant No. RO1 DK071909 awarded by the National Institutes of Health and W81XWH-14-1-0159 awarded by the United States Army. The government has certain rights in the invention.

BACKGROUND OF THE INVENTION

Approximately 70% of breast cancers are ERα positive. Endocrine (hormonal) therapies for these tumors includes aromatase inhibitors that block estrogen production, tamoxifen which competes with estrogens for binding to ERα and fulvestrant/Faslodex/ICI 182,780, which both competes with estrogens and promotes ERα degradation. Although effective initially, resistance sometimes develops in primary tumors and is nearly universal in the metastatic setting. Although resistance mechanisms are diverse, recent studies show that approximately 30% of these metastatic tumors harbor ERα mutations, most commonly ERαD538G and ERαY537S. There is abundant evidence that these tumors exhibit estrogen-independent proliferation and are therefore resistant to aromatase inhibitors that block estrogen production. They are also largely resistant to tamoxifen and partially resistant to fulvestrant. Notably, patients whose metastatic tumors contain the ERαD538G mutation have a 6-month shorter survival time, and those with the ERαY537S mutation have a 12-month shorter survival time, than patients whose metastatic tumors contain non-mutated wild-type ERα. Therefore, efforts to develop chemotherapeutic agents targeting breast cancer cells containing these mutations are extensive and widespread.

The pathology of ERα positive breast cancer is unusual. While 5-year survival rates are impressive, the tumors often recur 10-20 years after initial diagnosis. This is thought to be due to reactivation of proliferation of dormant breast cancer cells. Thus, it is especially important to actually kill the tumor cells, and not allow them to remain dormant and susceptible to reactivation. Current endocrine therapies are cytostatic, not cytotoxic, and therefore do not kill residual breast cancer cells. This allows the cells to lie dormant and reactivate at a later date. Therapeutic options for these recurrent tumors are poor and most breast cancer deaths are in patients with ERα positive tumors.

Ovarian cancer usually presents at an advanced stage. Tumors often recur after surgery. Although 30-70% of ovarian tumors are ERα positive, and ERα expression is associated with a poor outcome, endocrine therapy is ineffective and recurrent tumors are usually treated with platinum-based chemotherapy and paclitaxel. Although initially responsive, after several cycles of treatment, tumors recur as resistant ovarian cancer, with poor therapeutic options. More than half of ovarian cancer patients die within 5 years. In ovarian cancer, a very common mechanism for resistance to paclitaxel and other chemotherapy agents is multidrug resistance; energy dependent drug efflux caused by overexpression of ATP-dependent efflux pumps, especially Multidrug Resistance Protein 1 (MDR1)/P-glycoprotein/ABCB1. Despite intensive efforts, effective non-toxic MDR1 inhibitors have remained elusive.

Although many cancers of the uterine endometrium are ERα positive, endocrine therapy works poorly.

Accordingly, an important therapeutic goal is therefore to identify new small molecules that are cytotoxic, not merely cytostatic, and to develop corresponding therapeutic methods.

SUMMARY

This disclosure provides the benefits of small molecules with an improved ability to actually kill therapy resistant breast cancer cells that have greatly increased therapeutic potential. Specifically, to prevent recurrence, it is critical to destroy the entire population of growing and dormant therapy resistant breast cancer cells. Compared to BHPI, and to the endocrine therapies tamoxifen and fulvestrant/ICI, the active enantiomer (-)C-105 has greatly increased ability to kill breast cancer cells. The compound (-)C-105 therefore shows dramatically increased therapeutic potential (FIG. 4A-4C).

This disclosure provides a compound of Formula I:

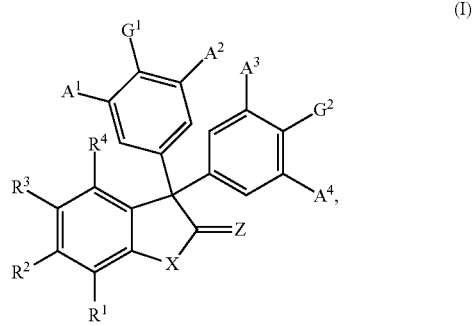

(I)

or a salt or solvate thereof;
wherein
$R^1$, $R^2$, $R^3$ and $R^4$ are each independently H, halo, —$OR^A$, —$SR^A$, —$N(R^A)_2$, alkyl, cycloalkyl, heterocyclyl, aryl, or heteroaryl;
$A^1$, $A^2$, $A^3$ and $A^4$ are each independently H, halo, or alkyl;
$G^1$ is halo, —$OR^B$, —$SR^B$, —$S(=O)_2R^B$, or alkyl;
$G^2$ is halo, —$OR^C$, —$SR^C$, —$S(=O)_2R^C$, or alkyl;
X and Z are each independently O, S, or —$NR^D$; and
$R^A$, $R^B$, $R^C$ and $R^D$ are each independently H or alkyl, wherein, when present, —$OR^B$ and —$OR^C$ are not both —OH;
wherein each alkyl, cycloalkyl, heterocyclyl, aryl, and heteroaryl is optionally substituted with one or more substituents.

The above compound can bind to the alpha estrogen receptor (ERα) and kill or inhibit the growth of cancer cells by hyperactivation of the unfolded protein response (UPR) in the endoplasmic reticulum.

Additionally, this disclosure provides a method of treating a cancer comprising administering to an ERα positive cancer subject in need thereof a therapeutically effective amount of the compound above, thereby treating the cancer in the subject.

The invention provides novel compounds of Formulas I-IV, intermediates for the synthesis of compounds of Formulas I-IV, as well as methods of preparing compounds of Formulas I-IV. The invention also provides compounds of Formulas I-IV that are useful as intermediates for the synthesis of other useful compounds. The invention provides for the use of compounds of Formulas I-IV for the manufacture of medicaments useful for the treatment of cancer in a mammal, such as a human.

The invention provides for the use of the compositions described herein for use in medical therapy. The medical therapy can be treating cancer, for example, breast cancer, ovarian cancer, uterine cancer, cervical carcinoma, endometrial cancer, lung cancer, pancreatic cancer, prostate cancer, or colon cancer. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 13. Dose response study shows (−)-105 is superior to BHPI and current endocrine therapies in killing TDG-Luc cells.

FIG. 17. Bioluminescent imaging (BLI) using luciferase shows near eradication of therapy-resistant TYS-luc breast tumors in mice.

FIG. 21. Blocking the efflux of calcium from the endoplasmic reticulum with 2-APB inhibits (−)-105-induced cancer cell death.

Figure 37:
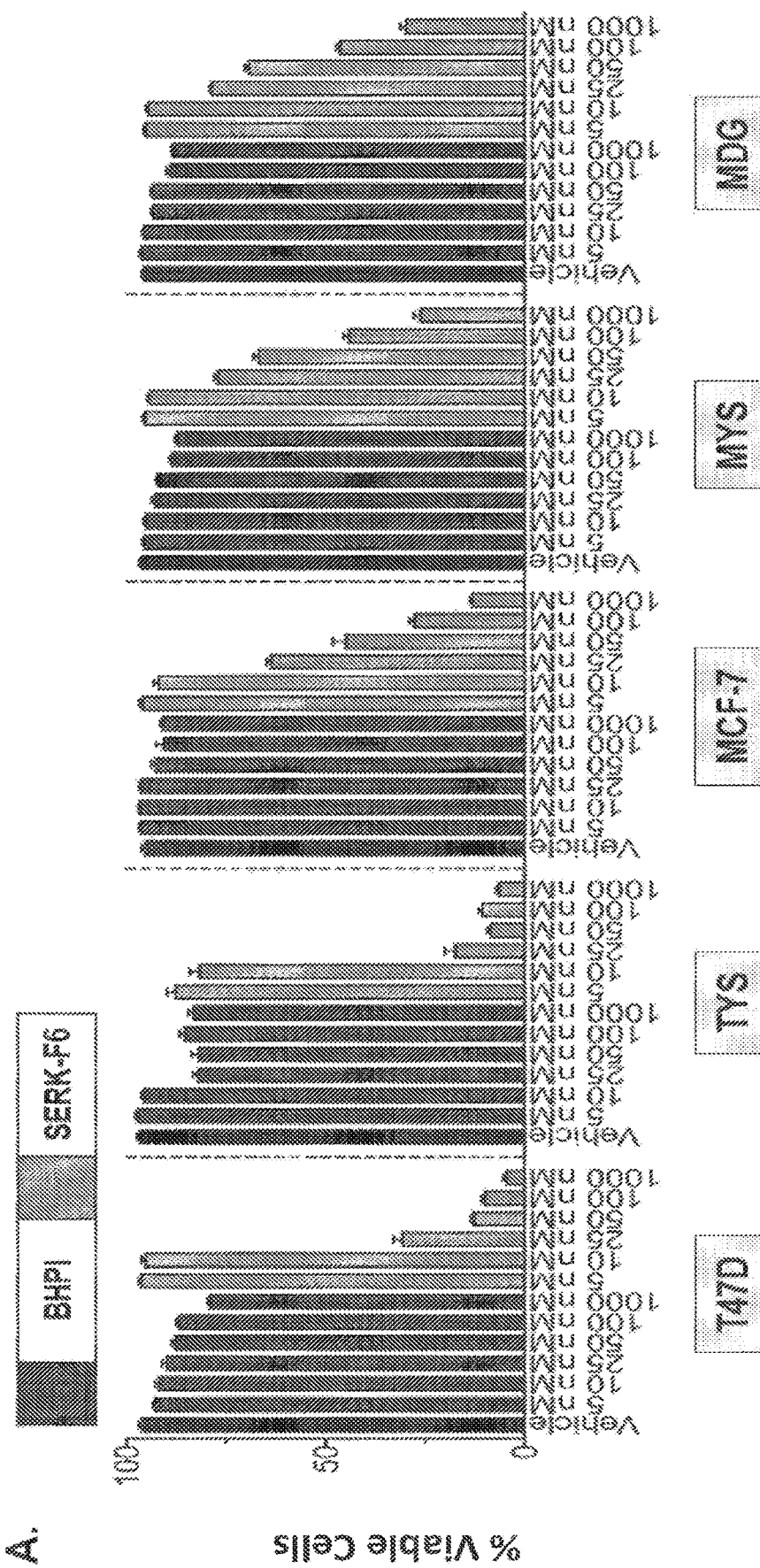
Figure 37:
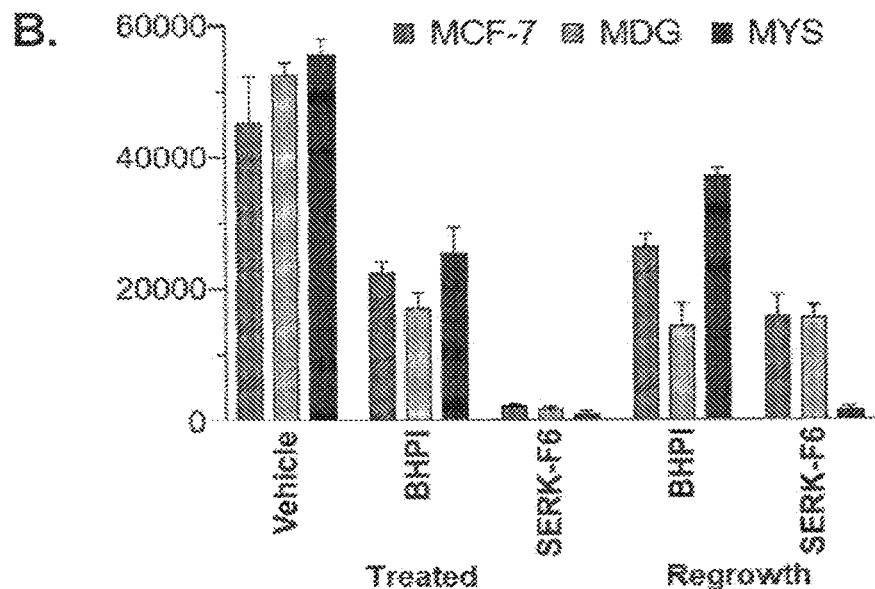

FIG. 37. SERK-F6 is the active species that leads to eradication of ERα-positive cells. a, Trypan-blue exclusion assay after 24 hours of compound incubation across a panel of ERα-positive cell lines. b, Long-term cell culture experiment with MCF-7, MDG, and MYS cells incubated with 1 µM of BHPI or SERK-F6.

Figure 38:
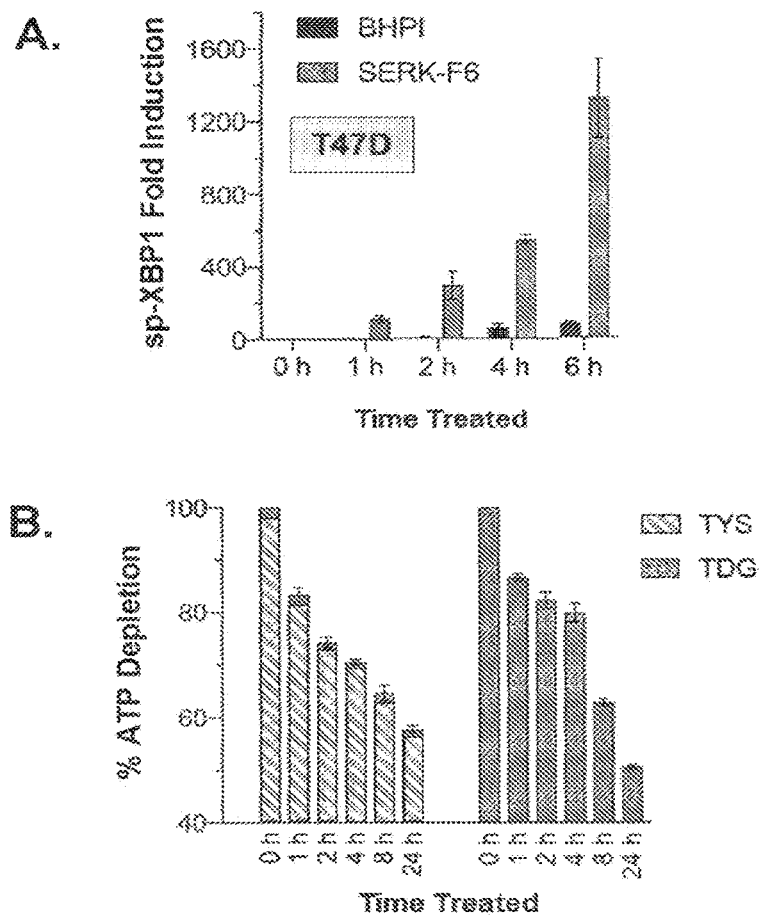
Figure 38:
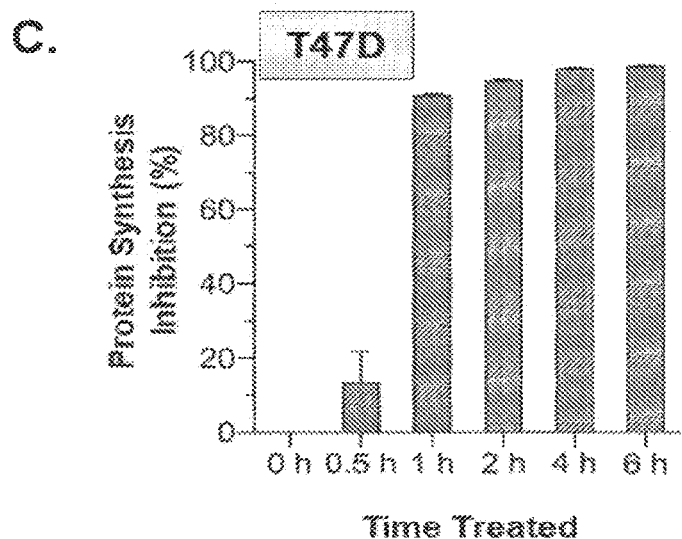

FIG. 38. SERK-F6 activates the anticipatory UPR. a, Induction of sp-XBP1 mRNA in T47D cells as a result of compound treatment after indicated times. BHPI and SERK-F6 were dosed at 1 µM. mRNA levels were quantified by RT-PCR. Error bars represent S.E.M of 6 biological replicates. b, Intracellular ATP depletion. c, SERK-F6 treatment (1 µM) leads to rapid protein synthesis inhibition in T47D cells.

Figure 39:
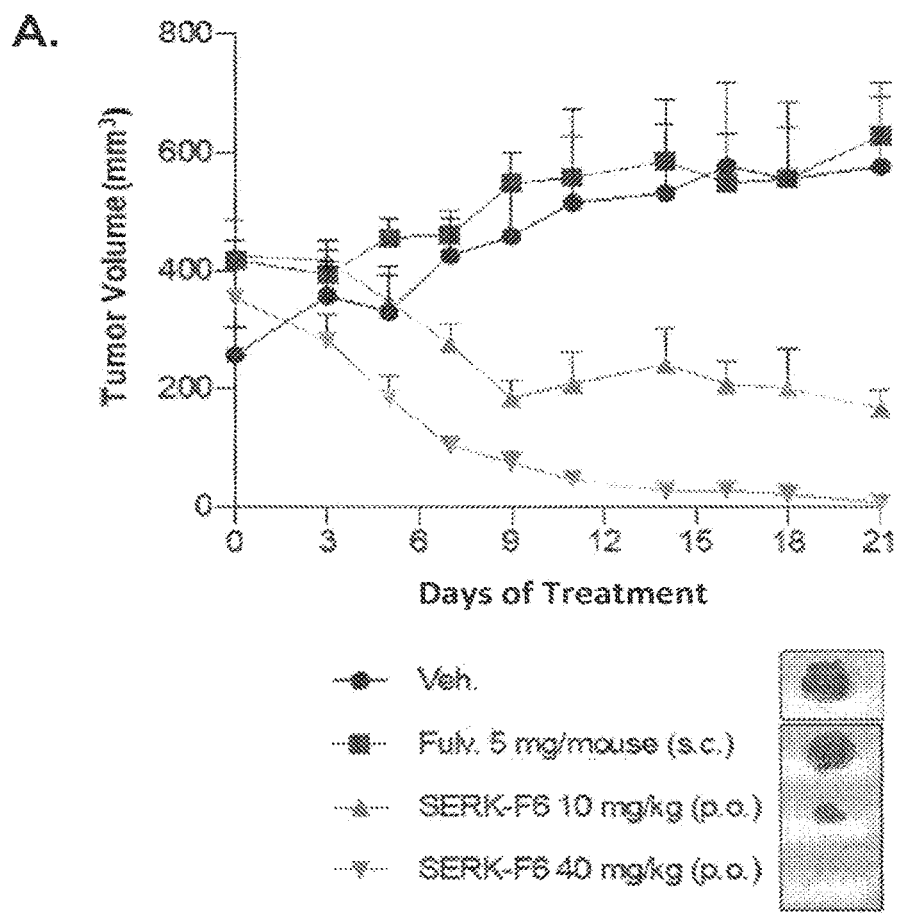
Figure 39:
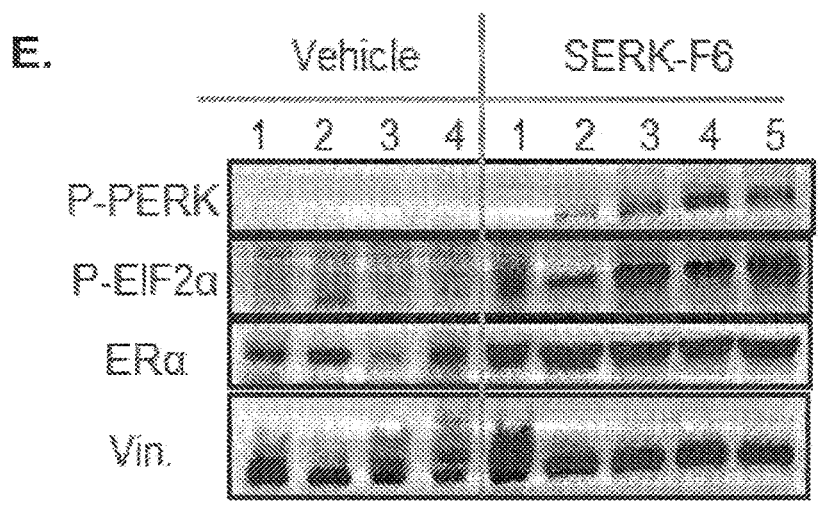

FIG. 39. SERK-F6 eradicates wild-type ERα tumors via hyperactivation of aUPR. a, MCF-7 orthotopic tumors were established in Nu/J ovariectomized mice supplemented with a 60 day E2 pellet (0.36 mg) and grown to ~400 mm$^3$ (28 days to establish), randomized, then treated with vehicle daily (n=3), vehicle weekly (n=3), fulv. weekly (5 mg/mouse, s.c., n=6), SERK-F6 daily (10 or 40 mg/kg p.o.). Vehicle arms were averaged. p values: *: p≤0.05, : p≤0.01, *: p≤0.001, ****: p≤0.0001. Tumor images were taken at the end of the study (day 21) and are representative of all tumors (n=6). b-e, MCF-7 cells were orthotopically bi-laterally grafted and tumors were grown until total tumor burden was ~ 400 mm$^3$ prior to daily treatment with vehicle or SERK-F6 (40 mg/kg p.o.). Mice (n=5 per arm) were sacrificed after 3 days (b,c) and 7 days (d,e) and tumors harvested. Tumor burden is displayed as a sum of both tumors (b,d). c,e, western blot analysis of aUPR markers, P-PERK and P-EIF2α, as well as ERα. Vinculin (Vin) was used as a loading control. Western blots displayed are representative of 4 technical replicates. E2 pellets were present during the progression of all experiments displayed. Error bars represent S.E.M.

Figure 40:
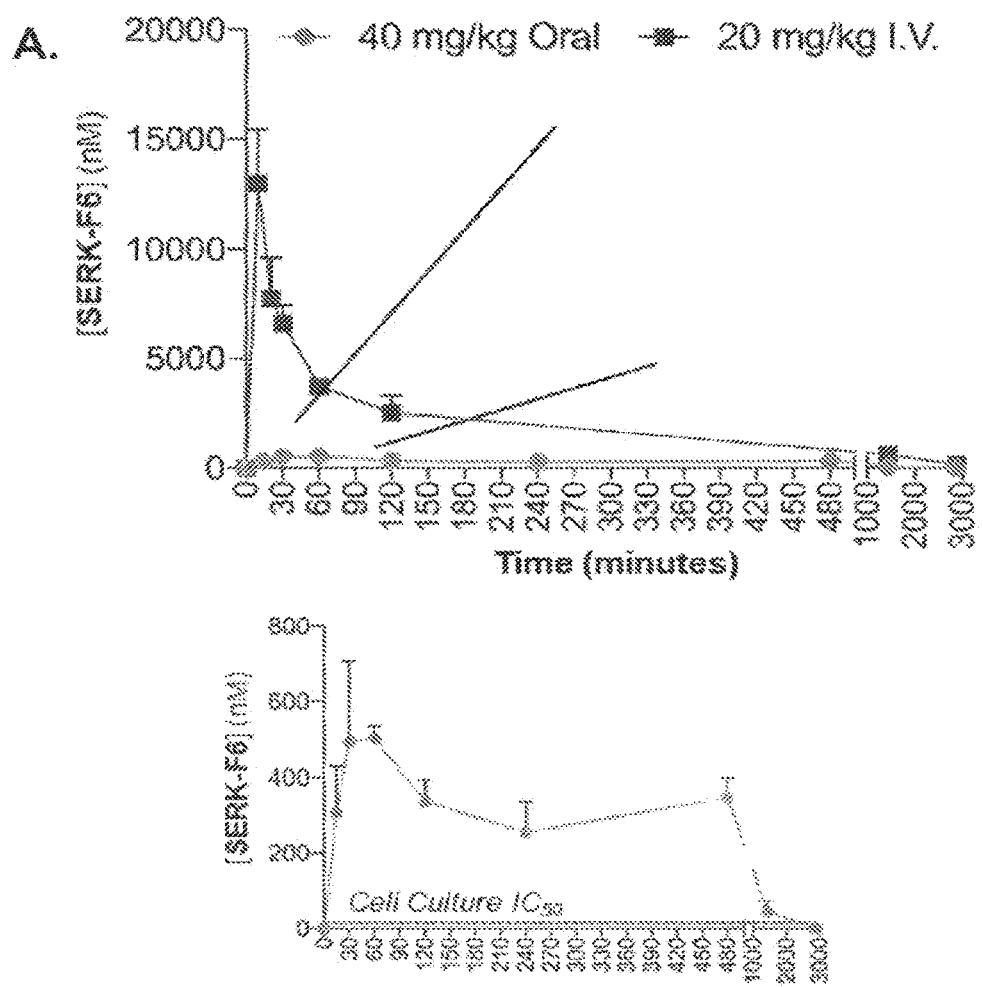
Figure 40:
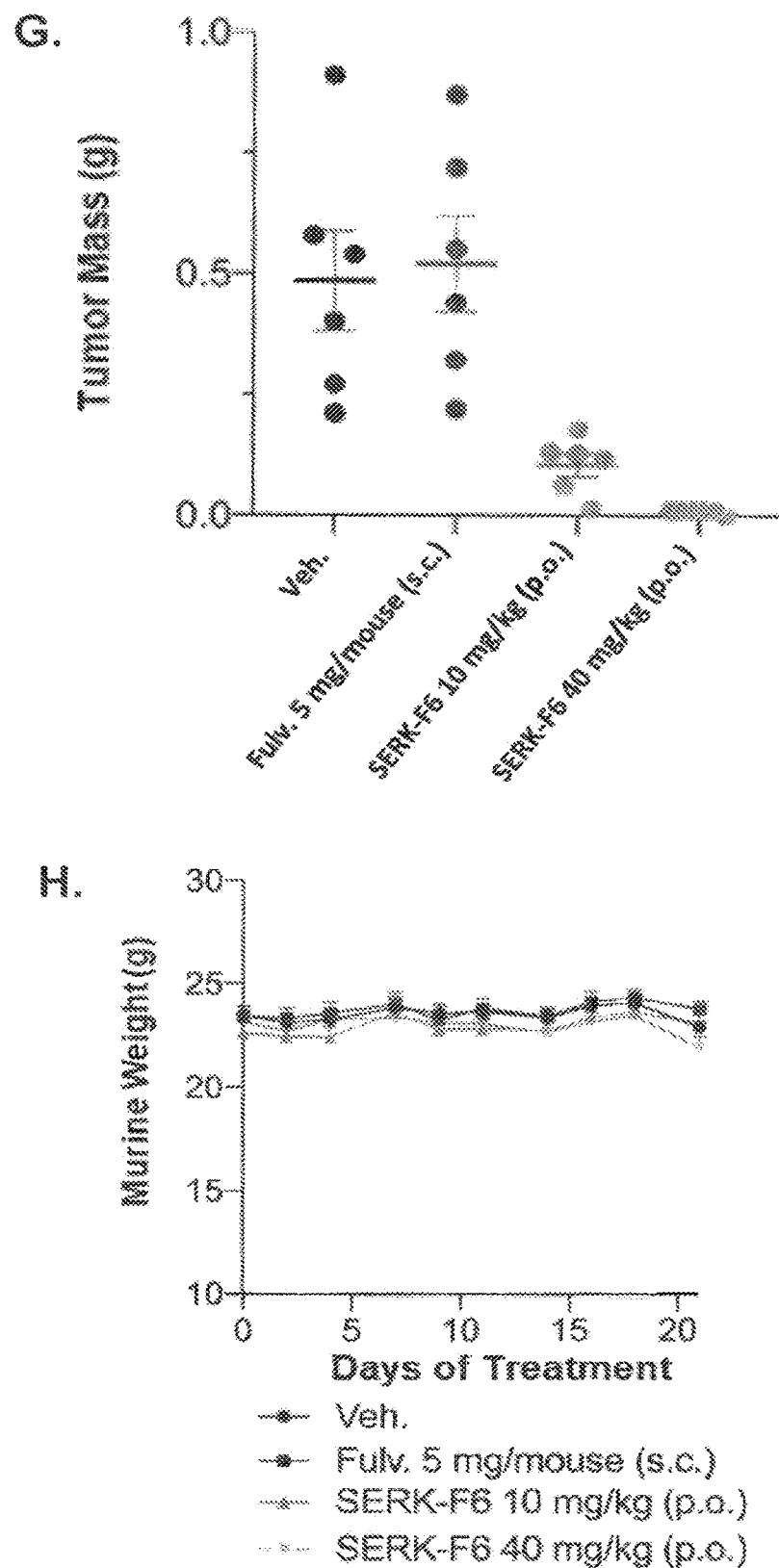

FIG. 40. SERK-F6 is tolerated, reaches biologically relevant concentrations, and crosses the blood-brain barrier in vivo. a, Serum concentrations of SERK-F6 after indicated doses, route of administration, and time. Concentration was determined via LC/MS/MS analysis. The average 24-hour $IC_{50}$ of SERK-F6 is 42 nM. b, Calculated pharmacokinetic parameters for SERK-F6. AUC: Area Under the Curve, $C_{max}$: maximum concentration, $t_{1/2}$: half-life. c,d, Mice (CD-1) were treated with the indicated doses and times, then sacrificed and their serum and brains collected. Concentrations were determined via LC/MS/MS analysis. The average blood per mouse was approximated as 58.5 mL/kg. e, SERK-F6 can achieve biologically relevant concentrations in-vivo and be well-tolerated. f-j, SERK-F6 treatment of orthotopic MCF-7 tumor bearing mice. f, Percent tumor change with comparison of Day 0 and Day 21 tumor measurements. Treatment arms: vehicle daily (n=3), vehicle weekly (n=3), fulv. weekly (5 mg/mouse, s.c., n=6), SERK-F6 daily (10 or 40 mg/kg p.o.). Vehicle arms were combined. g, Mass of tumors harvested from mice. h, observed murine weight during this MCF-7 study (n=6). i,j, Tumor measurements for MCF-7 bilateral orthotopic model (n=4-5).

Figure 41:
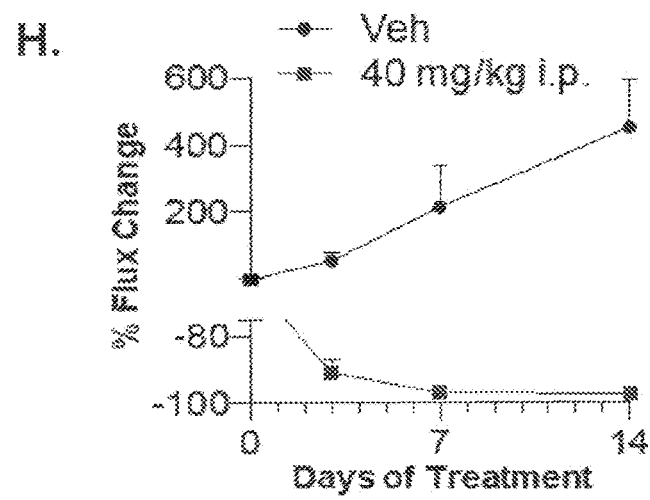

FIG. 41. SERK-F6 eradicates mutant ERα primary and metastatic breast cancer. a-c, TYS-luc. orthotopic tumors were established in NSG ovariectomized mice (no E2 pellet, 60 days to establish) and dosed daily as indicated (n=5-6). b, representative examples of bioluminescence images of SERK-F6 treated mice (7 days). d,e, TDG-luc. orthotopic tumors were established in NSG ovariectomized mice (no E2 pellet, 120 days to establish) and dosed daily as indicated (n=4-5). e, Bioluminescence image of SERK-F6 treated mouse with TDG-luc. tumor burden after 7 days. f, MYS-luc. orthotopic tumors were established in NSG ovariectomized mice (no E2 pellet, 45 days to establish) and dosed daily as indicated (n=4-5). g, MDG-luc. orthotopic tumors were established in NSG ovariectomized mice (no E2 pellet, 45 days to establish) and dosed daily as indicated (n=4-5). h, Metastatic model with MDG-luc. cells injected into the tail-vein of NSG ovariectomized mice (no E2 pellet, 1.5 months to establish) and mice were dosed daily as indicated (n=4-5).

Figure 42:
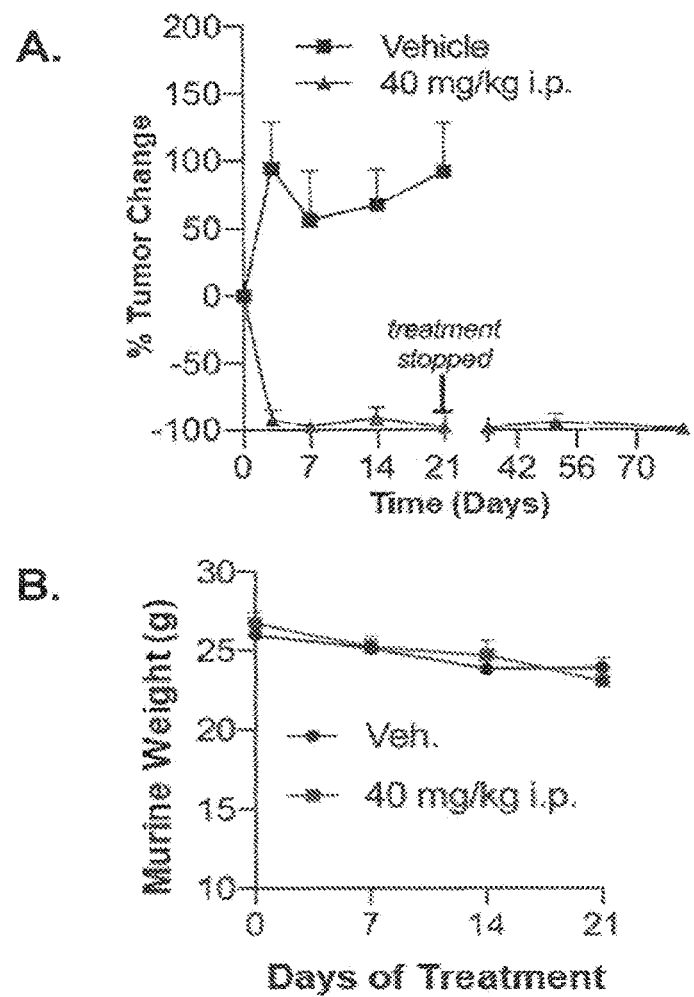

FIG. 42. The results show SERK-F6-mediated eradication of mutant ERα is dependent on quantitative cell killing. a, Treatment was stopped after 21 daily doses of SERK-F6 (40 mg/kg i.p.) and mice tumor burden was tracked via bioluminescence. b,c TYS tumor bearing mice weight during SERK-F6 treatment. d, Mice with TYS tumors treated at a lower dose of SERK-F6 (10 mg/kg p.o.) regrow tumors, however retreatment of SERK-F6 at a higher dose (40 mg/kg p.o.) leads to complete regression. e, mice weights observed during the TDG model. f, TDG-bearing mice were treated for 14 continuous days, and treatment was halted, allowing for observation of tumor regrowth via bioluminescent imaging. g, TDG-luc, orthotopic tumors were established in NSG ovariectomized mice (no E2 pellet, ~120 days to establish) and dosed daily as indicated (n=5-6). h, Mice with TDG-luc. tumors treated at a lower dose of SERK-F6 (10 mg/kg p.o.) regrow tumors after 2 months of no treatment, however retreatment of SERK-F6 at a higher dose (40 mg/kg i.p.) leads to complete regression. Error bars displayed are S.E.M.

Figure 43:
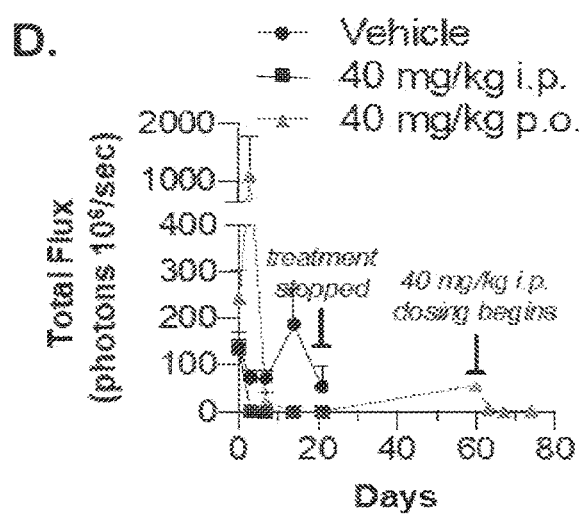

FIG. 43. SERK-F6-mediated eradication of MYS/MDG tumors is dependent on quantitative cell killing. a-b, MYS-luc. orthotopic tumors were established in NSG ovariectomized mice (no E2 pellet, ~45 days to establish) and dosed daily as indicated (n=5-6). b, Treatment of MYS-luc. tumors were stopped after 21 daily doses of SERK-F6 and mice tumor burden was tracked via bioluminescence. At day 60, regrown tumors were dosed with SERK-F6 (40 mg/kg daily i.p.). c, representative bioluminescence images. c-d, MDG-luc. orthotopic tumors were established in NSG ovariectomized mice (no E2 pellet, ~45 days to establish) and dosed daily as indicated (n=5-6). Tumor volume was tracked via total photon flux. d, MDG-luc. tumors treated with 40 mg/kg SERK-F6 p.o. daily regrow after treatment was stopped.

Regrown tumors were retreated with 40 mg/kg SERK-F6 i.p. and tumor regression was observed.

DETAILED DESCRIPTION

Cancer cells can remain quiescent for extended periods of time and then reactivate. It is therefore desirable to kill the tumor cells, not merely to prevent them from proliferating. This disclosure also provides the description of various assays for testing compounds for the ability to kill cancer cells, such as breast cancer cells.

This disclosure also identifies new compounds that are more effective than BHPI in killing breast cancer cells expressing both wild type estrogen receptor a (ERα) and ERα mutations that are common in metastatic breast cancer. These mutations are associated with resistance to current therapies. Also, this disclosure identifies compounds active against ovarian cancer cells, uterine cancer cells and other cancer cells that contain ERα.

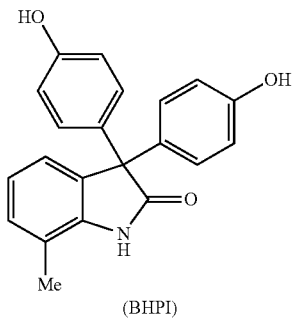

(BHPI)

The discovery of compound C(−)-105 is related in structure to BHPI. The absolute configuration of the levorotatory enantiomer of discovered compound 105 was determined to have the (R)-configuration (i.e., (R)-105). It was identified to be cytotoxic to cancer cells, but not by merely inhibiting cancer cell growth. The phenotype of (R)-105 kills cancer cells and in turn tumors. This finding is surprising in view of the compounds BHPI, fulvestrant, tamoxifen, and 01-15 because they do not kill cancer cells. These compounds merely slow cancer cell growth, i.e., they are cytostatic. Thus, (R)-105 was identified by its distinct cytotoxicity profile and ability to quantitatively kill cancer cells in-vitro. Data collected from additional in-vivo studies have proven the compound's effectiveness in the regression of tumors.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five substituents on the ring.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Carey and Sundberg (1983);

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$, wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described above or herein.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b, d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "$IC_{50}$" is generally defined as the concentration required to kill 50% of the cells in 24 hours.

Throughout this disclosure the term "(−)-105", which refers to the levorotatory enantiomer of compound 105, may be used interchangeably with terms C(−)-105, (−)-1, (R)-105, (R)-1, or SERK-F6. Similarly, (+)-105 is the dextrorotatory enantiomer, also known as (S)-105, (S)-1 or (+)-1. Also, the term "(±)-105", which refers to the racemate of compound 105, may be used interchangeably with the term (±)-1.

Embodiments of the Invention

This disclosure provides various embodiments of a compound of Formula I:

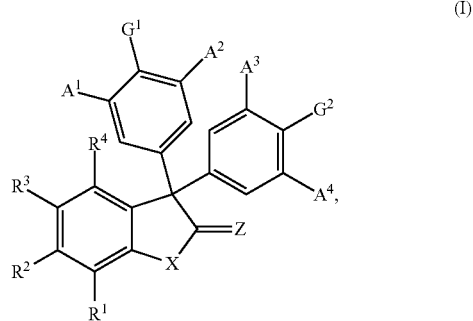

(I)

or a salt or solvate thereof; wherein $R^1$, $R^2$, $R^3$ and $R^4$ are each independently H, halo, —$OR^A$, —$SR^A$, —$N(R^A)_2$, alkyl, cycloalkyl, heterocyclyl, aryl, or heteroaryl;

$A^1$, $A^2$, $A^3$ and $A^4$ are each independently H, halo, or alkyl;

$G^1$ is halo, —$OR^B$, —$SR^B$, —$S(=O)_2R^B$, or alkyl;

$G^2$ is halo, —$OR^C$, —$SR^C$, —$S(=O)_2R^C$, or alkyl;

X and Z are each independently O, S, or —$NR^D$; and $R^A$, $R^B$, $R^C$ and $R^D$ are each independently H or alkyl, wherein, when present, —$OR^B$ and —$OR^C$ are not both —OH;

wherein each alkyl, cycloalkyl, heterocyclyl, aryl, and heteroaryl is optionally substituted with one or more substituents.

In various embodiments of Formulas I-IV described herein, $R^5$ is a substituent in the position ortho to $A^1$. In various embodiments, $R^6$ is a substituent in the position ortho to $A^2$.

In various embodiments, $R^7$ is a substituent in the position ortho to $A^3$. In various embodiments, $R^8$ is a substituent in the position ortho to $A^4$. In various embodiments, $R^5$, $R^6$, $R^7$ and $R^8$ are each independently H, halo, —$OR^A$, —$SR^A$, —$N(R^A)_2$, alkyl, cycloalkyl, heterocyclyl, aryl, or heteroaryl.

In some embodiments, the compound is the (S)-enantiomer. In other embodiments, the compound is the (R)-enantiomer. In additional embodiments, $R^A$, $R^B$, $R^C$ and $R^D$ are each independently H or —($C_1$-$C_6$)alkyl, and $R^1$, $R^2$, $R^3$ and $R^4$ are each independently H, halo, or —($C_1$-$C_6$)alkyl. In some other embodiments, $A^1$, $A^2$, $A^3$ and $A^4$ are each independently H or halo, and $G^1$ is —$OR^B$. In further embodiments, X is —$NR^D$ and Z is O. In further embodiments, $R^A$, $R^B$, $R^C$, $R^D$, $R^1$, $R^2$, $R^3$ and $R^4$ are each independently —($C_2$-$C_6$)alkyl, —($C_3$-$C_6$)alkyl, or —($C_3$-$C_6$)cycloalkyl.

In various additional embodiments, $R^1$ is $CH_3$, $CH_2CH_3$, $CF_3$, $CHF_2$, $CH_2CF_3$, $CF_2CH_3$, or $CF_2CF_3$. In yet other additional embodiments, $G^1$ is —$OR^B$, and $R^B$ is H, $CH_3$, $CH_2CH_3$, $CF_3$, $CHF_2$, $CH_2CF_3$, $CF_2CH_3$, or $CF_2CF_3$.

In further embodiments, the compound is a compound of Formula II or Formula (III):

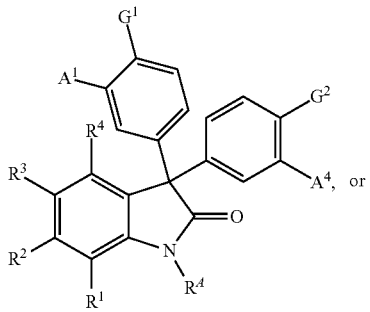

(II)

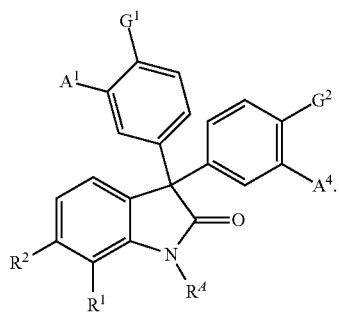

(III)

In some other embodiments, the compound is a compound of Formula IV:

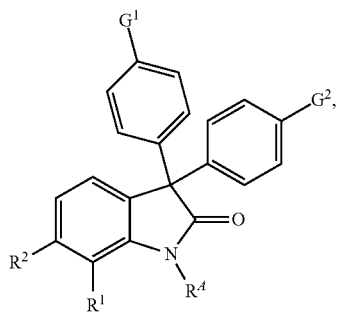

(IV)

wherein $G^1$ is —$OR^B$, and $R^B$ and $R^1$ are each independently alkyl or cycloalkyl, wherein the alkyl and cycloalkyl are optionally substituted with one or more halo groups.

In various other embodiments, one or more hydrogen atoms is deuterium or tritium, one or more carbon atoms is a carbon isotope, or a combination thereof.

In yet other embodiments, the compound is any one of compounds (S)- or (R)-2, 4, 6, 8 or 105:

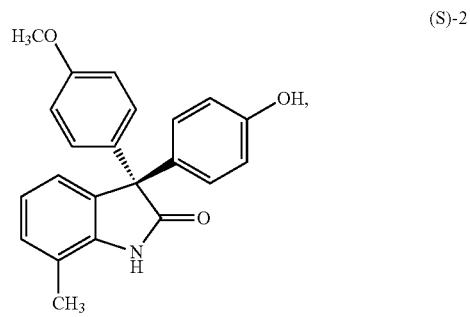

(S)-2

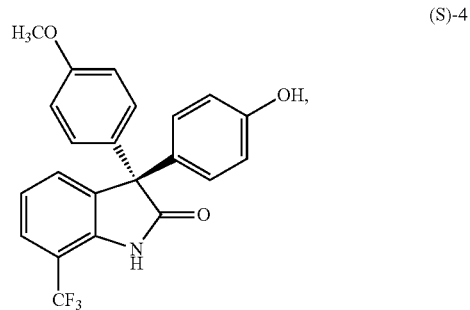

(S)-4

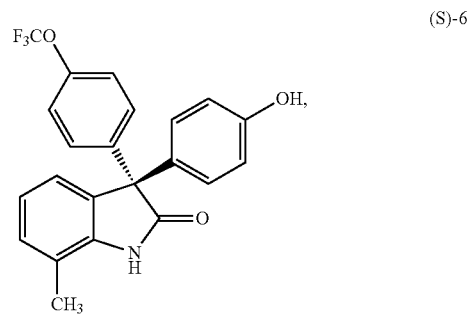

(S)-6

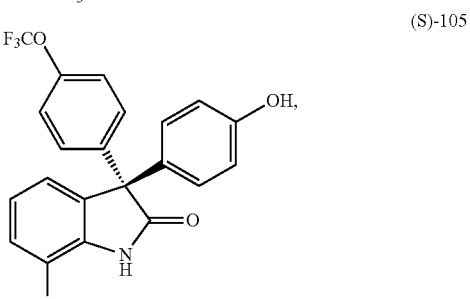

(S)-105

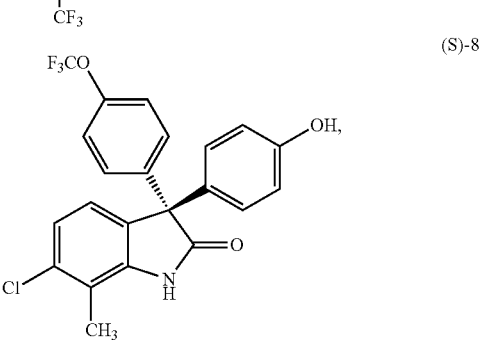

(S)-8

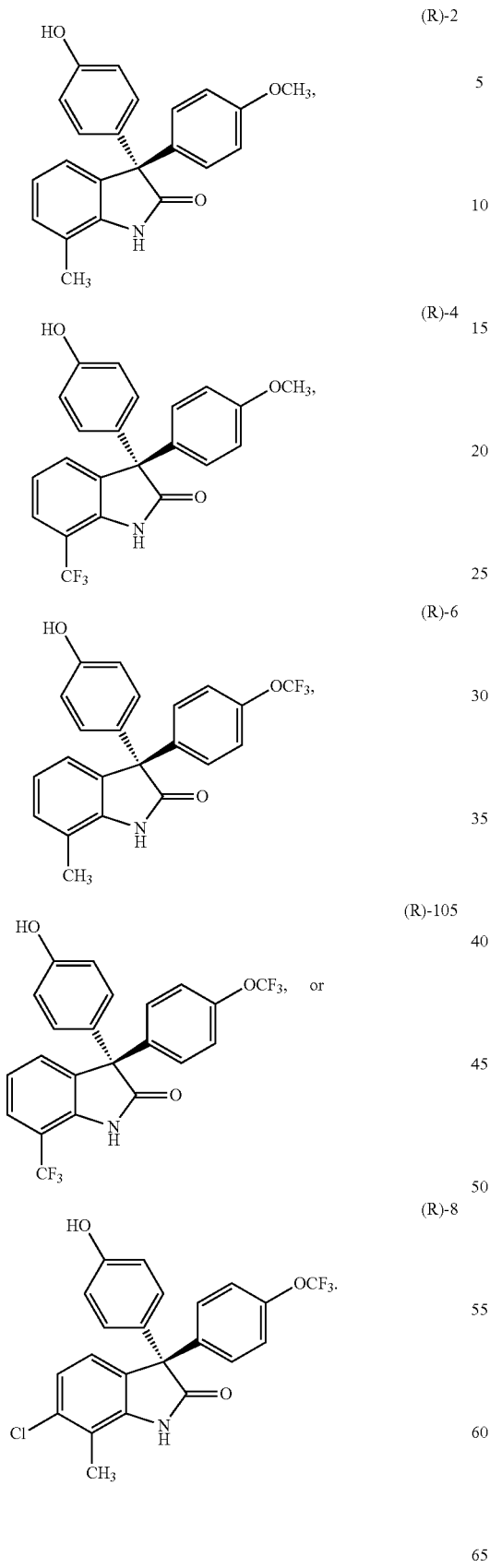
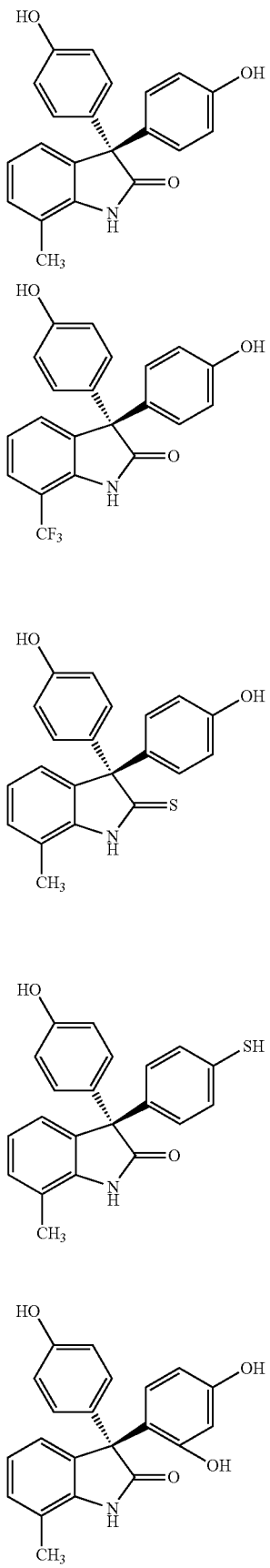
In additional embodiments, the compound is any one of the compounds shown:

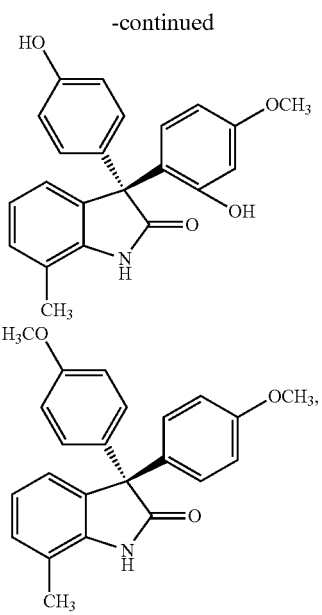

or an enantiomer thereof.

In some additional embodiments, the compound is levorotatory. In other embodiments, the compound is dextrorotatory. In other embodiments, the compound (R)-105 or (S)-105. In yet other embodiments, the compound (R)-105.

In other additional embodiments, the compound (an enantiomer or racemate) has a binding affinity for the alpha estrogen receptor (ERα), and the $IC_{50}$ of the binding affinity is less than about 500 nM. In other embodiments the $IC_{50}$ for ERα is about 1 µM to about 1000 nM, about 0.1 nM to about 750 nM, about 1 nM to about 250 nM, about 5 nM to about 500 nM, or about 10 nM to about 5000 nM. In various other embodiments, the compound kills or inhibits the growth of cancer cells by hyperactivation of the unfolded protein response (UPR) in the endoplasmic reticulum. In further embodiments, the cancer cells are ERα positive cancer cells. In some other embodiments, the cancer cells are breast cancer cells, ovarian cancer cells, or endometrial cancer cells.

This disclosure also provides a composition comprising the compound disclosed herein and a second drug. The disclosure further provides a pharmaceutical composition comprising the compound in combination with a pharmaceutically acceptable diluent, carrier, excipient, or buffer. In some embodiments of the pharmaceutical composition, the compound is a racemic mixture of (R)-105 and (S)-105. In various embodiments, a racemic mixture of a compound is a mixture of enantiomers wherein the mixture of enantiomers has a ratio of about 50:50, about 45:55, about 40:60, about 30:70, about 20:80, about 10:90, or about 5:95.

The disclosure additionally provides a method of treating a cancer comprising administering to an ERα positive cancer subject in need thereof a therapeutically effective amount of the compound, thereby treating the cancer in the subject. In further embodiments, the compound kills or inhibits growth of ERα positive cancer by hyperactivation of the unfolded protein response (UPR) in the endoplasmic reticulum. In other embodiments, the compound is a racemic mixture of (R)-105 and (S)-105. In other embodiments, the ERα positive cancer is a breast cancer, ovarian cancer, uterine cancer, cervical carcinoma, or endometrial cancer.

The disclosure additionally provides use of the compound for the treatment of an ERα positive disease in a subject in need thereof, wherein a therapeutically effective amount of the compound is administered to the subject, thereby treating the cancer in the subject. In various embodiments, the ERα positive disease is an ERα positive cancer. In other embodiments, the ERα positive cancer is a breast cancer, ovarian cancer, uterine cancer, cervical carcinoma, or endometrial cancer. In additional embodiments, the compound is administered orally, by injection, subcutaneously, sublingually, rectally, by infusion, intravenously, by dermal absorption, or through a body cavity or orifice.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

The CRISPR/Cas9 gene editing system was used to replace wild type ERα in T47D human breast cancer cells with the two most common ERα mutations seen in metastatic breast cancer, ERαY537S and ERαD538G. The resulting cell lines TYS-4 (also called TYS) and TDG-1 (also called TDG) (T47DERαY537S clone 4 and T47DERαD538G clone 1) exhibit significant resistance to tamoxifen (the active form of tamoxifen is z-4-hydroxytamoxifen; z-OHT) and to fulvestrant/ICI. (Mao et al., 2016).

To allow visualization of tumors harboring these mutations in live animals, clonal lines of TYS and TDG cells stably expressing firefly luciferase were isolated. Orthotopic mouse tumors containing these TYS-Luc and TYDG-Luc cells are visualized in live animals by bioluminescent imaging (BLI). Because the In Vivo Imaging System (IVIS) has a detection range of more than 10,000-fold and can be used to visualize progression of both primary tumors and metastatic tumors, BLI using IVIS is considered the most advanced way to evaluate the efficacy of new anticancer drugs in animal models. No other research team in a university, pharmaceutical or biotechnology company has developed cell lines combining expression of the breast cancer ERα mutations and luciferase for BLI.

Unbiased high throughput screening was used for small molecules that block ERα action to identify novel ERα biomodulators. BHPI was the first generation lead small molecule to emerge from that search. BHPI is a potent first-in-class non-competitive small molecule ERα biomodulator that kills therapy-resistant ERα positive breast and endometrial cancer cells and blocks growth of ovarian cancer cells. BHPI binds at a different site on ERα than tamoxifen and fulvestrant and has a different mechanism of action. It was demonstrated that BHPI works through ERα to induce persistent lethal hyperactivation of the anticipatory pathway of activation of the unfolded protein response (UPR). In cell culture models, BHPI selectively blocks growth, and often kills therapy-resistant, breast, ovarian and endometrial cancer cells. Notably, BHPI blocked proliferation of the TYS and TDG cells expressing ERα mutations identified in metastatic breast cancer.

In a mouse xenograft model of ERα positive breast cancer, at reasonable doses, BHPI stopped tumor growth and induced rapid and substantial tumor regression.

In xenograft studies using TYS-Luc and TDG-Luc cells after 4 weeks the vehicle control breast tumors had roughly quadrupled in cells. In contrast, the tumors in mice treated with BHPI exhibited 97%-99.5% regression.

In an orthotopic ovarian cancer xenograft model using OVCAR-3 cells, that are highly resistant to diverse anticancer drugs, the taxane paclitaxel was ineffective. BHPI alone strongly reduced tumor growth. Notably, tumors were undetectable in mice treated with BHPI plus paclitaxel and levels of the circulating cancer biomarker CA125 progressively declined to undetectable. In both studies, BHPI was well tolerated by the mice.

New Compounds with Superior Ability to Kill Therapy-resistant Breast Cancer Cells Through synthesis and evaluation, novel compounds that are superior to BHPI in their ability to kill therapy resistant breast cancer cells were identified. Compared to BHPI, the lead compound in this group, C-105 exhibits superior potency and efficacy.

Assays were developed for compounds with an improved ability to kill cancer cells. One of the assays is based on the classical criterion for cell death, loss of membrane integrity as measured by uptake of the dye Trypan Blue. This is an instrument-based assay that determines the percentage of cells in a population that have taken up Trypan Blue. All cells that have taken up Trypan Blue are dead. This novel assay is unique to the disclosed screening workflow. Although Trypan Blue uptake is universally accepted as a measure of cell death, it has not been used by others to test potential anticancer drugs. Additional assays used to evaluate cell death include fluorescence activated cell sorting (FACS) and assays based on inhibition of proliferation and determination of cell number, sometimes in conjunction with raptinal, a compound known to induce 100% cell death.

Through synthesis, small molecules were obtained that contain a novel structural feature that imparts surprising results. Compared to BHPI, the lead small molecule, C-105, exhibits far superior potency and efficacy. Notably, unlike BHPI, the active (−) enantiomer of C-105 killed 100% of TYS-Luc cells in a long-term cell culture experiment.

Moreover, current endocrine therapy drugs tamoxifen and fulvestrant are cytostatic and showed no ability at all to kill TYS and TDG breast cancer cells. Demonstrating target specificity, even at concentrations more than 10 times higher than those that effectively kill ERα positive breast cancer cells, C-105 had no effect in several ERα negative cell lines. Also, the inactive (+) enantiomer was ineffective and not toxic in ERα positive and ERα negative cell lines.

Notably, in a mouse xenograft, after administration of active (−)C-105 for just 3 days, the tumors were destroyed. Using BLI to visualize the tumors, 4 of the 5 tumors shrank (regressed) by more than 99.9% and all five shrank by more than 99%. Using calipers, within seven days, all 5 tumors had shrunk to undetectable size. After three weeks, the tumor in one mouse entirely disappeared (complete regression −100%) and the tumors in 3 of the remaining 4 mice shrank by more than 99.9%. In long duration test of whether the remaining signals are due to dead or dormant tumor cells, or whether the tumor cells will regrow, after stopping treatment and waiting 4 weeks, the one tumor that completely disappeared (complete regression −100%) remained at −100% and there was NO "MICRO-TUMOR" REGROWTH in the other mice. This is an unprecedented response.

Figure 32:
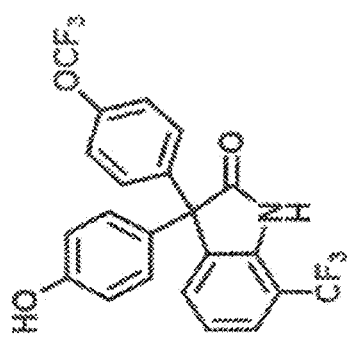
FIG. 32. (−)105 has the same mechanism of action (MOA) as BHPI.
Figure 33:
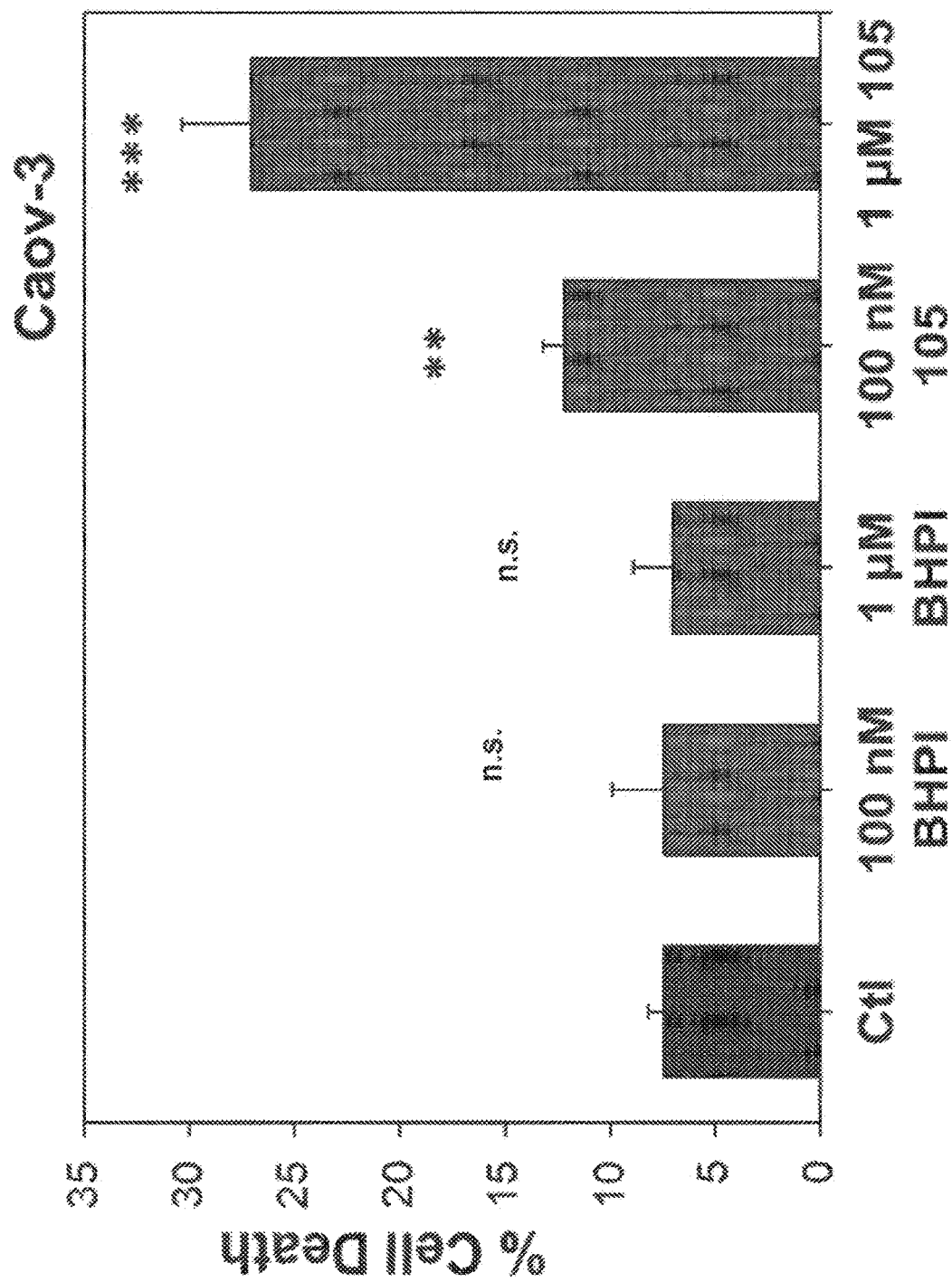
FIG. 33. 105, but not BHPI, kills therapy-resistant ovarian CaOV-3 ovarian cancer cells. (±)-105; Cell death assay: Automated Trypan Blue exclusion. (24 hours post (±)-105)

Mechanism of Action of −105: The actions of −105 include, but are not limited to, inducing lethal hyperactivation of the endoplasmic reticulum stress sensor, the unfolded protein response (UPR). The endoplasmic reticulum (EnR) stress sensor the unfolded protein response (UPR) balances the synthesis of new proteins with the availability of chaperones and other proteins that help fold and transport proteins within cells. The anticipatory UPR pathway is activated in the absence of unfolded proteins and anticipates future needs for new protein folding capacity (FIG. 32).

To induce lethal hyperactivation of the unfolded protein response (−)-105 binds to ERα in cancer cells. This leads to activation of phospholipase Cγ (PLCγ), Activated PLCγ enzymatically produces inositol triphosphate ($IP_3$). The $IP_3$ binds to and opens endoplasmic reticulum $IP_3$ receptor calcium channels in the EnR. Opening the $IP_3R$ calcium channels results in very rapid efflux of calcium stored in the lumen (interior) of the endoplasmic reticulum into the cell body. This hyperactivates the UPR. When activated, one arm of the UPR, the PERK arm, inhibits protein synthesis. Activation of another arm of the UPR, IRE1α, induces formation of the active spliced form of the mRNA encoding the transcription factor XBP-1 (spXBP-1). To restore calcium homeostasis, powerful SERCA pumps in the membrane of the endoplasmic reticulum carry out ATP dependent pumping of calcium from the cell body into the interior of the EnR. Because the $IP_3R$ calcium channels remain open, the calcium pumped into the lumen of the EnR leaks back out. This creates a futile cycle that depletes intracellular ATP.

UPR markers and inhibitors: Formation of spXBP-1 mRNA is used as a marker for UPR activation. The widely used small molecule 2-APB locks the $IP_3Rs$ closed and prevents the calcium efflux and UPR hyperactivation. The small molecule thapsigargin (THG) potently inhibits the SERCA pumps and prevents the cell from using up its ATP stores.

In a treatment and vehicle-controlled mouse tumor study, human breast cancer cells were engineered to contain both the lethal ERαY537S mutation found in metastatic breast cancer, and the gene for firefly luciferase—when the appropriate chemical is added, the firefly luciferase breaks down the chemical and light is produced. Using a sensitive detector called an imaging system, this allows us to image the tumors inside live mice. This is called bioluminescent imaging, or BLI. Large tumors were allowed to form. Then (−)-105 was injected daily under the skin for three weeks. Using the imaging system, the effect of (−)-105 on the tumors was monitored. At the same time the effect of the vehicle in which (−)-105 was dissolved on tumors was also monitored. These tumors were treated identically, except that they did not receive the test drug (−)-105.

Figure 34:
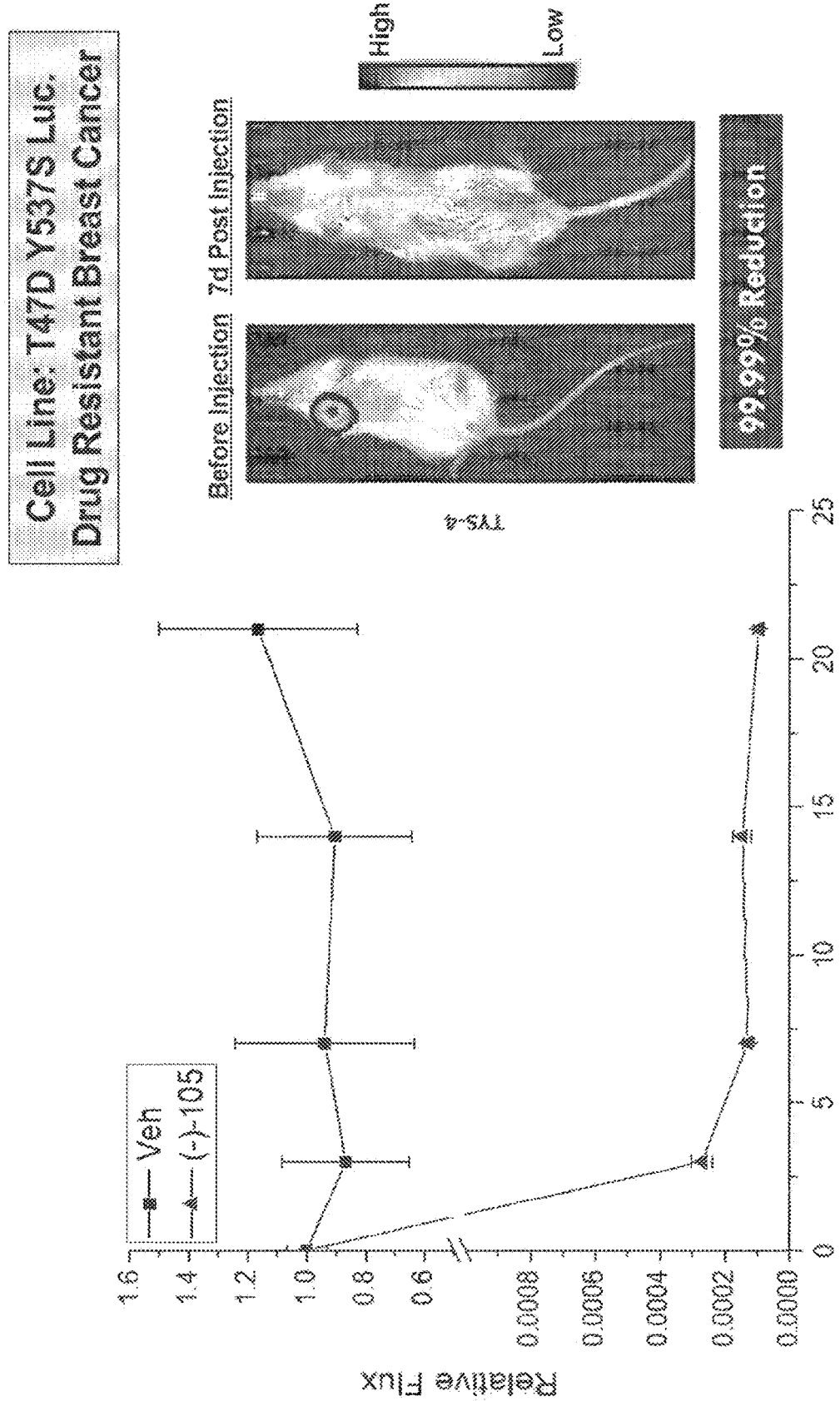
FIG. 34. (−)105 nearly eradicates ER+ drug-resistant tumors. Orthotopic breast cancer model, TYS-Luc cells, 40 mg/kg (−)-105 i.p., daily. 7d Post injection image is a much longer exposure at higher gain than before injection image.
Figure 35:
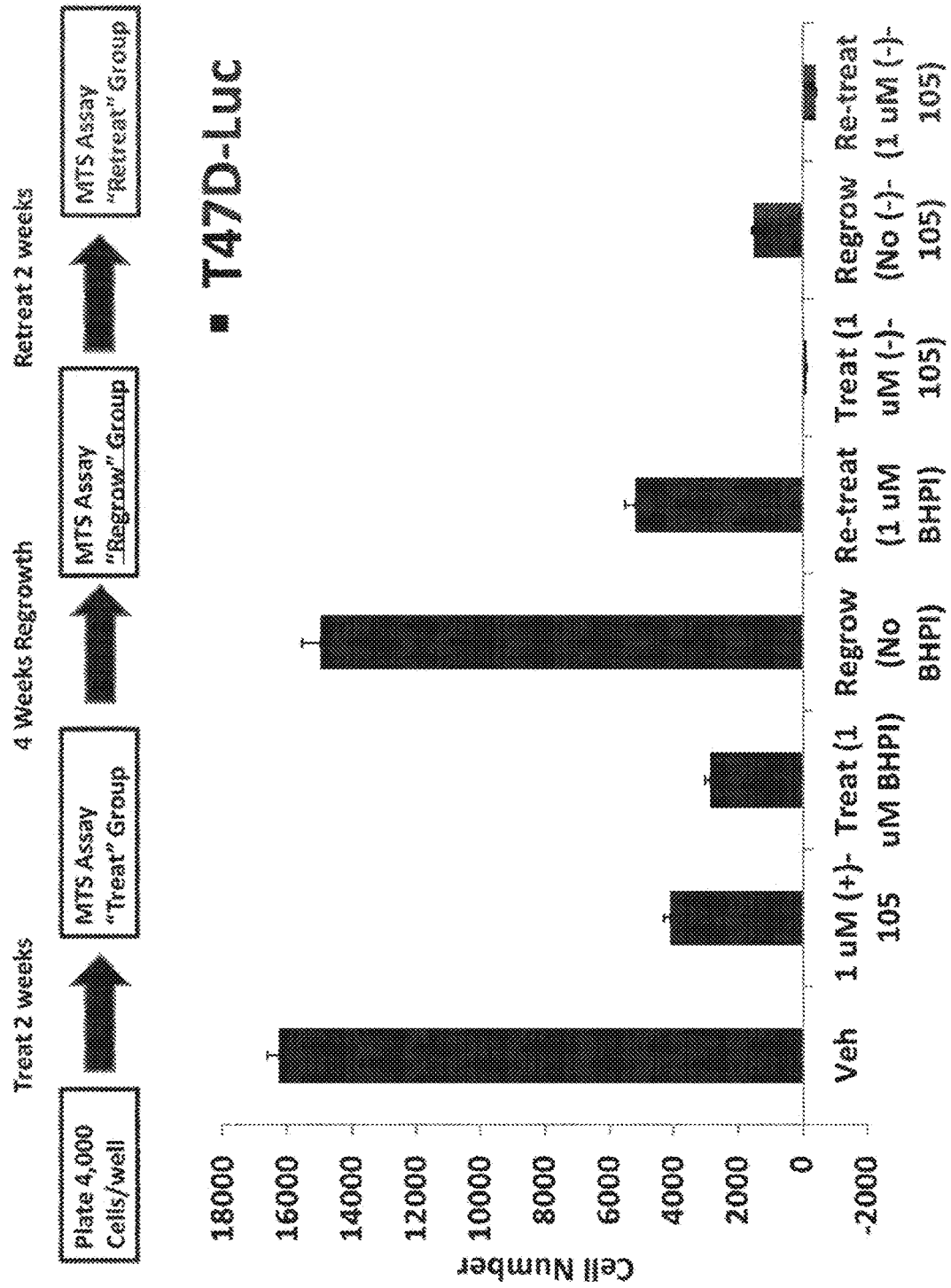
FIG. 35. (−)-105 is Superior to BHPI in Long-term Experiments Simulating Cancer Therapy. Cells: T47D-luciferase.

The image in FIG. 17 shows one of the vehicle injected control tumors at the end of the study in a side-by-side comparison with 4 of the 5 mice treated with (−)-105 (the imager can only photograph 5 mice at once). Table 1 shows the light emitted by the tumors. In a mouse xenograft, (−) 105 induces rapid and profound regression of large therapy-resistant breast tumors. Even though tumors in FIG. 17 cannot be seen visually, by greatly increasing the exposure time and sensitivity the tiny numbers of light emitting cells in the treated mice can be imaged (FIG. 34).

A study was performed to determine what happens after stopping treatment with (−)-105 (Table 2). The study was designed to show whether the micro-tumors would remain dormant, or whether they would regrow. At the end of the three-week treatment, there is residual material that gives off a tiny amount of light which are termed "micro-tumors".

Based on sensitivity of the imaging system, it is believed these micro-tumors contain anywhere from 0-~1,000 cancer cells; the micro-tumors will not be visible to the naked eye.

Seeing them requires the powerful imaging system, or a microscope. To test whether these cells are either dead, or no longer dividing and are dormant, the cells two and 4 weeks after they stopped receiving any treatment were imaged. This study tested whether growing cancer cells have been eradicated; this study continues.

Bioluminescent imaging (BLI) using luciferase shows near eradication of therapy-resistant breast tumors in mice in side-by-side imaging of one vehicle injected control mouse and 4 of 5 (−)-105-treated mice (FIG. 17). In a 3-week study, large breast tumors were present at start of treatment and regressed as shown in the image of FIG. 17. The study was performed using Orthotopic TYS-Luc (injected cells: T47DERα Y537-Luc human breast cancer cells), e.g., the most lethal ERα mutation in human in metastatic breast cancer.

Tumors were grown in NSG mice. Further details are provided in the Examples.

(b) At the end of the three-week study, there was no detectable tumor in one mouse (the tumor was eradicated; -100%), the tumors in the other four mice were nearly eradicated, with two of them very close to the limit that the imaging system can detect.
(c) Two weeks after treatment was stopped, the microtumors had not started growing again. Two of the five mice had no detectable tumors (the tumor was eradicated; -100%), two went down very slightly and one went up very slightly.
(d) Overall, the control vehicle-treated tumors continued to grow. The dramatic tumor regression was observed is therefore due to administration of the test drug (−)-105.
(e) Using calipers to measure tumor size, the tumors in all 5 mice had shrunk, (regressed) to undetectable after just 3 days of treatment with (−)-105.
(f) Overall, the health of the mice treated with (−)-105 was good. No toxicity.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques

TABLE 1

Evaluation of (−)-105 in Orthotopic Mouse Xenograft Tumors Using Bioluminescent Imaging (BLI) of Breast Tumors Expressing the Lethal ERαY537S Mutation Seen in Metastatic Breast Cancer.

| Group | Mouse | Day 0 Flux (millions of photons/sec) | Day 3 Flux (millions of photons/s) | Day 3 % Change in Tumor Flux | Day 7 Flux (millions of photons/s) | Day 7 % Change in Tumor Flux | Day 14 Flux (millions of photons/s) | Day 14 % Change in Tumor Flux | Day 21 Flux (millions of photons/s) | Day 21 % Change in Tumor Flux |
|---|---|---|---|---|---|---|---|---|---|---|
| Vehicle | 126 | 182 | 356 | +196 | 168 | −8 | 270 | +148 | 451 | +247 |
| Vehicle | 146 | 409 | 462 | +113 | 338 | −17 | 374 | −9 | 382 | −7 |
| Vehicle | 148 | 49.7 | 159 | +318 | 122 | +244 | 116 | +232 | 348 | +700 |
| Vehicle | 149 | 201 | 314 | +157 | 238 | +118 | 296 | +147 | 206 | +102 |
| Vehicle | 150 | 1,250 | 2,320 | +186 | 3,040 | +243 | 2,710 | +217 | 3,460 | +277 |
| (−)-105 | 127 | 2,130 | 0.22 | −99.99 | 0.082 | −99.996 | 0.246 | −99.99 | 0.051 | −99.998 |
| (−)-105 | 128 | 277 | 0.043 | −99.98 | 0.041 | −99.99 | 0.039 | −99.99 | 0.16 | −99.94 |
| (−)-105 | 131 | 72.6 | 0.40 | −99.45 | 0.17 | −99.77 | 0.245 | −99.66 | 0.14 | −99.81 |
| (−)-105 | 134 | 1,880 | 0.29 | −99.98 | 0.059 | −99.996 | 0 | −100 | 0 | −100 |
| (−)-105 | 147 | 1,650 | 0.17 | −99.99 | 0.18 | −99.99 | 0.071 | −99.996 | 0.046 | −99.997 |

The imaging system used for the study is more sensitive and able to pick up tiny numbers of tumor cells than standard measuring systems, such as calipers that measure tumor size, or weighing the tumors after dissecting them out of the mice.

are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy

TABLE 2

No regrowth of microtumors 4 weeks after (−)-105 treatment stopped.

| Group | Mouse | Start Recovery Flux (millions of photons/sec) | Start No Drug: % change in Tumor Flux | Week 2 No Drug Tumor Flux (millions of photons/sec) | Week 2 No Drug % Change in Tumor Flux | Week 4 No Drug Tumor Flux (millions of photons/sec) | Week 4 No Drug % Change in Tumor Flux |
|---|---|---|---|---|---|---|---|
| (−)-105 | 127 | 0.051 | −.99.997 | 0.17 | −99.991 | 0.038 | −99.998 |
| (−)-105 | 128 | 0.16 | −99.94 | 0.13 | −99.95 | 0.038 | −99.98 |
| (−)-105 | 131 | 0.14 | −99.81 | 0.11 | −99.84 | 0.084 | −99.88 |
| (−)-105 | 134 | 0 | −100 | 0 | −100 | 0 | −100 |
| (−)-105 | 147 | 0.046 | −99.997 | 0 | −100 | 0.048 | −99.997 |

Key findings in studies showed the following:
(a) (−)-105 rapidly and dramatically destroyed the tumors. After only three days, the tumors in all 5 mice shrunk, or regressed, by more than 99%. Four of the five tumors shrank by more than 99.9%.

Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Carey and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, Protecting Groups In Organic Synthesis; Wiley: New York, 1981 ("Greene") and the references cited therein, and Kocienski; Philip J.; Protecting Groups (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Scheme 1. Synthesis of (+) 105 and (−) 105.

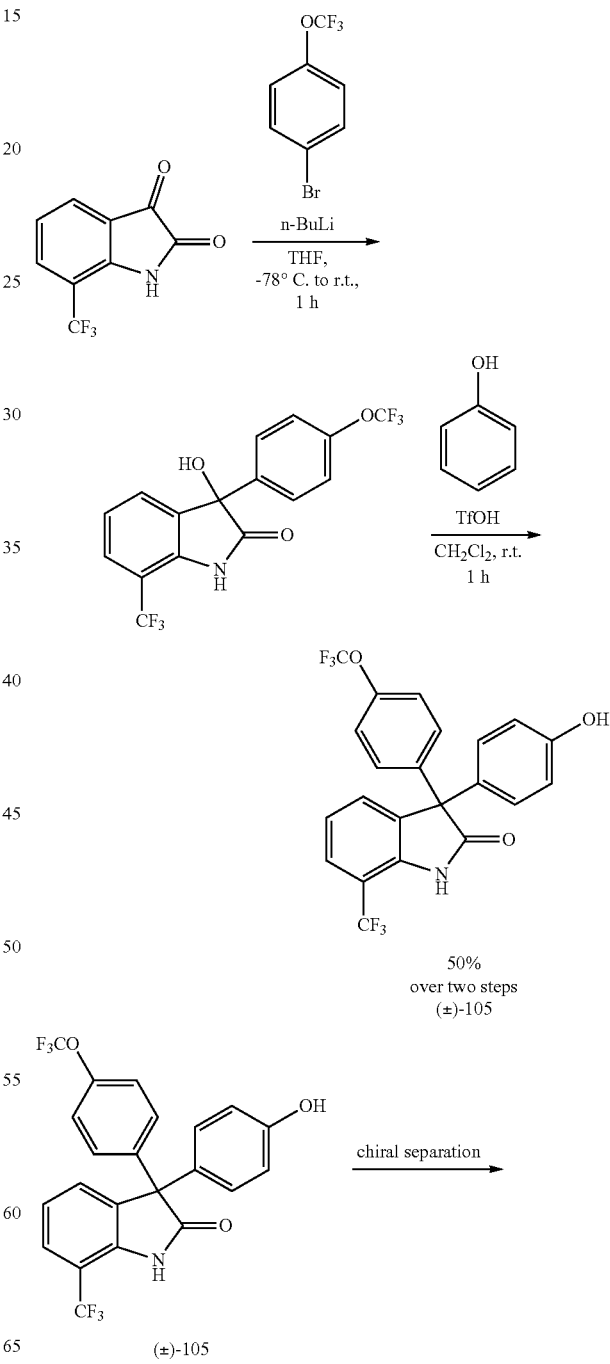

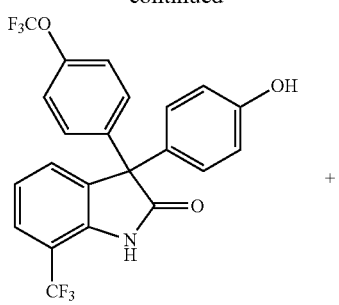
(−)-105
[α] = −134
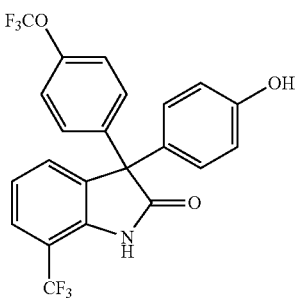
(+)-105
[α] = n.d.
Scheme 2. General synthetic route for synthesis of compounds 1-6.
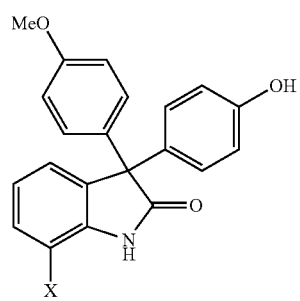
| | X | X | yield | X | yield |
|---|---|---|---|---|---|
| 7-methylisatin | CH₃ | 1 | CH₃ | 42% | 2 | CH₃ | 83% |
| 7-(trifluoromethyl)isatin | CF₃ | 3 | CF₃ | 35% | 4 | CF₃ | 82% |
*two step yields
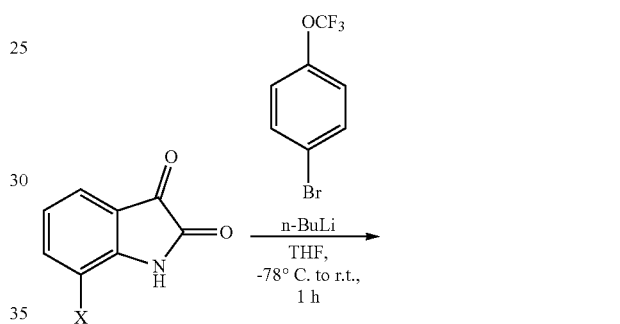
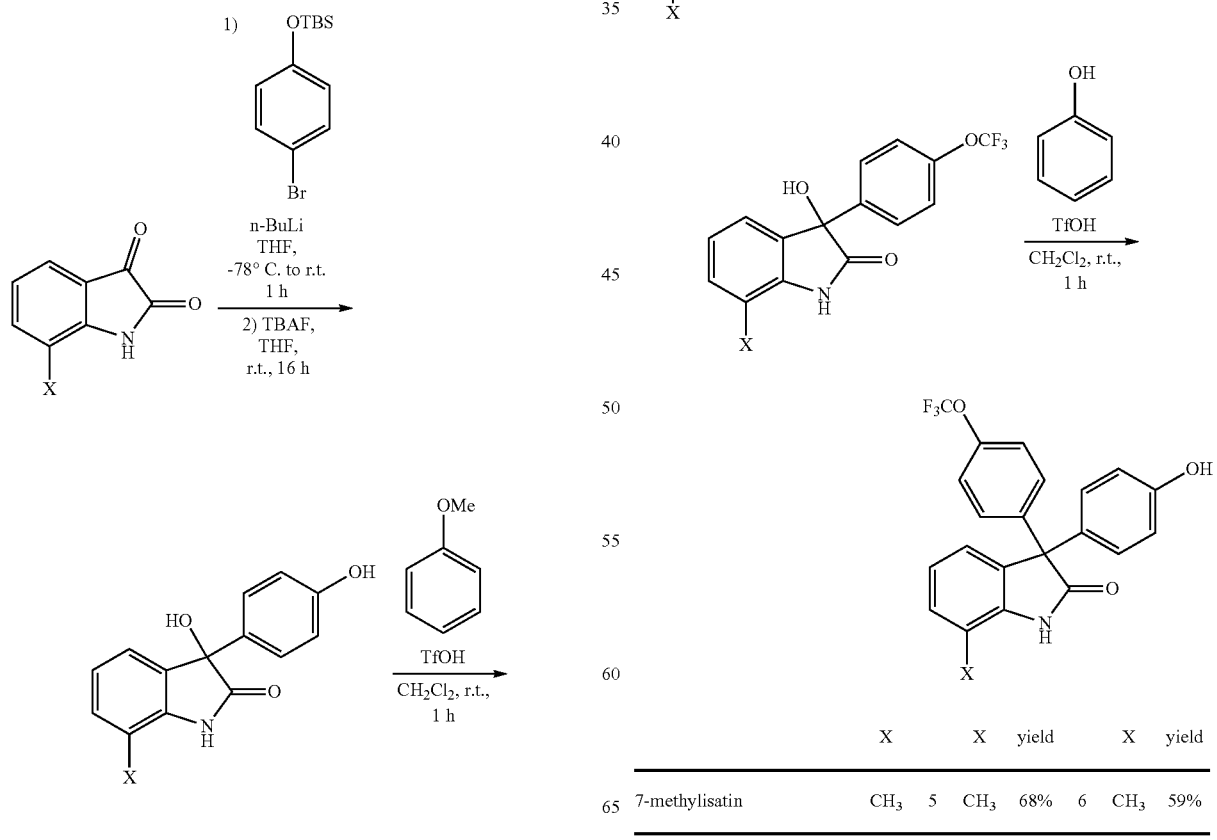
| | X | X | yield | X | yield |
|---|---|---|---|---|---|
| 7-methylisatin | CH₃ | 5 | CH₃ | 68% | 6 | CH₃ | 59% |

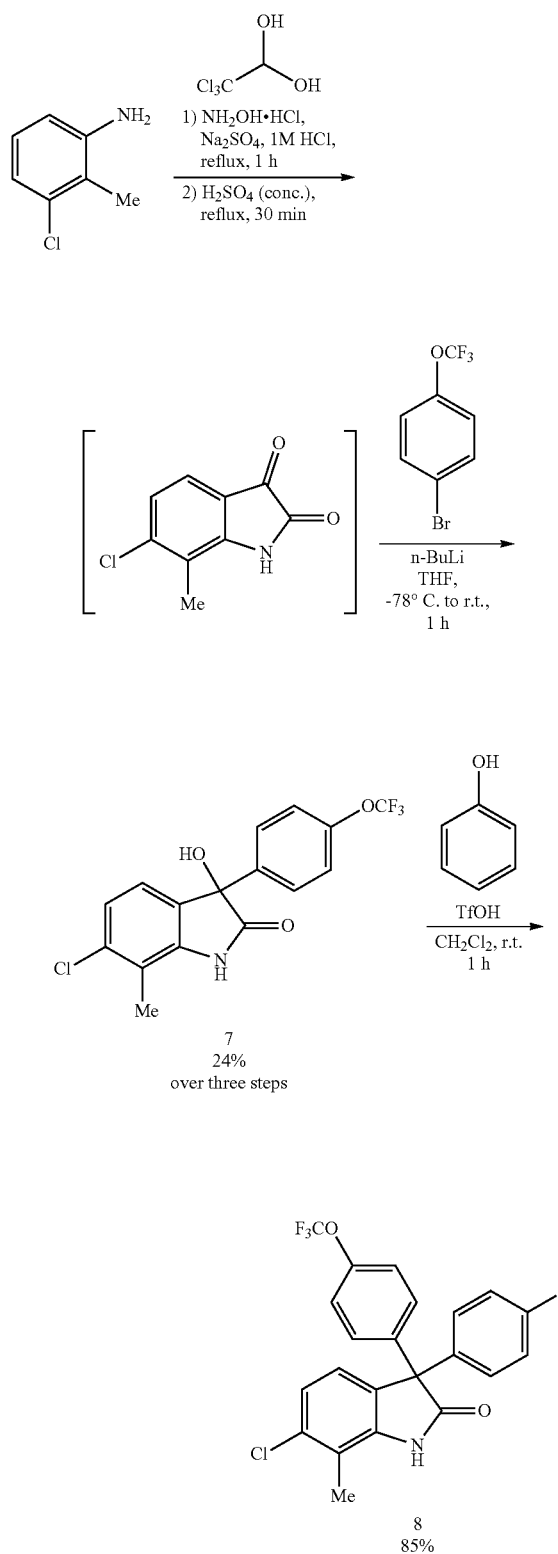
Scheme 3. Synthesis of compounds 7 and 8.
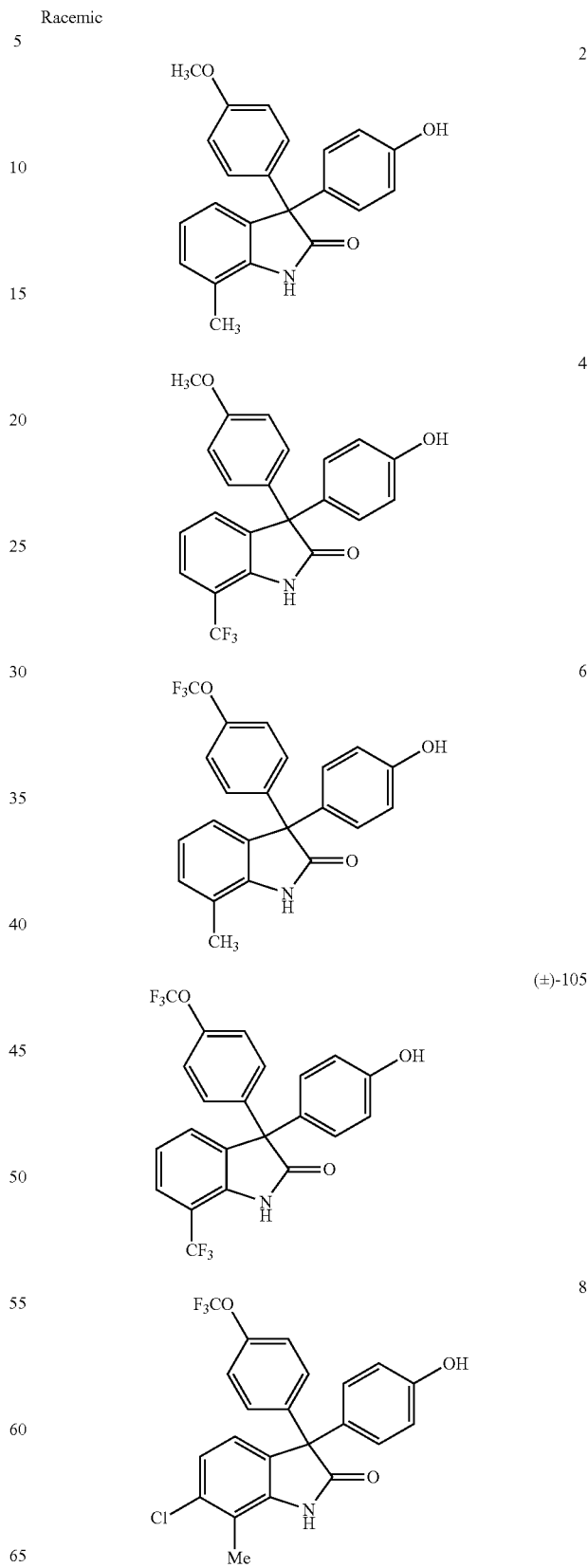
Scheme 4. Structures of synthesized compounds prepared by Schemes 1-3.
Schemes 1-3 show the general synthesis of the compounds disclosed herein, such as the compounds in Scheme 4. Detailed experimental conditions are provided in the Examples.

-continued
Enantiomers
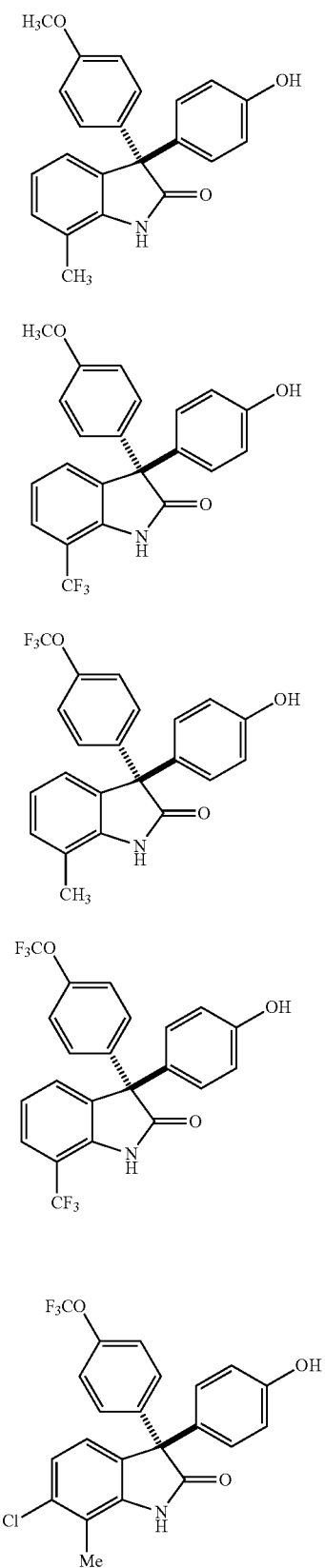
(S)-2
(S)-4
(S)-6
(S)-105
(S)-8
-continued
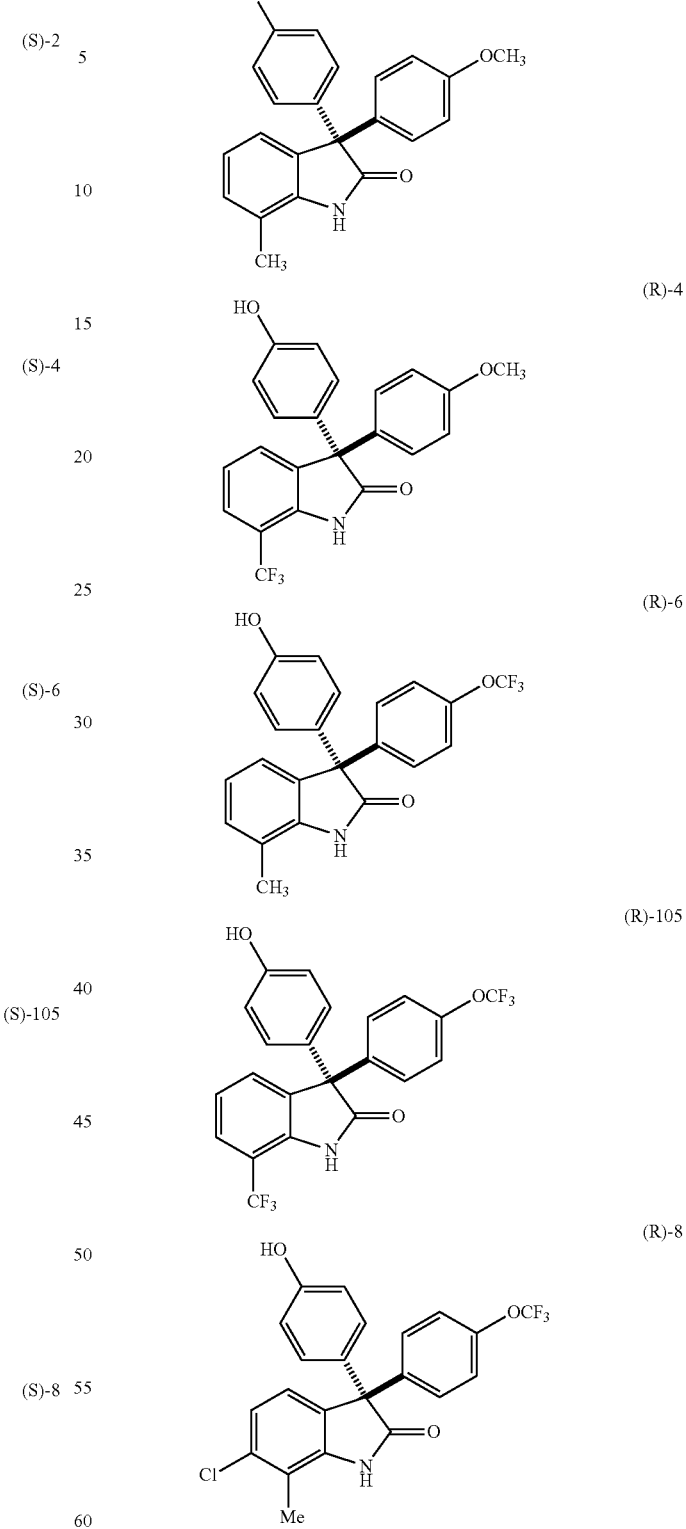
(R)-2
(R)-4
(R)-6
(R)-105
(R)-8
Basis of Assays for Killing of Cancer Cells.
TRYPAN BLUE: For decades, viable cells have been measured by their ability to exclude the dye Trypan Blue. Cells with intact membranes do not take up Trypan Blue. Dead cells, which have lost membrane integrity, take up the dye and are blue. Thus, the percentage of dead cells is the percentage of cells that are Trypan Blue positive out of the total cell population. Quantitative assessment of Trypan Blue uptake uses a cell counter from Fisher. Since the assay is instrument based, there is no observer bias in determining the percentage of Trypan Blue positive cells.

ALAMAR BLUE/RAPTINAL ASSAY: Live cells maintain a reducing environment. The non-fluorescent cell permeable ingredient of Alamar Blue® (resazurin) is taken up by cells. In living cells, it is reduced to the fluorescent compound resorufin. Using a standard curve of cell number versus fluorescence the number of live cells in a test sample can be determined. At high concentrations raptinal kills 100% of cells. The vehicle in which the test compound is dissolved is not toxic. Thus, after subtracting the blank for medium alone, the fluorescence reading for vehicle corresponds to 100% viable cells and the signal for raptinal corresponds to 0% viable cells. While this assay provides a less direct measurement of cell death than the trypan blue assay, it is more easily scaled up to large numbers of samples.

FLOW CYTOMETRY (FITC): Dying cells exhibit specific changes that can be monitored using a fluorescence activated cell sorter (FACS). One such change is loss of plasma membrane polarity. This is monitored using Annexin V. Dying cells also take up the dye propidium iodide. Propidium iodide (PI) fluoresces when it is intercalated into DNA. These assays monitor cells at specific stages of cell death. For example, cells that are dead and whose DNA has been destroyed and is in such small pieces that it no longer takes up PI are dead but are no longer seen as PI positive.

Assay Execution and Conditions

TRYPAN BLUE ASSAYS: Assays are performed on cells in 6 well plates: 300,000 cells are plated in each well of a 6-well plate in 3 ml of medium. After 24 hours, the DMSO vehicle or the indicated compound is added (in $1000^{th}$ of the vol.) The cells incubated for an additional 24 hours, and then harvested in 0.25 ml of trypsin, followed after harvest by 0.75 ml of medium. The cells are spun down and resuspended in 100-200 µl of medium left that is over the cell pellet (resuspend cells by pipetting up and down a few times). Add 10 µl to 10 µl of trypan blue. Then 10 µl is inserted into the counting slide. After inserting the slide into the Fisher TC20 counting is automatic (these many cells are needed because an accurate ratio of Trypan Blue positive to Trypan Blue negative cells requires about 200 cells in the field the instrument counts).

ALAMAR BLUE RAPTINAL ASSAYS: Cells were plated at 4,000-10,000 cells/well (96 well plate), usually in 50 µl of medium. After about 18 hours, an additional 50 µl of medium containing 2× the desired final concentration of the test compound (C-105) was added to each well. After 24 hours Alamar Blue reagent was added and fluorescence in the wells was read (BMG PheraStar or Molecular Devices Spectra Max M3 Microplate Reader). % relative death was determined by setting the reading for raptinal-treated cells to 100% dead cells and the reading for vehicle-treated cells to 0% dead cells.

FLOW CYTOMETRY (FITC) ASSAYS: Cells were seeded in 12-well plates, 75,000 cells/well, and allowed to adhere overnight. The next day, the indicated concentrations of raptinal (positive control), (−)-105, (±)-105, and (+)-105 were added and allowed to incubate at 37° C. for 24 hours (Final Volume: 1 ml, 0.1% DMSO). After incubation, cells were harvested and resuspended in 350 µl of cold Annexin binding buffer (10 mM HEPES, 140 mM NaCl, 2.5 mM $CaCl_2$, pH 7.4) premixed with Annexin V-FITC and PI dyes. Samples were analyzed on a BD Biosciences LSRII flow cytometer, and data analysis was performed using FSC Express Version 5-6. Cell death was assessed relative to a DMSO treated control.

Cell Lines Used for the Therapeutic Target: ERα Positive Breast Cancer Cells

TDG and TDG-LUC (T47DERαD538G clone 1): Both copies of the wild type ERα gene replaced with the ERαD538G mutation seen in metastatic breast cancer. These cells grow without estrogen, with a further modest increase in growth rate on addition of estrogen. Substantial resistance to z-OHT (the active form of tamoxifen) and fulvestrant// Faslodex/ICI 182,780. Slightly less resistant to z-OHT and fulvestrant/ICI than the ERαY537S cells. ERαD538G is the single most common mutation in metastatic breast cancer. Therefore, these cells are critical for testing. (TDG-LUC) TDG cells stably transfected to express firefly luciferase. Transcription of the luciferase gene is driven by a constitutively active CMV promoter.

TYS and TYS-LUC (T47DERαY537S CLONE 4): Both copies of wild type ERα gene replaced with the ERαY537S mutation seen in metastatic breast cancer. Fast growth without estrogen. No additional growth stimulation by estrogen. Substantial resistance to z-OHT and fulvestrant/ICI. Slightly more resistant to current drugs than the ERαD538G cells. This is the most lethal mutation in metastatic breast cancer. (TYS-Luc) TYS cells stably transfected to express firefly luciferase. Transcription of the luciferase gene is driven by a constitutively active CMV promoter.

T47D: ERα positive, require estrogen to grow, sensitive to z-OHT and fulvestrant/ICI; parental cell line, widely used, but less common than MCF-7 cells. The lower levels of ERα in T47D cells, compared to MCF-7 cells, are more in-line with ERα levels in actual breast cancers. T47D cells were tested in part because the T47D cells require higher concentrations of BHPI to inhibit proliferation and kill than the two cell lines expressing mutant ERα.

MCF-7 (Michigan Cancer Foundation-7): ERα positive, the most widely used ERα positive breast cancer cell line. Estrogen greatly stimulates their growth; sensitive to z-OHT and fulvestrant/ICI.

ECC-1: ERα positive uterine cancer cells.

Caov3: Drug resistant ERα positive ovarian cancer cells. BHPI blocks growth of Caov-3 cells but does not kill them. These cells are completely resistant to tamoxifen and fulvestrant and partially resistant to cisplatin and paclitaxel.

ERα Negative Cells Used to Test for Toxicity and Off-Target Effects

HeLa: These are ERα negative cells of cervical origin. The most widely used human cell line.

MDA-MB-231 cells: These are ERα negative cells and are the most common model for triple negative breast cancer. Highly metastatic. These cells are used because in this work they are more sensitive to non-specific growth inhibition than most other cell lines. They are therefore a stringent test for non-specific toxicity.

MCF-10A (Michigan Cancer Foundation-10A): Immortal, but not tumorigenic, ERα negative breast cell line.

Statistics

Unless otherwise stated there are at least 3 biological replicates of each sample (n=3). Data is presented as the average of the replicates±S.E.M. For statistical significance comparisons are for the cells treated with the vehicle compared to the cells treated with the same concentration of 105, BHPI, or other compounds, wherein $P<0.05$;  $P<0.01$; * $P<0.001$ all using Students T-test.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, u-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antitumor agents and have higher potency and/or reduced toxicity as compared to BHPI. Preferably, compounds of the invention are more potent and less toxic than BHPI, and/or avoid a potential site of catabolic metabolism encountered with BHPI, i.e., have a different metabolic profile than BHPI.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kills, and the biological significance of the use of transplantable tumor screens are known. In addition, ability of a compound to treat cancer may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthetic Procedures

General Information: Unless otherwise stated, all reagents were purchased from commercial sources and used without further drying or purification. Solvents used herein were dried after being passed through activated alumina columns. All reactions were run in flame-dried glassware under a positive pressure of nitrogen gas. $^1$H NMR and $^{13}$C NMR experiments were conducted on a Bruker cryoprobe at 500 MHz and 188 MHz respectively. Spectra obtained in CD$_3$OD were referenced for 3.31 ppm and 49.00 ppm for $^1$H and $^{13}$C NMR spectra respectively. NMR multiplicities are reported as: s=singlet, d=doublet, t=triplet, q=quartet, m=multiplet. $^{13}$C multiplicities are all singlets unless otherwise noted.

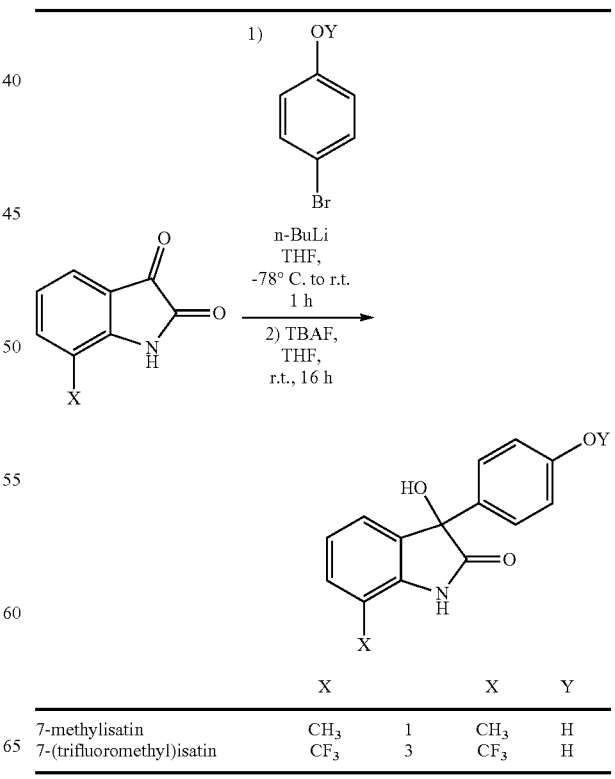

| | X | | X | Y |
|---|---|---|---|---|
| 7-methylisatin | CH$_3$ | 1 | CH$_3$ | H |
| 7-(trifluoromethyl)isatin | CF$_3$ | 3 | CF$_3$ | H |

Procedure A: A round bottom flask was charged with desired phenyl bromide (3.08 mmol) and dissolved in THF (3.0 mL). The reaction mixture was cooled to −78° C. and a solution of n-BuLi (2.77 mmol, 1.7 mL) added dropwise over 10 minutes. The reaction was stirred for 1 hour. In another flask, the desired isatin (1.54 mmol) was added and dissolved in THF (9.4 mL). This solution of isatin was added to the reaction vessel dropwise over 10 minutes. The resultant mixture was stirred at −78° C. for 1 hour, warmed to r.t., and then stirred for 1 hour. The reaction was quenched with water (10 mL). The solution was extracted with ethyl acetate (3×) and the combined organic layers were dried over sodium sulfate, filtered, and concentrated in vacuo. The resulting oil was run through a silica plug (elution solvent gradient: 10% EtOAc/Hexanes ramped to 100% EtOAc). The eluted species was then charged to a round bottom flask, purged of air, placed under nitrogen atmosphere, and dissolved in THF (15.4 mL). A solution of tetra-n-butylammonium fluoride (5.4 mL) was added and the reaction vessel. After 16 hours of stirring, the reaction was quenched with a 1:1 solution of saturated ammonium chloride$_{aq}$:water (30 mL). The solution was extracted with ethyl acetate (3×) and the combined organic layers were dried over sodium sulfate, filtered, and concentrated in vacuo. The resultant oil was then purified via column chromatography.

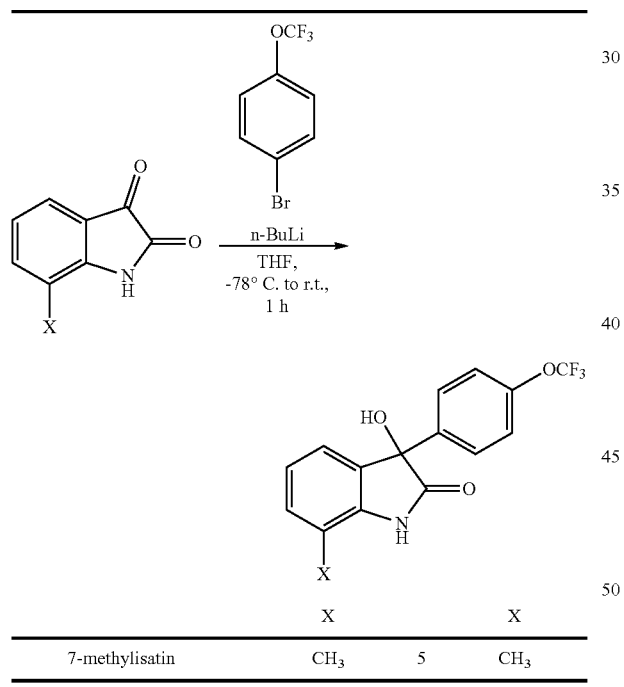

| | 7-methylisatin | CH$_3$ | 5 | CH$_3$ |

Procedure B: A round bottom flask was charged with desired phenyl bromide (3.35 mmol) and dissolved in THF (2.8 mL). The reaction mixture was cooled to −78° C. and a solution of n-BuLi (2.79 mmol, 1.8 mL) added dropwise over 10 minutes. The reaction was stirred for 1 hour. In another flask, the desired isatin (1.86 mmol) was added and dissolved in THF (5.6 mL). This solution of isatin was added to the reaction vessel dropwise over 10 minutes. The resultant mixture was stirred at −78° C. for 1 hour, warmed to r.t., and then stirred for 1 hour. The reaction was quenched with water (10 mL). The solution was extracted with ethyl acetate (3×) and the combined organic layers were dried over sodium sulfate, filtered, and concentrated in vacuo. The resulting oil was run through a silica plug (elution solvent gradient: 10% EtOAc/Hexanes ramped to 100% EtOAc).

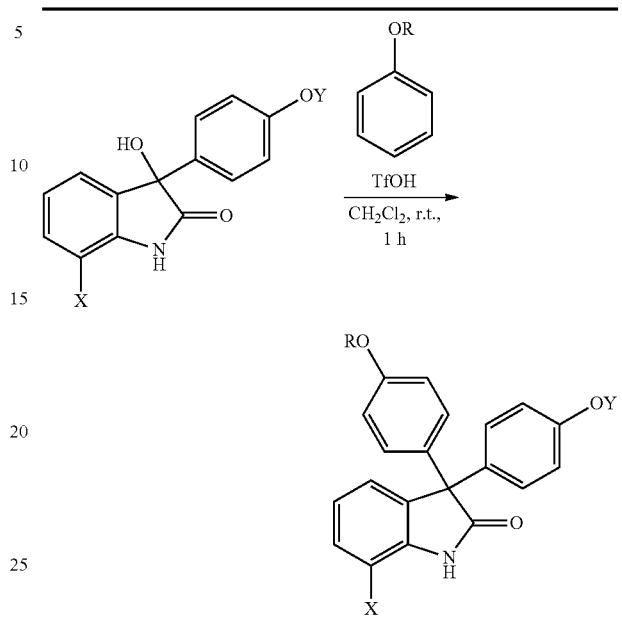

| | X | Y | | X | Y | R |
|---|---|---|---|---|---|---|
| 1 | CH$_3$ | H | 2 | CH$_3$ | H | CH$_3$ |
| 3 | CF$_3$ | H | 4 | CF$_3$ | H | CH$_3$ |
| 5 | CH$_3$ | CF$_3$ | 6 | CH$_3$ | CF$_3$ | H |

Procedure C: A round bottom flask was charged with desired tertiary alcohol (0.93 mmol) and desired phenol (4.2 mmol) and dissolved in dichloromethane (4.7 mL). The reaction mixture was then placed in an ice bath and triflic acid (TfOH, 0.42 mL) was then added dropwise. The reaction vessel was removed from the ice bath and stirred at room temperature for 1 hour. The reaction mixture was then poured into an ice-filled sodium bicarbonate and the aqueous solution was extracted with ethyl acetate (3×). The combined organic layers were dried over sodium sulfate, filtered, and concentrated in vacuo. The resultant oil was then purified via column chromatography.

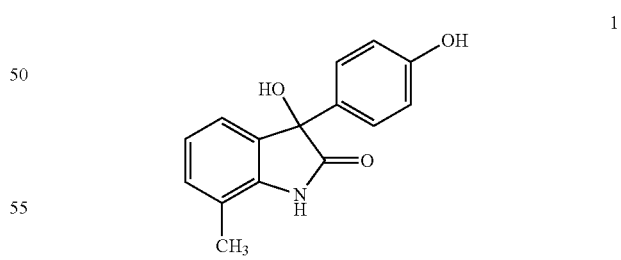

3-hydroxy-3-(4-hydroxyphenyl)-7-methylindolin-2-one (1): Utilizing General Procedure A, 1 was isolated in 45% yield over two steps. $^1$H NMR (CD$_3$OD, 500 MHz): δ 7.19 (d, J=8.86 Hz 2H), 7.10 (d, J=7.59 Hz 1H), 7.02 (d, J=7.46 Hz 1H), 6.96 (dd, J=7.54 Hz, 7.49 Hz 1H), 6.71 (d, J=8.72 Hz 2H), 2.29 (s, 3H).

$^{13}$C NMR (CD$_3$OD, 188 MHz): δ 182.20, 158.40, 141.39, 134.47, 132.71, 131.78, 128.23, 123.86, 123.48, 121.00, 115.93, 79.17, 16.58.

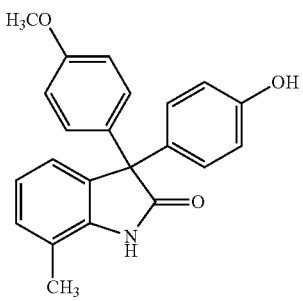

2

3-(4-hydroxyphenyl)-3-(4-methoxyphenyl)-7-methylindolin-2-one (2): Utilizing General Procedure C, 2 was isolated in 83% yield. $^1$H NMR (CD$_3$OD, 500 MHz) δ: 7.12 (d, J=8.93 Hz, 2H), 7.02 (m, 3H), 6.94 (m, 2H), 6.82 (d, J=6.82 Hz, 2H), 6.69 (d, J=8.74 Hz), 3.74 (s, 3H), 2.30 (s, 3H).

$^{13}$C NMR (CD$_3$OD, 188 MHz) δ: 182.87, 160.24, 157.71, 140.70, 135.73, 135.65, 134.26, 130.58, 130.54, 130.38, 124.48, 123.51, 121.02, 116.02, 114.64, 63.36, 55.67, 16.81.

HRMS (ESI): m/z calc. for C$_{22}$H$_{20}$NO$_3$ [M+H]$^+$ 346.1443, found: 346.1442.

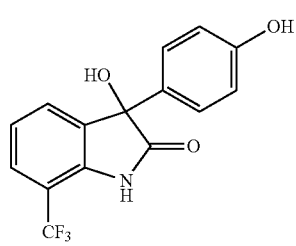

3

3-hydroxy-3-(4-hydroxyphenyl)-7-(trifluoromethyl)indolin-2-one (3): Utilizing General Procedure A, 3 was isolated in 35% yield over two steps. $^1$H NMR (CD$_3$OD, 500 MHz) δ: 7.54 (m, 1H), 7.43 (d, J=7.49 Hz 1H), 7.19 (m, 3H), 6.74 (d, J=8.74 Hz, 2H).

$^{13}$C NMR (CD$_3$OD, 188 MHz) δ: 181.60, 158.73, 140.54 (q, J=2.25 Hz), 136.85, 131.80, 129.89, 128.89, 126.90 (q, J=4.6 Hz), 125.16 (q, J=270.76 Hz), 123.74, 116.16, 113.56 (q, J=33.17 Hz), 77.66.

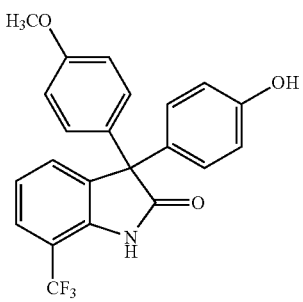

4

3-(4-hydroxyphenyl)-3-(4-methoxyphenyl)-7-(trifluoromethyl)indolin-2-one (4): Utilizing General Procedure C, 4 was isolated in 82% yield. $^1$H NMR (CD$_3$OD, 500 MHz) δ: 7.50 (dd, J=8.09 Hz, 0.62 Hz, 1H), 7.40 (dd, J=7.76 Hz, 0.64 Hz, 1H), 7.18 (ddd, J=8.08 Hz, 7.46 Hz, 0.87 Hz, 1H), 7.12 (d, J=8.87 Hz, 2H), 7.01 (d, J=8.76 Hz, 2H), 6.86 (d, J=8.87 Hz, 2H), 6.72 (d, J=8.75 Hz 2H), 3.77 (s, 3H).

$^{13}$C NMR (CD$_3$OD, 188 MHz) δ: 182.24, 160.55, 158.10, 139.74 (m), 137.85, 134.73, 133.30, 130.98, 130.50, 130.49, 125.72 (q, J=4.6 Hz, 125.23 (q, J=270.71 Hz), 123.32, 116.27, 114.89, 113.55 (q, J=33.50 Hz), 62.12, 55.72.

HRMS (ESI): m/z calc. for C$_{22}$H$_{17}$NO$_3$F$_3$[M+H]$^+$ 400.1161, found: 400.1154.

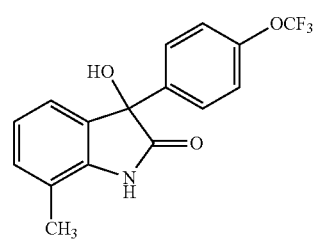

5

3-hydroxy-7-methyl-3-(4-(trifluoromethoxy)phenyl)indolin-2-one (5): Utilizing General Procedure B, 5 was isolated in 68% yield over two steps. $^1$H NMR (CD$_3$OD, 500 MHz) δ: 7.46 (d, J=8.83 Hz 2H), 7.22 (dd, J=1.02 Hz, 8.98 Hz, 2H), 7.13 (m, 1H), 6.98 (m, 2H), 2.31 (s, 3H).

$^{13}$C NMR (CD$_3$OD, 188 MHz) a: 181.41, 150.1 (q, J=1.6 Hz), 141.55, 141.46, 134.03, 132.19, 128.67, 124.13, 123.4, 121.90 (q, J=255.61 Hz), 121.32, 79.04, 16.61.

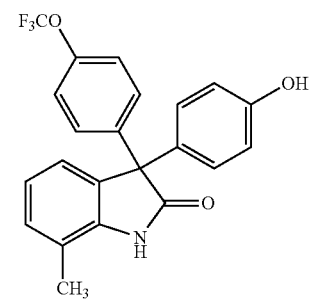

6

3-(4-hydroxyphenyl)-7-methyl-3-(4-(trifluoromethoxy)phenyl)indolin-2-one (6): Utilizing General Procedure C, 6 was isolated in 59% yield. $^1$H NMR (CD$_3$OD, 500 MHz) δ: 7.30 (d, J=8.86 Hz 2H), 7.20 (m, 2H), 7.08 (m, 1H), 7.03 (d, J=8.74 Hz, 2H), 6.99 (m, 2H), 6.72 (d, J=8.73 Hz, 2H), 2.31 (s, 3H).

$^{13}$C NMR (CD$_3$OD, 188 MHz) δ: 182.00, 158.02, 149.56 (q, J=1.47 Hz), 143.12, 140.82, 134.85, 133.55, 131.22, 130.77, 130.56, 124.51, 123.73, 121.89 (q, J=255.61 Hz), 121.78, 121.32, 116.23, 63.49, 16.82.

HRMS (ESI): m/z calc. for C$_{22}$H$_{17}$NO$_3$F$_3$[M+H]$^+$ 400.1161, found: 400.1163.

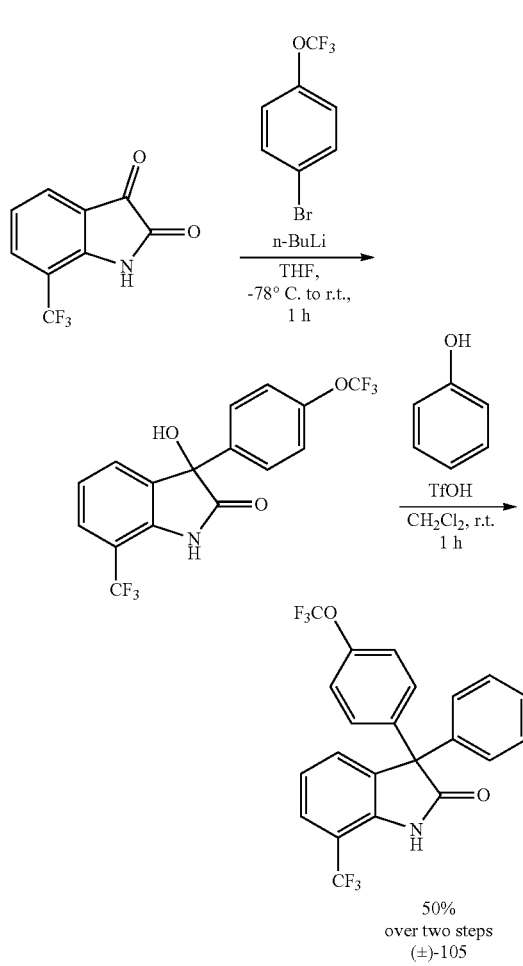

50% over two steps
(±)-105

Synthesis of 3-(4-hydroxyphenyl)-3-(4-(trifluoromethoxy)phenyl)-7-(trifluoromethyl)indolin-2-one ((±)-105): A round bottom flask was charged with 1-bromo-4-(trifluoromethoxy)benzene (3.08 mmol) and dissolved in THF (3.0 mL). The reaction mixture was cooled to −78° C. and a solution of n-BuLi (2.77 mmol, 1.7 mL) added dropwise over 10 minutes. The reaction was stirred for 1 hour. In another flask, the desired isatin (1.54 mmol) was added and dissolved in THF (9.4 mL). This solution of isatin was added to the reaction vessel dropwise over 10 minutes. The resultant mixture was stirred at −78° C. for 1 hour, warmed to r.t., and then stirred for 1 hour. The reaction was quenched with water (10 mL). The solution was extracted with ethyl acetate (3×) and the combined organic layers were dried over sodium sulfate, filtered, and concentrated in vacuo. A new round bottom flask was charged with crude tertiary alcohol and phenol (6.95 mmol) and dissolved in dichloromethane (7.7 mL). The reaction mixture was then placed in an ice bath and triflic acid (TfOH, 0.7 mL) was then added dropwise. The reaction vessel was removed from the ice bath and stirred at room temperature for 1 hour. The reaction mixture was then poured into an ice-filled sodium bicarbonate and the aqueous solution was extracted with ethyl acetate (3×). The combined organic layers were dried over sodium sulfate, filtered, and concentrated in vacuo. The resultant oil was then purified via column chromatography. (±)-105 was isolated in 50% yield over two synthetic steps.

$^1$H NMR (CD$_3$OD, 500 MHz) δ: 7.54 (d, J=7.95 Hz, 1H), 7.45 (d, J=7.48 Hz, 1H), 7.31 (d, J=8.91 Hz 2H), 7.22 (m, 3H), 7.03 (d, J=8.85 Hz, 2H), 6.75 (d, J=8.80 Hz, 2H).

$^{13}$C NMR (CD$_3$OD, 188 MHz) δ: 181.35, 158.37, 149.81 (q, J=1.78 Hz), 142.17, 139.84 (q, J=2.29 Hz), 136.92, 132.65, 131.22, 131.06, 130.48, 126.12 (q, J=4.58 Hz), 125.15 (q, J=270.89 Hz), 123.55, 121.88 (q, J=255.84 Hz), 122.01, 116.48, 113.77 (q, J=33.32 Hz), 62.22.

HRMS (ESI): m/z calc. for C$_{22}$H$_{14}$NO$_3$F$_6$ [M+H]$^+$ 454.0878, found: 454.0878.

Figure 5:
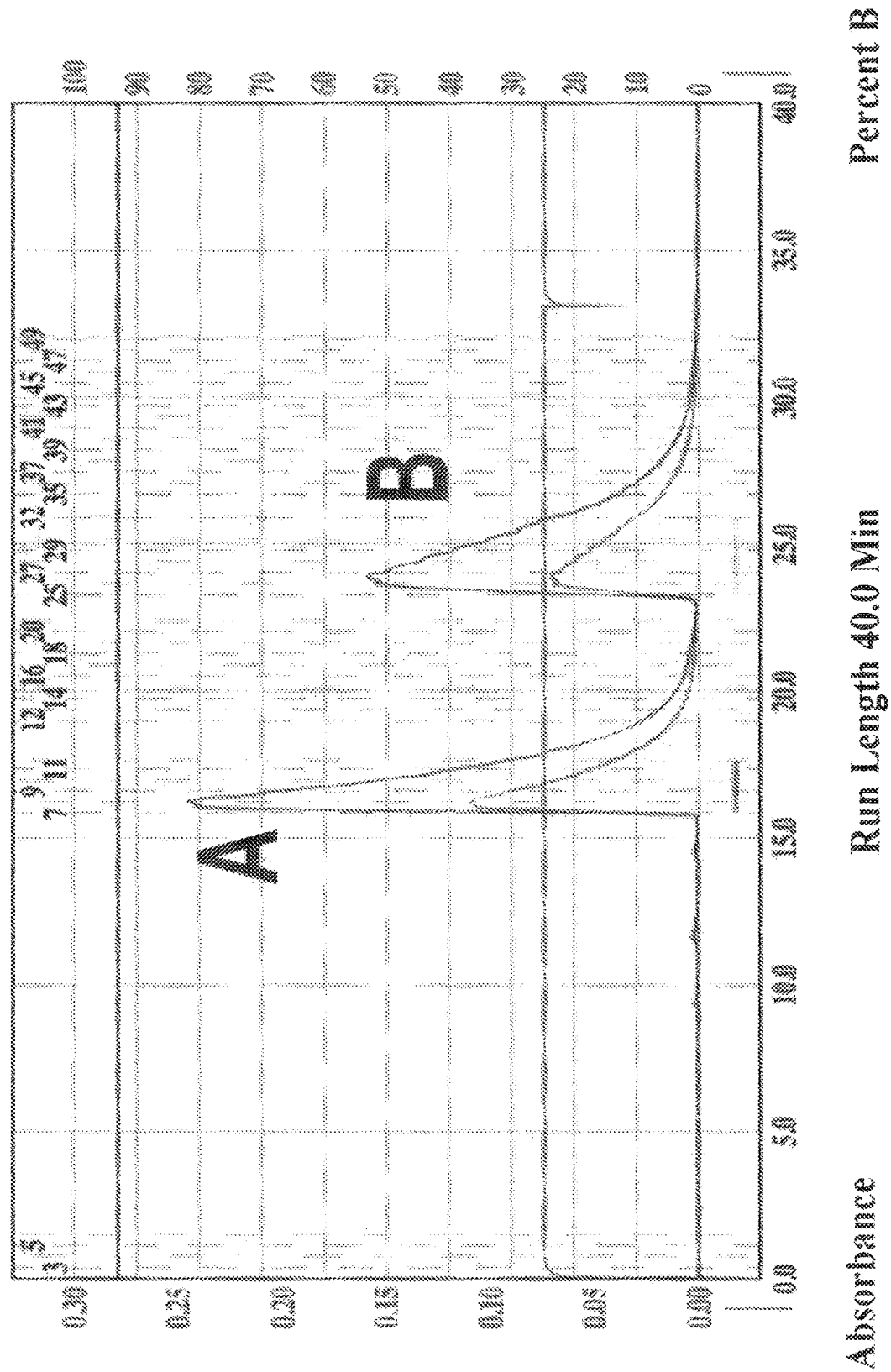
FIG. 5. Chiral separation of (±)-105 showing resolution of individual enantiomers.
Figure 6:
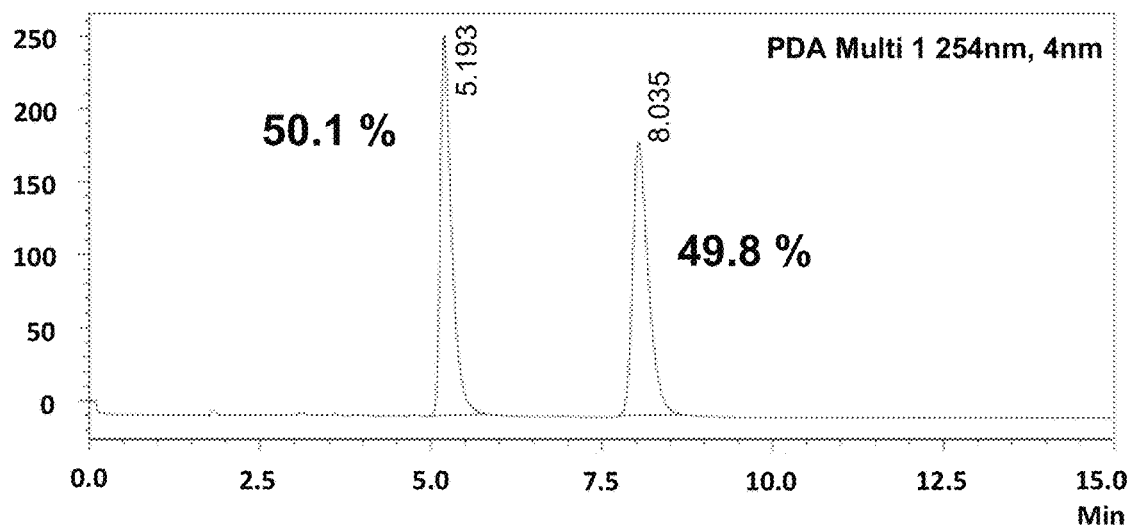
FIG. 6. (±)-105 chiral HPLC trace showing resolved peaks.
Figure 7:
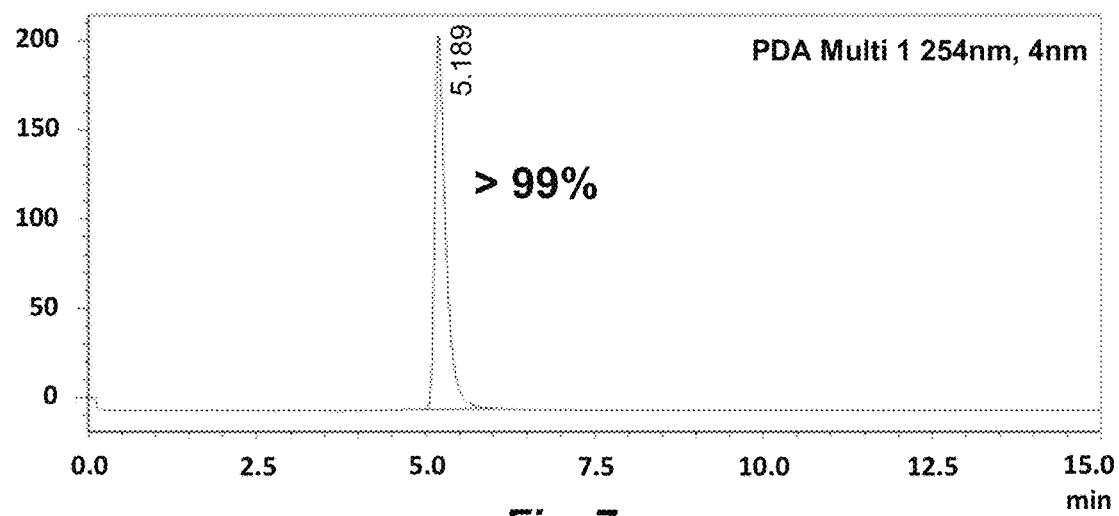
FIG. 7. (−)-105 Chiral HPLC trace of isolated enantiomer.
Figure 8:
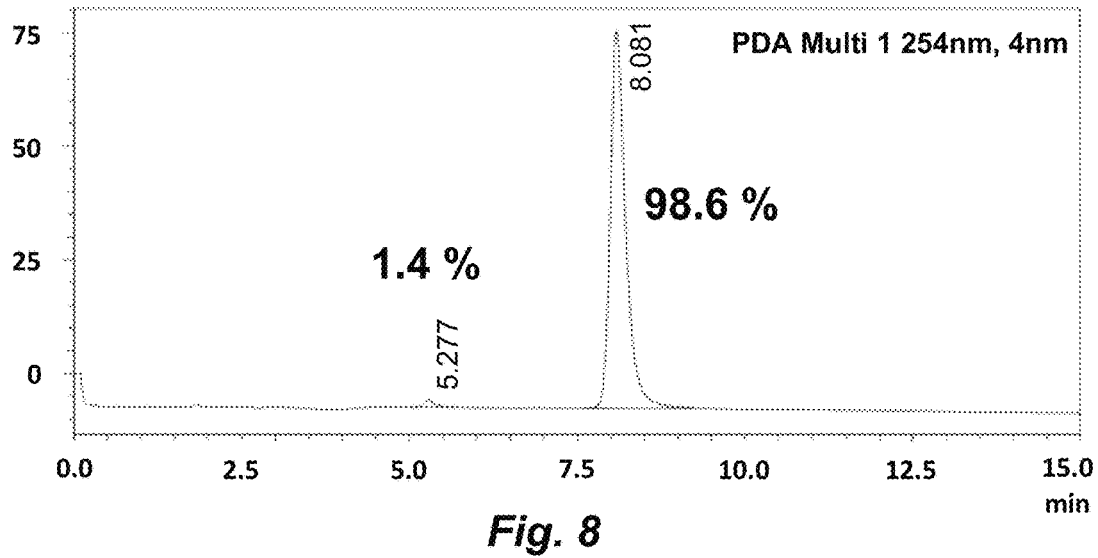
FIG. 8. (+)-105 Chiral HPLC trace of the other isolated enantiomer.

Chiral Separation of (±)-105: (±)-105 was separated into its respective enantiomers using preparative chiral HPLC separation (Lux® 5 μm Cellulose-1, LC Column, 250×21.2 mm, AXIA™ Packed, isocratic: 7% i-PrOH/hexanes). Collected fractions yielded (−)-105 (peak A) and (+)-105 (peak B): FIG. 5. This method of chiral separation yields (−)-105 as a white solid (enantiomeric purity=>99%, $^{589}$[α]$_{CHCl3}$=−14.6° (±0.1°)) and (+)-105 as a white solid (enantiomeric purity=~98-99%, $^{589}$[α]$_{CHCl3}$=+13.8° (±0.1°)) (see Example 4). Enantiopurity determination was conducted by analytical chiral HPLC column: CHIRALPAK® IB-3 (particle size 3 μm, dimensions: 4.6 mm×100 mm, separation method, isocratic 7.5% i-PrOH/hexanes) (FIG. 6-8).

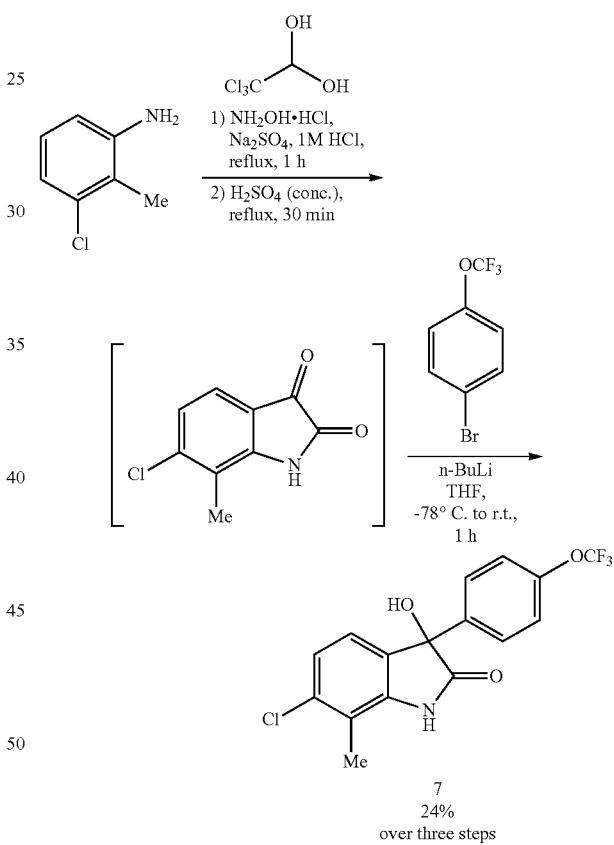

7
24%
over three steps 6-chloro-3-hydroxy-7-methyl-3-(4-(trifluoromethoxy)phenyl)indolin-2-one (7): A reaction vessel was charged with substituted aniline (2.82 mmol), 1M HCl (2.82 mL), water (18.8 mL), anhydrous sodium sulfate (16.92 mmol), and hydroxylamine hydrochloride (9.17 mmol). The mixture was heated to boiling and then chloral hydrate was added as one portion. The reaction was kept at reflux for 40 minutes, then cooled to reflux and the aqueous solution was extracted with ethyl acetate (3×). The combined organic layers were dried over sodium sulfate, filtered, and concentrated in vacuo. Concentrated sulfuric acid (3 mL) was then added to the resultant residue. This solution was heated to 80° C. for 20 minutes, then poured onto ice. The resulting aqueous mixture was extracted with ethyl acetate (3×), and the combined organic layers dried over sodium sulfate, filtered, and concentrated in vacuo. The red-brown solid obtained after concentration proved to be poorly soluble in most organic solvents.

To a new reaction vessel, the desired phenyl bromide (3.08 mmol) was added and dissolved in THF (3.0 mL). The reaction mixture was cooled to −78° C. and a solution of n-BuLi (2.77 mmol, 1.73 mL) added dropwise over 10 minutes. The reaction was stirred for 1 hour. In another flask, 6-chloro-7methylisatin (1.54 mmol) was added and dissolved in THF (9.4 mL). This solution of isatin was added to the reaction vessel dropwise over 10 minutes. The resultant mixture was stirred at −78° C. for 1 hour, warmed to r.t., and then stirred for 1 hour. The reaction was quenched with water (10 mL). The solution was extracted with ethyl acetate (3×) and the combined organic layers were dried over sodium sulfate, filtered, and concentrated in vacuo. The resulting oil was run through a silica plug (elution solvent gradient: 10% EtOAc/Hexanes ramped to 100% EtOAc).

7 was isolated in 24% yield over three synthetic steps. $^1$H NMR (CD$_3$OD, 500 MHz) δ: 7.46 (d, J=8.85 Hz 2H), 7.23 (d, J=7.98 Hz, 2H), 7.10 (d, J=7.97 Hz 1H), 6.98 (d, J=8.02 Hz, 1H), 2.35 (s, 3H).

$^{13}$C NMR (CD$_3$OD, 188 MHz) δ: 181.25, 150.17 (q, J=1.83 Hz), 143.14, 140.98, 136.68, 132.74, 128.63, 124.53, 124.40, 121.88 (q, J=255.75 Hz), 121.86, 119.76, 78.91, 14.11.

HRMS (ESI): m/z calc. for C$_{16}$H$_{11}$NO$_3$F$_3$ClNa [M+Na]$^+$ 380.0277, found: 380.0284.

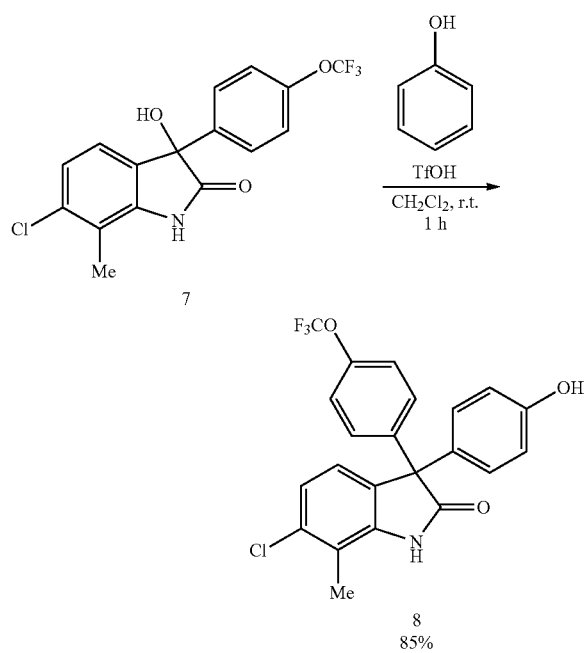

6-chloro-3-(4-hydroxyphenyl)-7-methyl-3-(4-(trifluoromethoxy)phenyl)indolin-2-one (8): Utilizing General Procedure C, 8 was isolated in 85% yield. $^1$H NMR (CD$_3$OD, 500 MHz) δ: 7.30 (d, J=8.91 Hz 2H), 7.21 (m, 2H), 7.10 (d, J=8.10 Hz, 1H), 7.02 (m, 4H), 6.73 (d, J=8.80 Hz, 2H), 2.35 (s, 3H).

$^{13}$C NMR (CD$_3$OD, 188 MHz) δ: 181.81, 158.16, 149.67 (q, J=2.02 Hz), 142.6, 142.38, 135.34, 133.50, 133.10, 131.18, 130.47, 125.48, 124.12, 121.89 (q, J=255.49 Hz), 121.8, 119.66, 116.35, 63.45, 14.30.

HRMS (ESI): m/z calc. for C$_{22}$H$_{16}$NO$_3$F3Cl [M+H]$^+$ 434.0771, found: 434.0764.

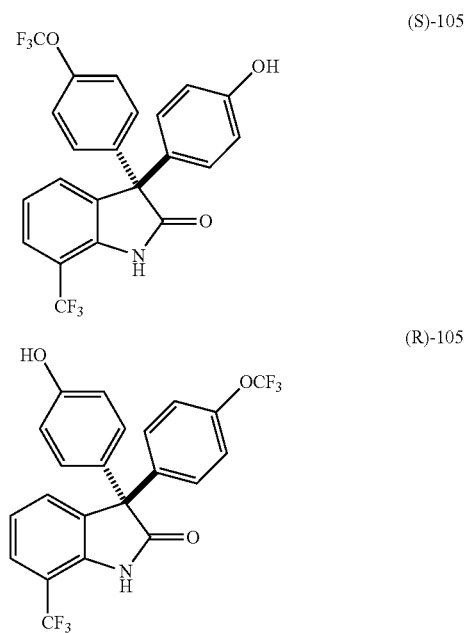

Separation of enantiomers of 105: Racemic mixtures of 105 were separated into respective enantiomers (FIG. 5) using preparative chiral HPLC separation (Lux® 5 μm Cellulose-1, LC Column, 250×21.2 mm, AXIA™ Packed, isocratic: 7% i-PrOH/hexanes). Collected fractions yielded (−)-105 (peak A) and (+)-105 (peak B) This method of chiral separation yields (−)-105 as a white solid (enantiomeric purity=>99%, [α]=−134) and (+)-105 as a white solid (enantiomeric purity=98->99%, [α]=not determined). Enantiopurity determination was conducted by analytical chiral HPLC column: CHIRALPAK® IB-3 (particle size 3 μm, dimensions: 4.6 mm×100 mm, separation method, isocratic 7.5% i-PrOH/hexanes). The compound (−)-105 bends light in the negative direction ([α] value). FIG. 6 is a quantitative chiral HPLC trace showing the separated peaks of (±)-105 that are present in about equal concentrations. FIG. 7 shows the active (−)-105 peak is highly pure after separation. FIG. 8 shows the inactive (+)-105 peak is also pure after separation. Because there is a trace of the active (−)-105 in this preparation, and because of the outstanding potency of (−)-105, at extremely high concentrations (+)-105 may exhibit some activity.

Example 2. Cancer Cell Death Studies of Compound 105

Experimental Details of the Xenografts: TYS-Luc cells (5,000,000 cells in Matrigel) were injected into the upper mammary fat pad of ovariectomized female NSG (SCID) mice (Jackson labs). After 10 weeks, on day 0, large tumors (size range: 100-600 mm$^3$) were present. Mice were treated with the vehicle used to dissolve (−)-105, or (−)-105 at 40 mg/kd daily by subcutaneous injection. For bioluminescent imaging (BLI) of the tumors, the mice were anesthetized with isoflurane and Lucerfin, the luciferase substrate, was injected into the mice. Flux, the total member of light photons hitting the detector in one second was measured using an IVIS (In Vitro Imaging System). Shown is the flux (in millions of units per second) for the entire area containing each tumor, or an equivalent area when the tumor is tiny or undetectable and the percent change in tumor size at each time a measurement was taken (day 0, day 3, week 1, week 2, week 3). Then treatment was stopped, and another measurement was taken two weeks letter. Note that tumors were also measured with calipers. Since some tumors do not protrude much, this is far less accurate than BLI. After three days all the (−)-105 tumors has declined to undetectable using calipers.

Figure 1:
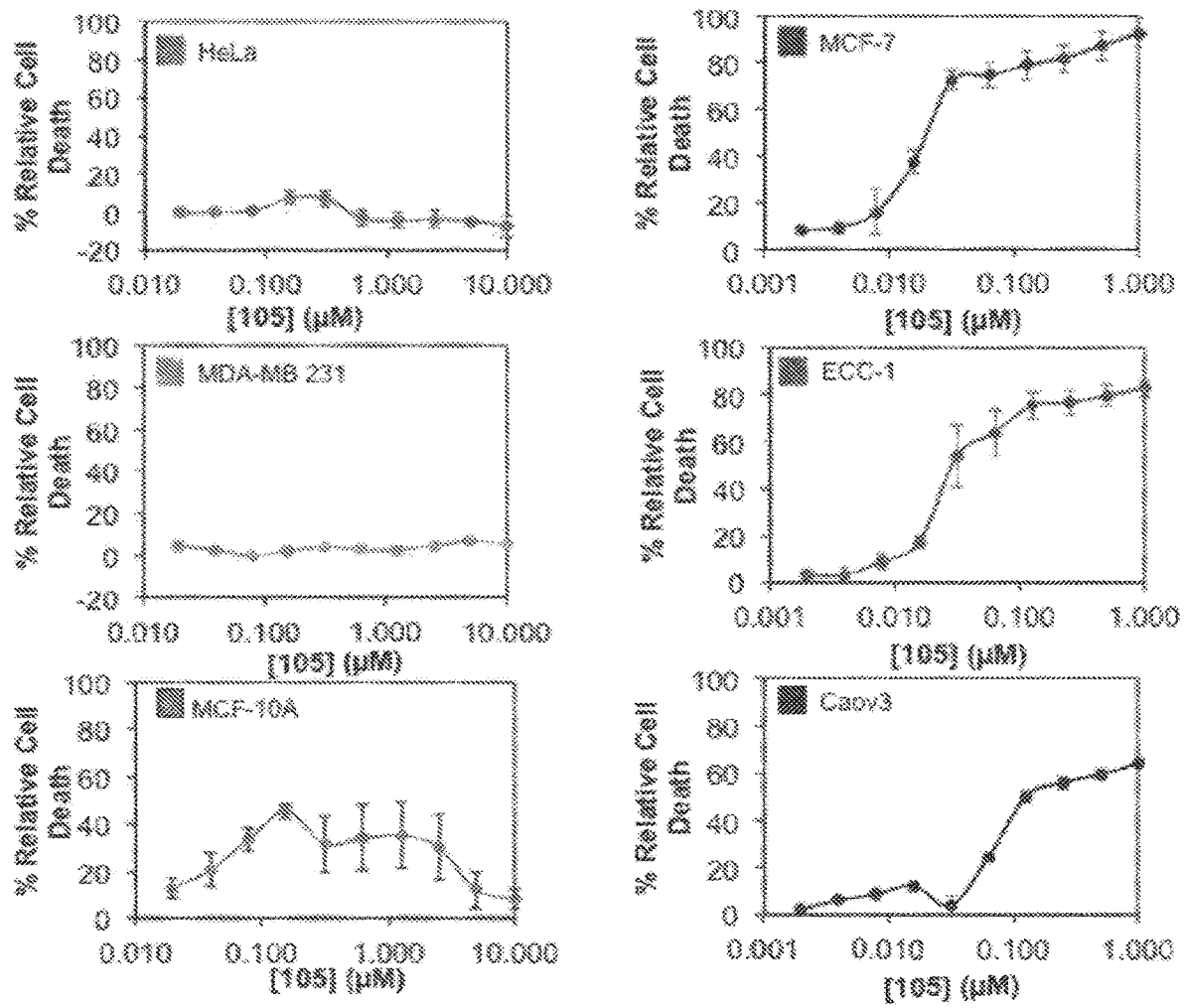
FIG. 1. Dose response study of the effect of (±)-105 on ERα positive and ERα negative human cancer cells. Alamar blue 24-hour death assay was used to determine $IC_{50}$ of compound 105.

FIG. 1 shows the dose response effect of (±)-105 on ERα positive and ERα negative human cancer cells, demonstrating anticancer activity. ERα positive MCF-7 breast cancer, Caov-3 ovarian cancer and ECC-1 uterine cancer cells and ERα negative MDA-MB-231 human breast cancer cells and HeLa, human cervical carcinoma cells and MCF-10A human mammary epithelial cells were plated at 10,000 cells/well (96 well plate) in 50 µl of medium. After about 18 hours, an additional 50 µl of medium containing 2× the desired final concentration of the test compound (C-105) was added to each well (final vol. 100 µl/well). After 24 hours Alamar Blue reagent was added and fluorescence in the wells was read after 1 hour (BMG PheraStar Microplate Reader). % relative death was determined by setting the reading for 10,000 nM raptinal-treated cells to 100% dead cells and the reading for vehicle-treated cells to 0% dead cells. (Data is the average±SEM of 3 independent experiments with 5 biological replicates for each sample within each independent experiment.)

Figure 2:
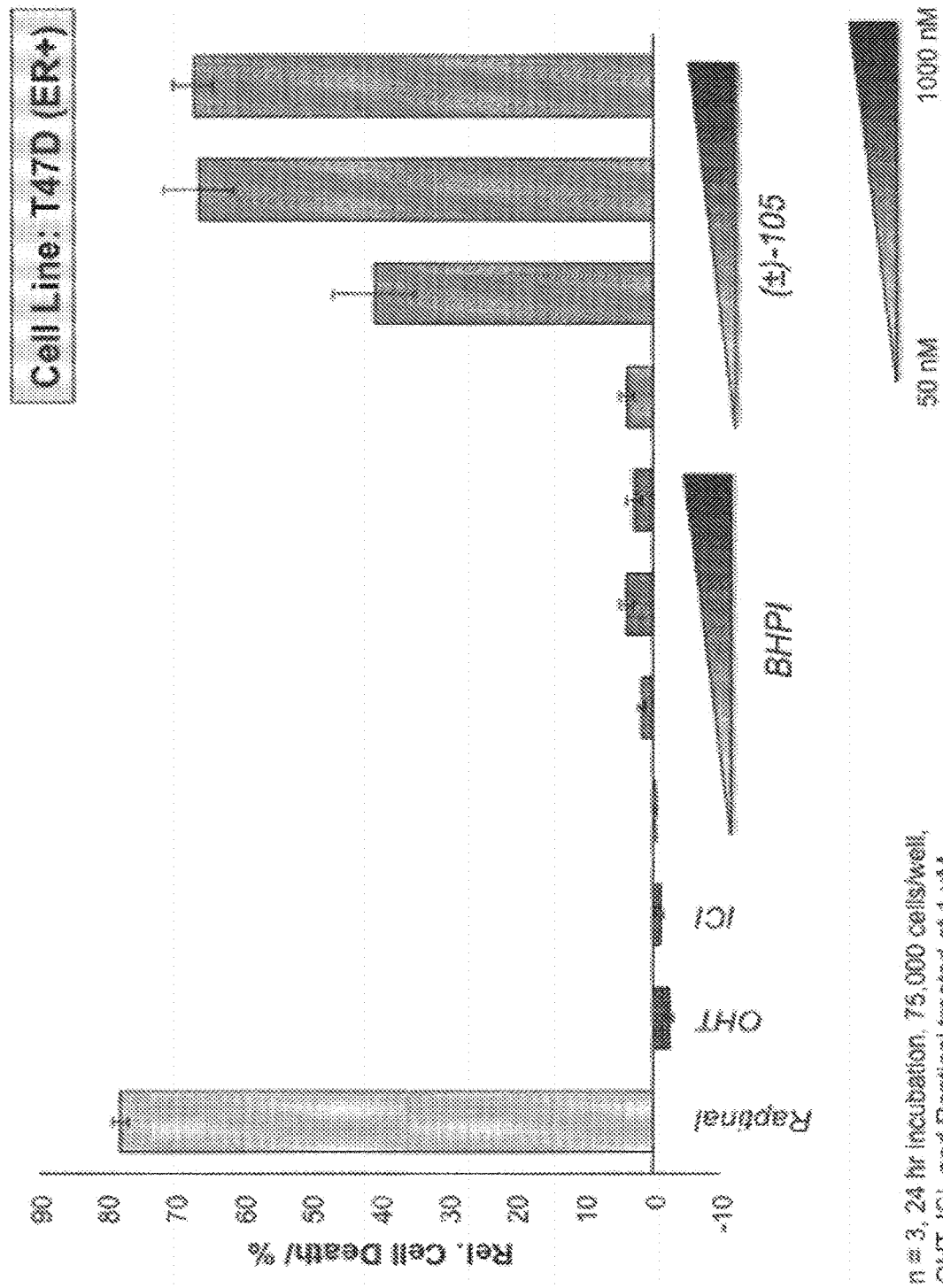
FIG. 2. Dose response study comparing the ability of BHPI and (±)-105 to kill ERα positive T47D cells. Compound (±)-105 potently induces breast cancer cell death.
Figure 36:
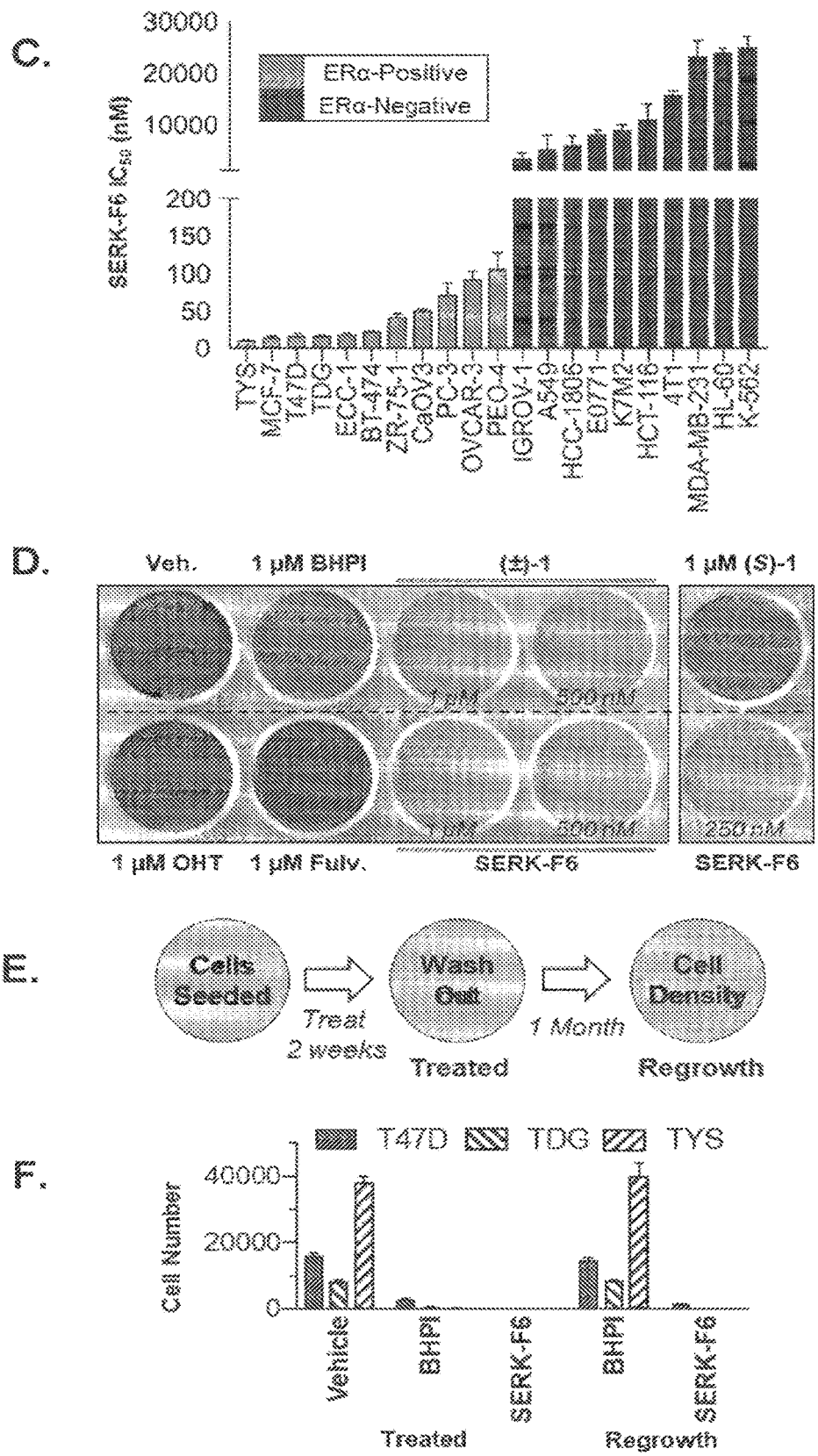
FIG. 36. Discovery of SERK-F6 (also known as, C(−)-105, (−)-105, (R)-105, (−)-1, or (R)-1), a compound that kills ERα-positive cancer cells. a, Chemical structures of BHPI and racemic compound 1 (i.e. (±)-1), and their cytotoxic activity on T47D breast cancer cells after 24-hour incubations with concentrations as indicated in nM. Cells were stained with annexin V-FITC and PI dyes prior to analysis via flow cytometry. Error bars represent S.E.M of 3 independent replicates. b, SERK-F6 is cytotoxic to ERα-positive cell line, MCF-7, but has minimal effects against ERα-negative cell line, MDA-MB-231. Cells were incubated with SERK-F6 or positive control, Raptinal, for 24 hours and then stained with annexin V-FITC and PI dyes and analyzed via flow cytometry. Error bars represent S.E.M of 3 independent replicates. c, $IC_{50}$ values of SERK-F6 after 24-hour incubation against a panel of cancer cell lines grouped by their reported ERα status. Cell viability was measured by Alamar blue fluorescence and set relative to a vehicle control and a quantitative dead control treated with Raptinal. Error bars represent S.E.M of 3 independent experiments. d, Crystal violet staining of T47D cells after 24-hour incubations with compounds and concentrations as indicated. Image is representative of 2 independent experiments. e,f, Long-term cell culture experiment with T47D, TDG, and TYS cells. Cells were incubated for 2 weeks with compounds (1 µM), followed by compound washout, and cells were cultured for 2 months. Cell number was determined by MTS.

FIG. 2 shows the dose response comparing the ability of BHPI and (±)-105 to kill ERα positive T47D cells. T47D, human breast cancer cells were plated at 75,000 cells/well. The next day, DMSO vehicle, 10 µM raptinal (control for 100% cell death), or 0, 50, 100, 500 and 1,000 nM of BHPI or (±)-105, or 1,000 nM ICI/fulvestrant or 1,000 nM OHT was added. After 24 hours viable cells were determined by FACS using annexin V-FITC and propidium iodide dyes. (n=3 independent experiments ±SEM). Results from this flow cytometry experiment (that detects dead cells) show that (±)-105 is cytotoxic and not cytostatic. Whereas compounds OHT, ICI and BHPI are all cytostatic based on low observed activity. The observed activity of (±)-105 in this assay is similar to the positive control, raptinal, a compound that also quantitatively kills cancer cells (see also FIG. 36A).

Figure 3:
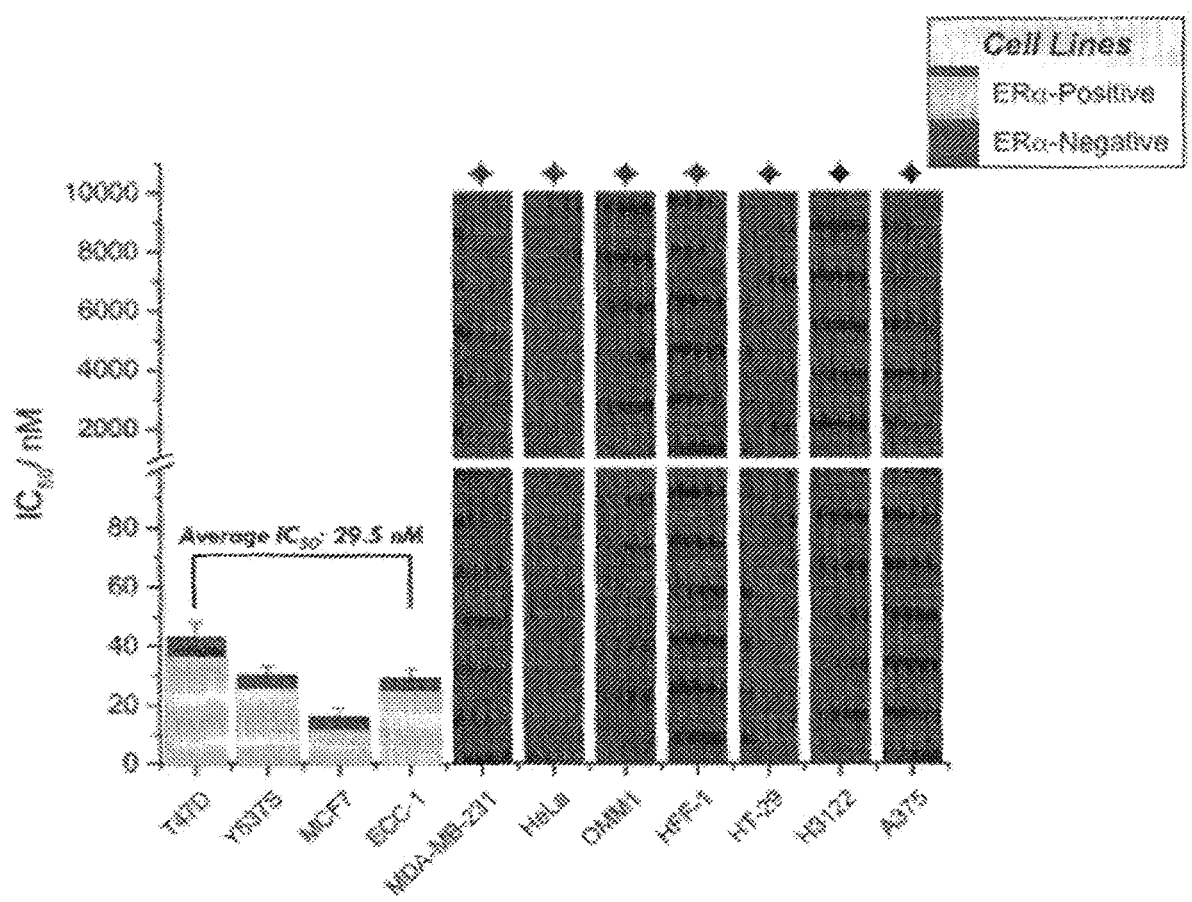
FIG. 3. Comparison of the ability of (±)-105 to kill ERα positive cells and its inability to kill ERα negative cells.

FIG. 3 compares the ability of (±)-105 to kill ERα positive and ERα negative cells. The dose response tests the ability of (±)-105 to rapidly kill ERα positive and ERα negative cells. Cell lines: ERα positive breast cancer: T47D, MCF-1 TYS (Y537S); Endometrial: ECC-1; ERα negative cell lines: Breast MDA-MB-231; Melanoma: OMM1, A375; Lung: H3122; Colon: HT-29; fibroblast: HFF-1. 4,000-8,000 cells/well were plated. The next day (±)-105 at concentrations from 0-10,000 nM was added. After 24 hours Alamar Blue reagent was added and fluorescence in the wells was read. % relative death was determined by setting the reading for 1,000 nM raptinal-treated cells to 100% dead cells and the reading for vehicle-treated cells to 0% dead cells. (n=3±SEM). These results show that racemic compound 105 is selective for ERα positive cancer cell lines; also demonstrated with enantiomerically pure (−)-105 in FIG. 36F.

Figure 4:
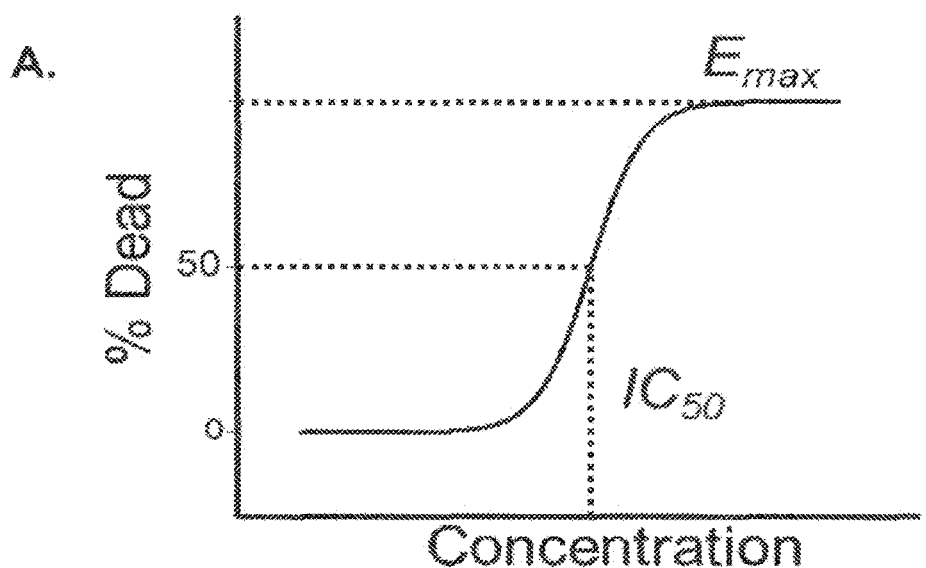
FIG. 4. (−)105 Potently and Quantitatively Kills Cancer Cells. MCF7 (ER+) cells, 24 hour incubation, read out via Alamar Blue Fluorescence, Dead Control: Raptinal, n=3 (A, B). (−)-105 is effective when administered orally (C). Orthotopic Mouse Xenograft breast cancers of TYS cells, Visualization by bioluminescent imaging. Treatment: 40 mg/kg daily (−)-105 for 3 days either by oral gavage or by intraperitoneal injection.
Figure 4:
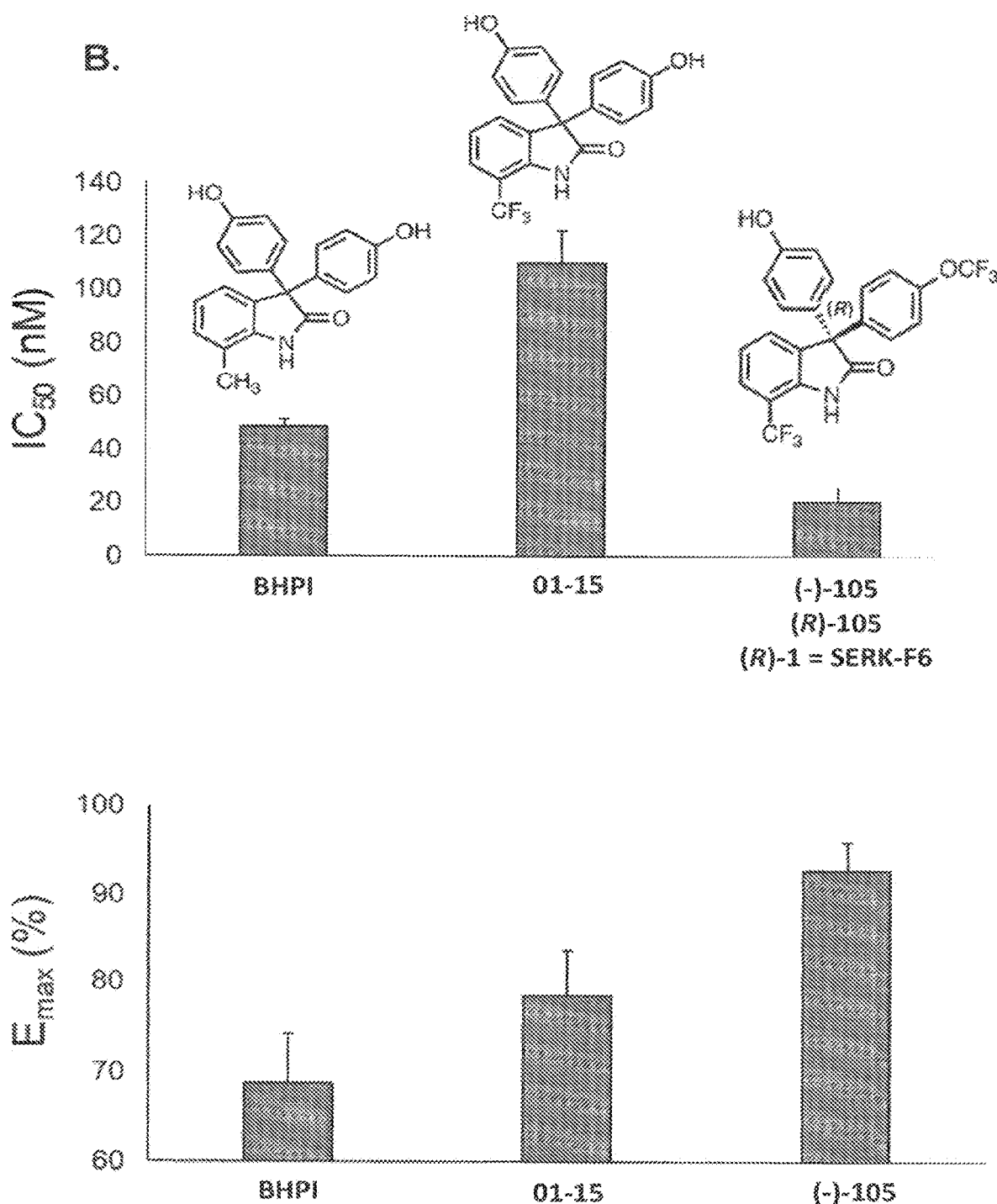
Figure 4:
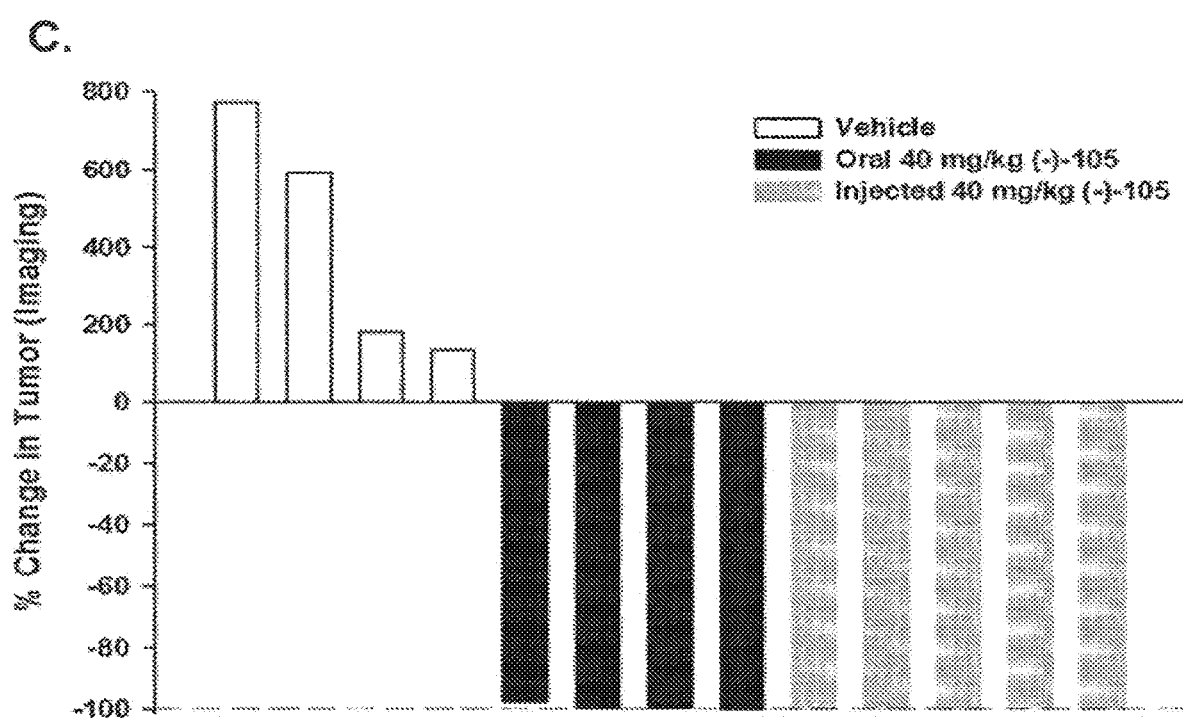

FIG. 4A illustrates how $IC_{50}$'s for cell death were determined. 4B tests the ability BHPI, (−)-105, and 01-15 to kill. 4C shows (−)-105 is effective when administered orally. Large orthotopic breast tumors of TYD-Luc cells (T47DERα D538G-luciferase human breast cancer cells) were allowed to form for 4 months in immune suppressed NSG mice. Mice were treated for 3 days with either vehicle only (Vehicle), oral gavage of 40 mg/kg (−)-105 (oral), or daily injection of 40 mg/kg (−)-105 (injected). Tumors were visualized by bioluminescent imaging using luciferase. The dashed line represents −100%; tumor regression to undetectable. Thus, the result show (−)-105 is superior to BHPI and 01-15.

Figure 9:
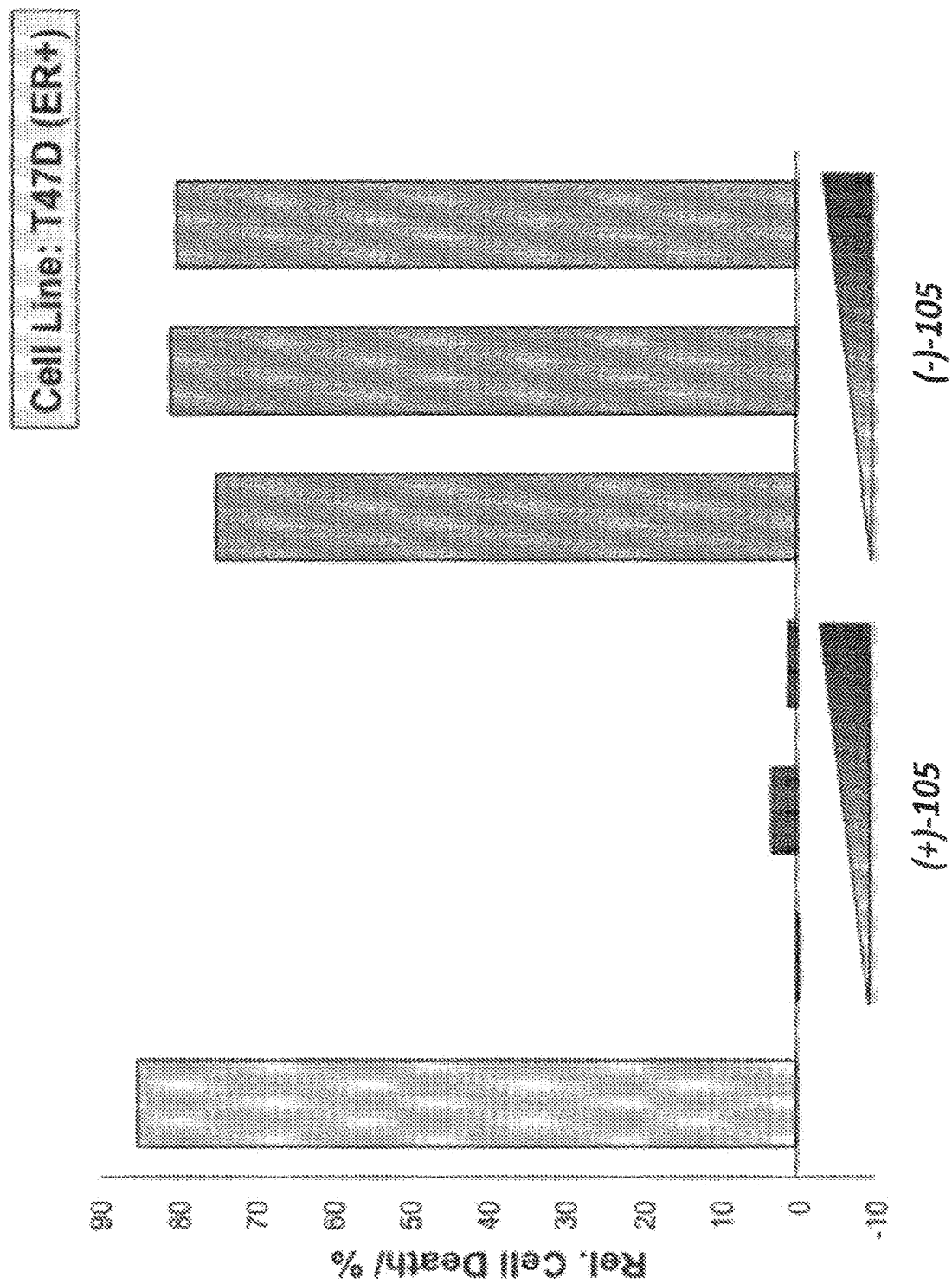
FIG. 9. The (−) enantiomer of 105 is active and the (+) enantiomer is inactive in T47D cell line.

FIG. 9 shows that the (−) enantiomer of 105 is active and the (+) enantiomer is inactive. 75,000 ERα positive T47D, human breast cancer cells, were plated/well. The next day, DMSO vehicle, 10 µM raptinal (control for 100% cell death), or 100. 500 and 1,000 nM of (+)-105, or (−)-105 was added. After 24 hours viable cells were determined by FACS using annexin V-FITC and propidium iodide dyes. (n=1).

Figure 10:
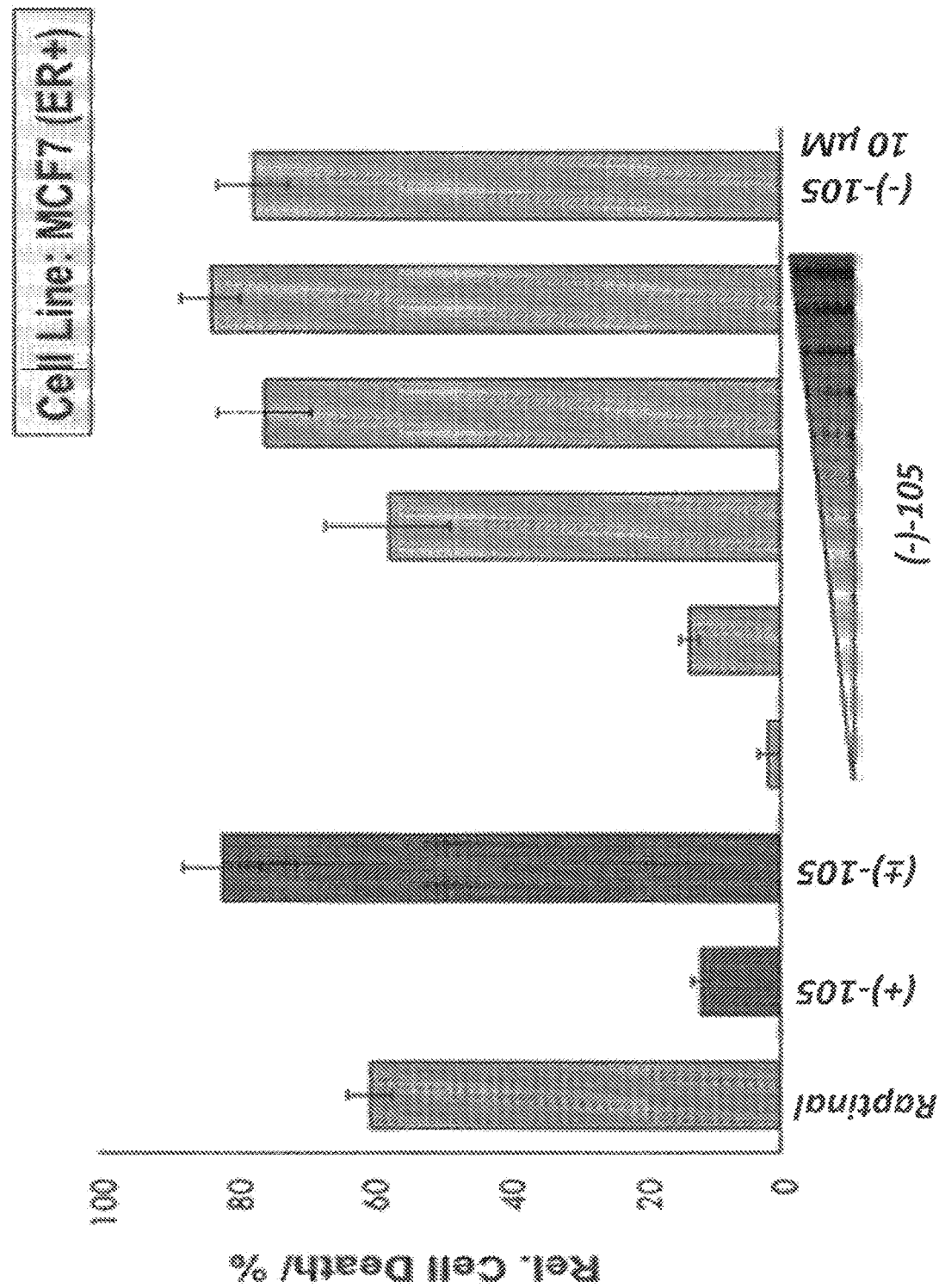
FIG. 10. (−)-105 induces dose-dependent death of MCF-7 cells; (+)-105 is inactive.

FIG. 10 shows that (−)-105 induces dose-dependent death of MCF-7 cells; (+)-105 is inactive.

Figure 11:
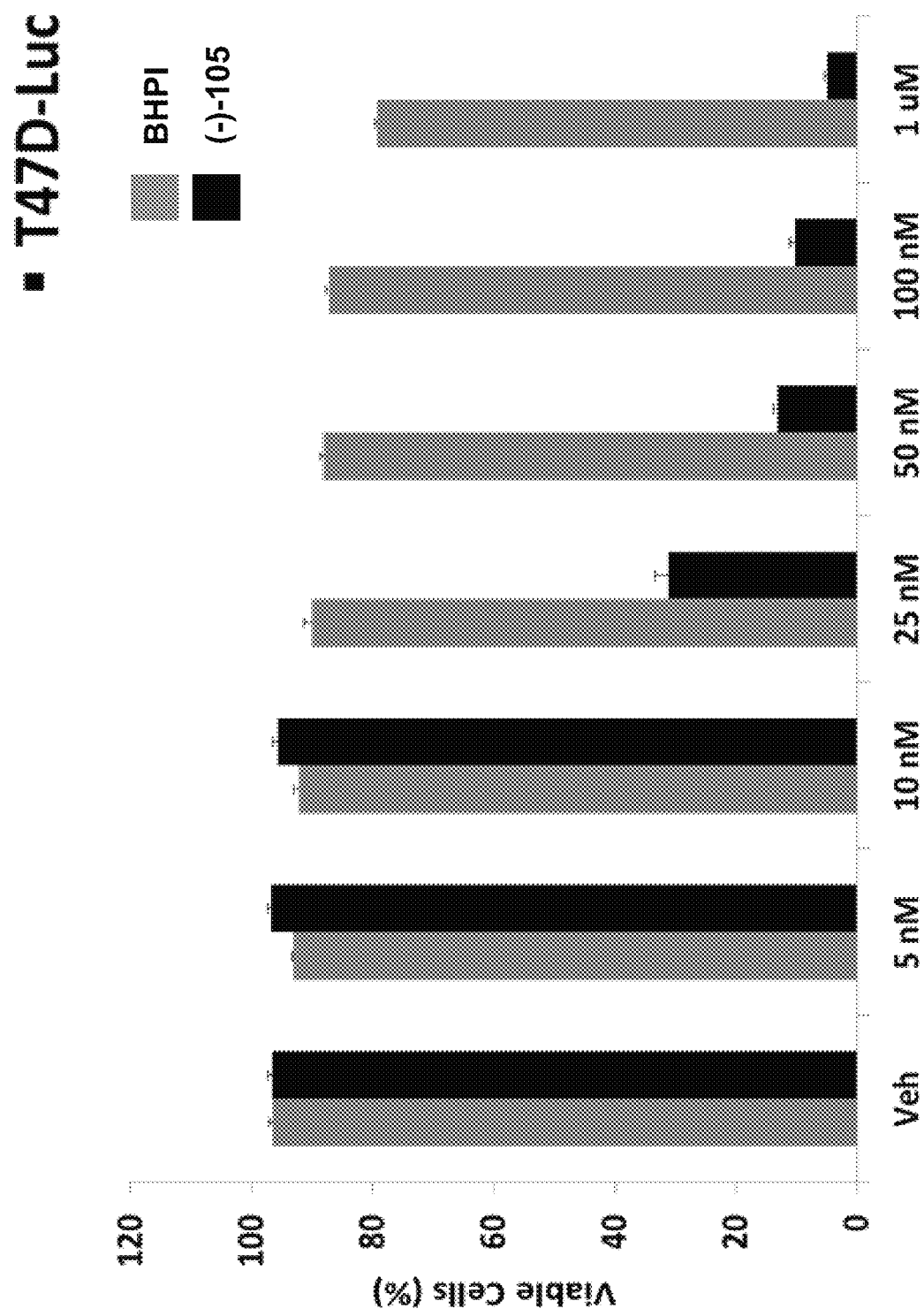
FIG. 11. Dose response study shows (−)-105 is superior to BHPI for killing of T47D cells.

FIG. 11 shows the dose response for killing of T47D-Luc cells by BHPI and by the active (−)-105 enantiomer of C-105. The Trypan Blue cell death assay was used to compare the ability of the active (−) enantiomer of C-105 and BHPI to kill estrogen receptor a (ERα) positive T47D, human breast cancer cells expressing luciferase (T47D-Luc cells). 300,000 T47D-Luc cells/well in 10% FBS were plated in a 6-well plate in triplicate. 24 hours after plating, the indicated concentrations of the active (−) enantiomer of C-105 [(−)-105] or BHPI, or vehicle [Veh] were added to the cells. After 24 hours, the cells were harvested, and the % dead cells was determined by automated Trypan Blue exclusion using the Countess II automated hemocytometer. Percentage of viable cells was calculated by doing 100−(Cell Death %). (n=3±SEM).

Figure 12:
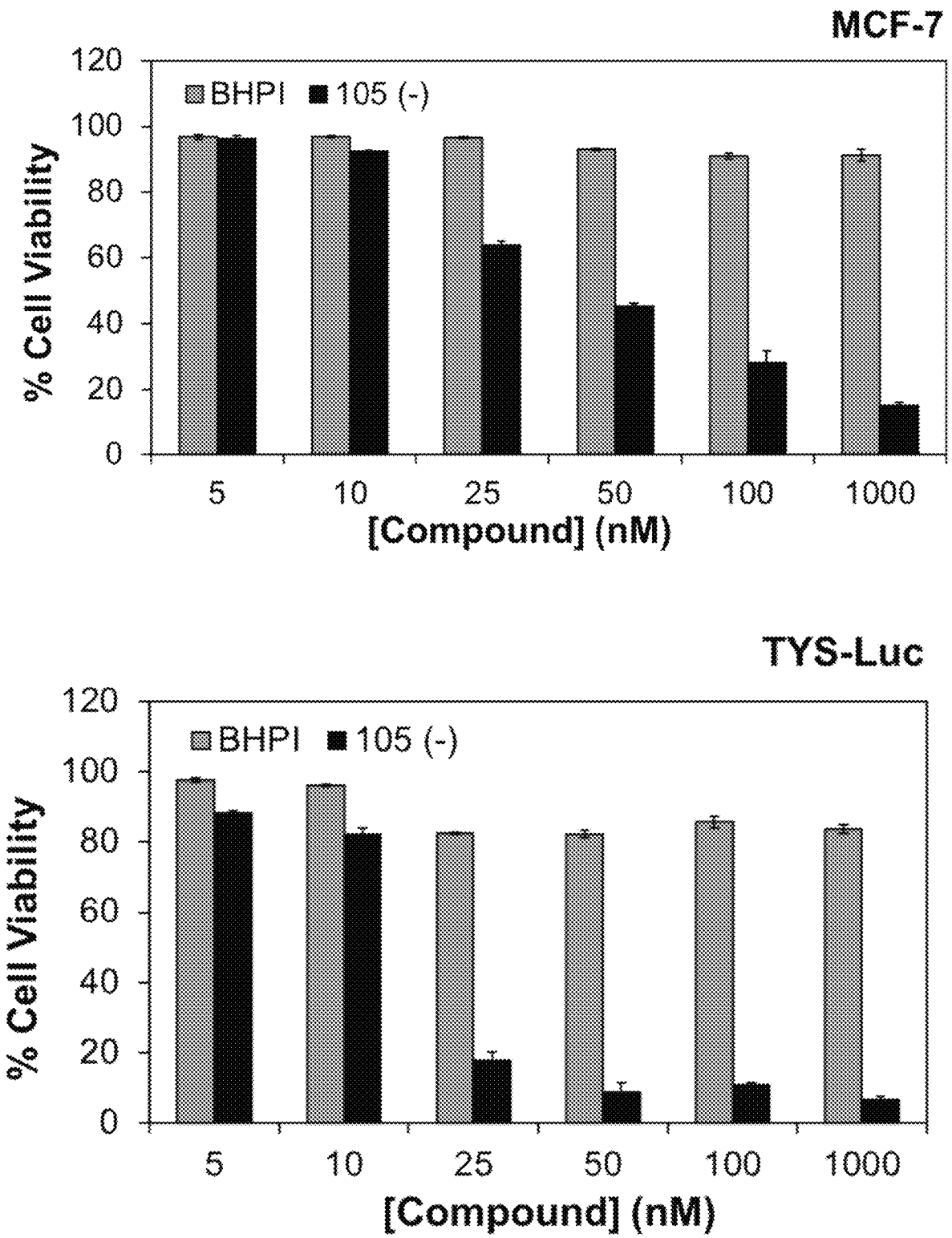
FIG. 12. Dose Response Study shows (−)-105 is superior to BHPI in killing MCF-7 and TYS cells.

FIG. 12 shows the dose response of (−)-105 is superior to BHPI in killing MCF-7 and TYS-Luc cells. The Trypan Blue cell death assay was used to evaluate the ability of the active enantiomer of 105 (−) [(−)-105] to kill ERα positive MCF-7 and TYS-Luc, human breast cancer cells. 300,000 T47D cells/well in 10% FBS were plated in a 6-well plate in triplicate. 24 hours after plating, the indicated concentrations of BHPI, or the active enantiomer 105 (−) of C-105 [(−)-105] was added. After 24 hours, the cells were harvested, and the % dead cells was determined by automated Trypan Blue exclusion using the Countess II automated hemocytometer. Percentage of viable cells was calculated by doing 100−(Cell Death %). (n=3±SEM).

FIG. 13 shows the dose response study of (−)-105 is superior to BHPI and current endocrine therapies in killing TDG-Luc cells. In the top figure, the dose response shows that (−)-105 is superior to BHPI in killing TDG-Luc cells. The lower left figure shows current endocrine therapies, ICI/Fulvestrant/Faslodex and z-4-hydroxytamoxifen (the active form of tamoxifen) do not kill TDG-Luc Cells. The Lower right figure shows the (+)-105 enantiomer is inactive and does not kill TDG-luc cells. The Trypan Blue cell death assay was used to evaluate the ability of the active enantiomer of C-105 [(−)-105] to kill ERα positive TDG-Luc cells. For all studies, 300,000 TDG-Luc cells/well in 10% FBS were plated in a 6-well plate in triplicate. 24 hours after plating, the indicated concentrations the active enantiomer of (−)-105, or BHPI (top) ICI, or OHT (Lower left) or (+)-105 (lower right) were added. After 24 hours, the cells were harvested, and the % dead cells was determined by automated Trypan Blue exclusion using the Countess II automated hemocytometer. Percentage of viable cells was calculated by doing 100−(Cell Death %). (n=3±SEM).

Figure 14:
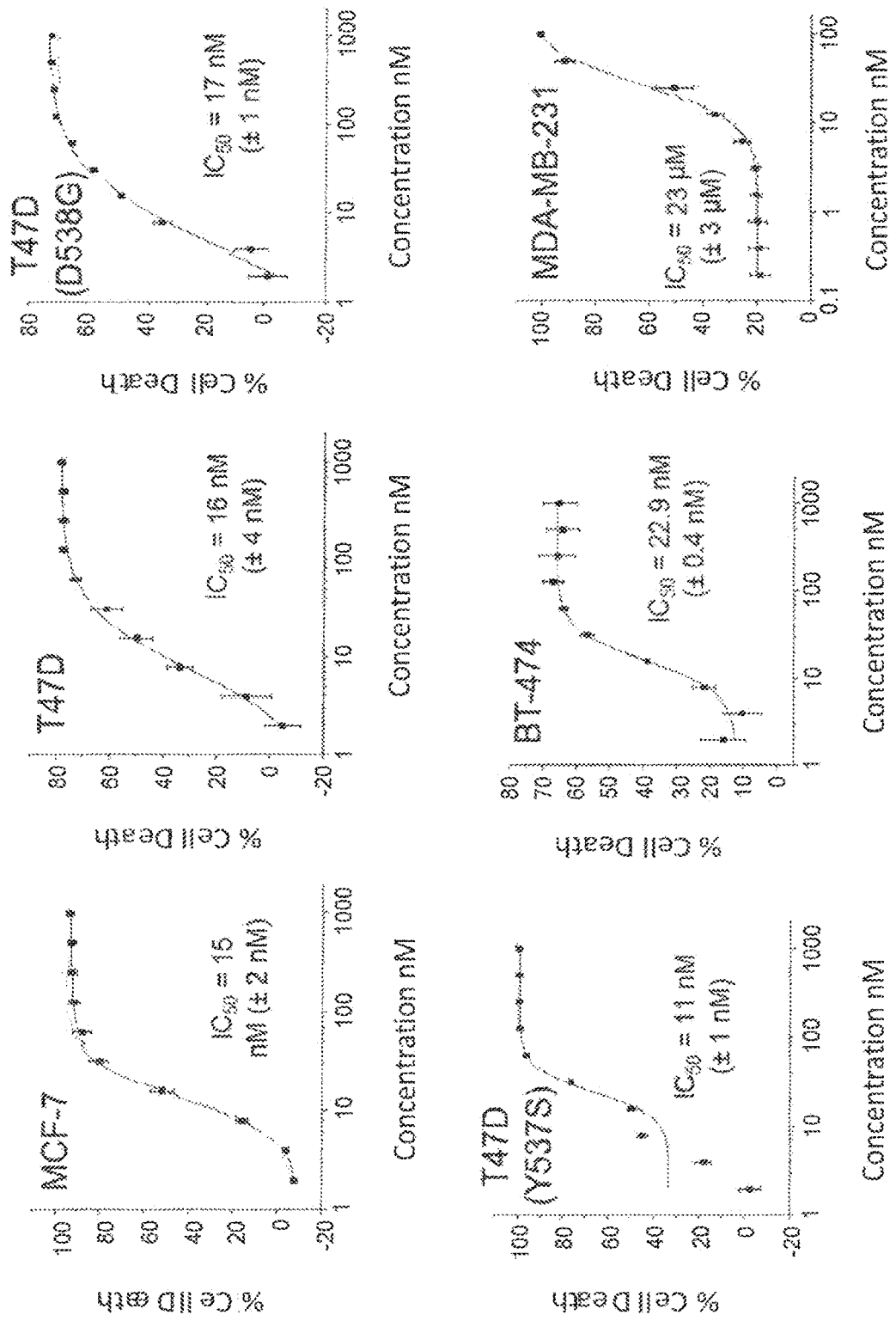
FIG. 14. Dose response studies to determine $IC_{50}$'s for killing of cancer cells by (−)-105.

FIG. 14 shows the IC$_{50}$s for killing of cancer cells by (−)-105. Cell lines: ERα positive breast cancer: T47D, MCF-7 TYS (T47D Y537S) TDG (T47D D538G), BT-474; ERα negative MDA-MB-231 breast cancer cells; 6,000 cells/well were plated (96 well plate) in 100 μl of medium. DMSO Conc. was adjusted to 1% in each well. (−)-105 at concentrations from 0-100,000 nM was added. After 24 hours Alamar Blue reagent (10 μl of 0.1 mg/ml) was added. After 2-4 hours fluorescence in the wells was read ($\lambda_{ex}$: 555 nm, $\lambda_{em}$: 585 nm, Spectra Max M3 Plate reader). % relative death was determined by setting the reading for 10,000 nM raptinal-treated cells to 100% dead cells and the reading for vehicle-treated cells to 0% dead cells. (n=3±SEM).

Figure 15:
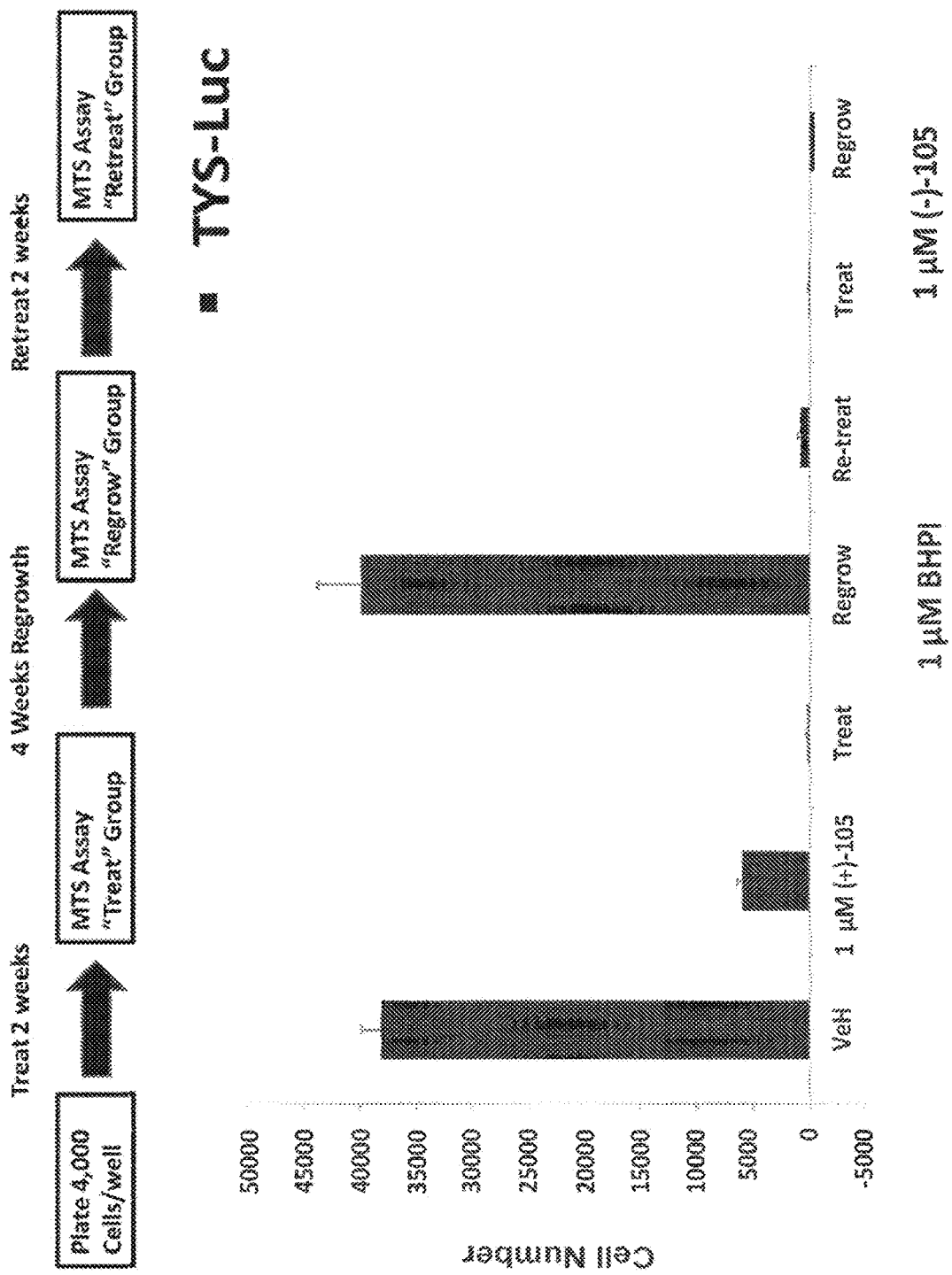
FIG. 15. In long-term experiments (−)-105, but not BHPI, kills 100% of TYS-Luc cells.

FIG. 15 shows long-term experiments wherein (−)-105, but not BHPI, kills 100% of TYS-Luc cells. To simulate the effect of several weeks of treatment of a tumor in a mouse xenograft, long-term cell culture experiments were performed. TYS-Luc cells (T47DERαY537S-Luc cells; ERαY537S is the most lethal ERα mutation seen in metastatic breast cancer) were plated at 4,000 cells/well in 96 well plates. Cells were initially maintained for 2 weeks in medium containing either DMSO vehicle, 1 μM inactive (+) enantiomer of C-105, 1 μM BHPI, or 1 μM of the active (−) enantiomer of C-105 (Treat). After 2 weeks (medium change every 2 days) cell number was determined using MTS and a standard curve of absorbance versus cell number for TYS-Luc cells. Notes: (i)Bars denote the BHPI and (−)-105 arms of the experiment. No drug is present during regrow. (ii) Because absorbance values are extremely low, the MTS assay cannot accurately quantitate fewer than 200 cells/well (iii) After separation, the inactive enantiomer still contains ~1-2% active enantiomer; thus, it retains some activity when used at the high conc. of 1,000 nM), Another set of similarly treated wells was not assayed with MTS and after 4 washes with PBS was placed in estrogen-free medium containing 10% cd-FBS for 4 weeks (medium change every 2 days) (Regrow). This allows any surviving cells to regrow. After 4 weeks the cells were assayed using MTS. Notably, there was no regrowth of cells treated with active (−)C-105 and robust regrowth of BHPI-treated cells. (Note: Visual inspection of the wells confirmed that there were no cells in the well treated for 2 weeks with active (−)-105.) To test whether the cells that regrew after BHPI treatment were resistant to BHPI they were re-treated for another cycle (BHPI Retreat) and shown to retain sensitivity to BHPI killing. (n=8 biological replicates ±SEM.

Figure 16:
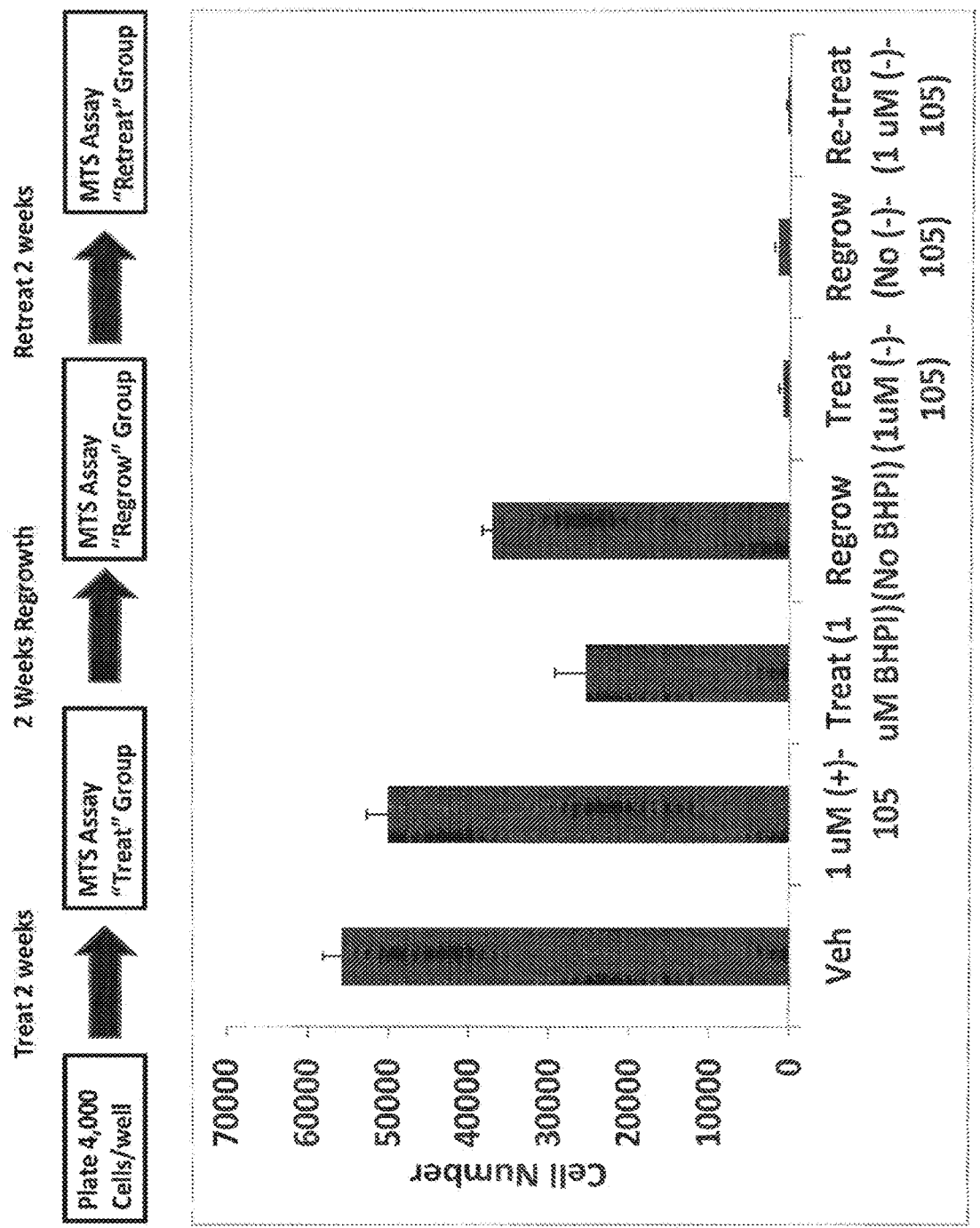
FIG. 16. In Long-term experiments that simulate therapy, (−)-105, but not BHPI, eradicates, lethal, therapy resistant breast cancer cells.

FIG. 16 shows long-term experiments that simulate therapy, wherein (−)-105, but not BHPI, eradicates, lethal, therapy resistant breast cancer cells. Cells: MCF-7Y537S (MCF-7 ERα Y537S-luciferase (derived from MCF-7 human breast cancer cells. MCF-7 cells are the most widely line of human breast cancer cells. This is the most lethal and second most common mutation in metastatic breast cancer.) Experimental conditions are as in the legend to FIG. 15. (+)-105 enantiomer was inactive.

Figure 18:
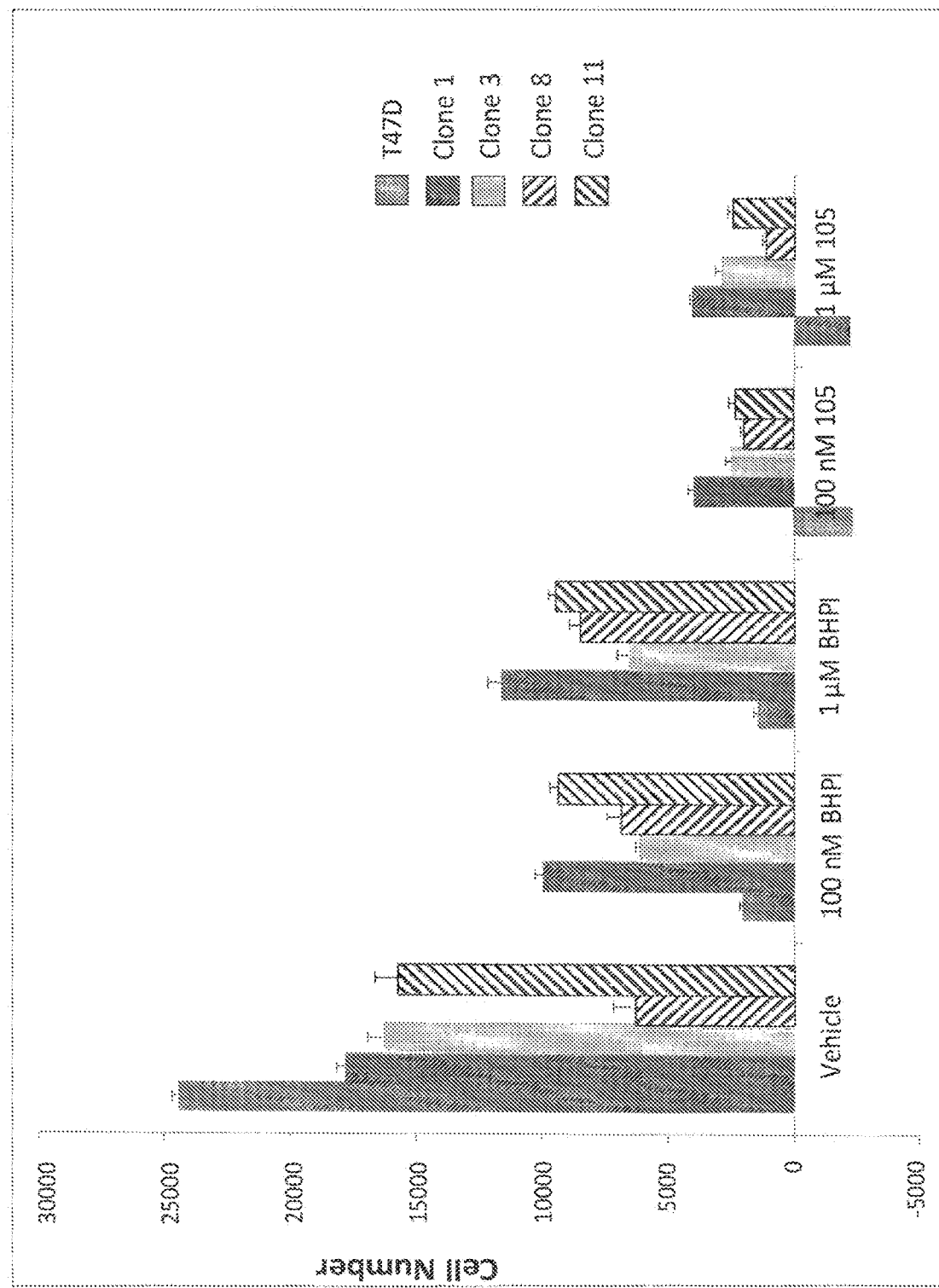
FIG. 18. (−)-105 kills breast cancer cells resistant to killing by BHPI.

FIG. 18 shows (−)-105 kills breast cancer cells resistant to killing by BHPI. ERα containing T47D human breast cancer cells able to survive in 1 μM BHPI were selected by clonal outgrowth. The effect of 100 nM and 1 μM BHPI and (−)-105 on growth of the (BHPI-sensitive) parental T47D cells and partially BHPI-resistant T47D clones 1,3,8, and 11 was evaluated. 4,000 cells/well were plated. Cell number was determined by MTS assay from a standard curve of absorbance versus cell number. Conclusions: BHPI blocked growth and killed many of the T47D cells and (−)-105 killed all the T47D cells. BHPI inhibited growth but could not stop growth of the resistant clones; (−)-105 completely blocked the growth of the resistant clones and reduced their cell numbers below the original cell number of 4,000 cells/well. Thus, in 4 days (−)-105 killed some, but not all, of the resistant cells.

Figure 19:
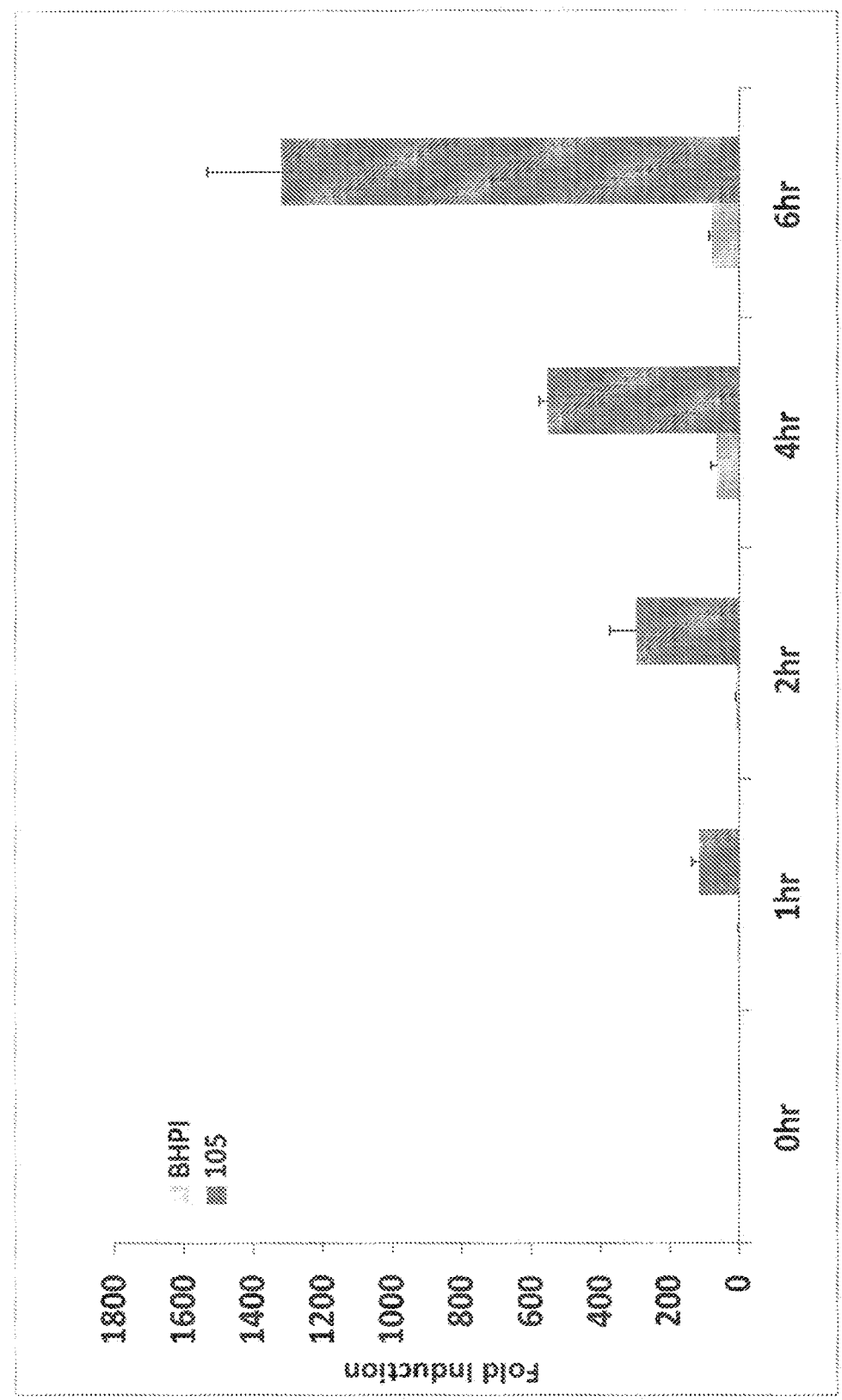
FIG. 19. (−)-105 potently activates the UPR as shown by induction of spliced XBP-1 mRNA.

Concerning the mechanism of action of (−)-105 for the anticipatory unfolded protein response (UPR), FIG. 19 shows (−)-105 potently induces formation of spliced XBP-1 mRNA. ERα positive T47D-luciferase, human breast cancer cells, were maintained for the indicated times in vehicle (Ctl, Control), 100 nM BHPI or 100 nM (−)-105. At the indicated times RNA was isolated and levels of sp-XBP1 mRNA quantitated by qRT-PCR. (n=3±SEM). (−)-105 or BHPI activation of the UPR activates the UPR sensor IRE1α, resulting in cleavage of inactive XBP1 mRNA to active spliced (sp)-XBP1 mRNA.

Increased sp-XBP1 mRNA is a widely used marker for unfolded protein response (UPR) activation. Thus, (−)-105 is a much stronger UPR hyper-activator and inducer of sp-XBP1 than BHPI.

Figure 20:
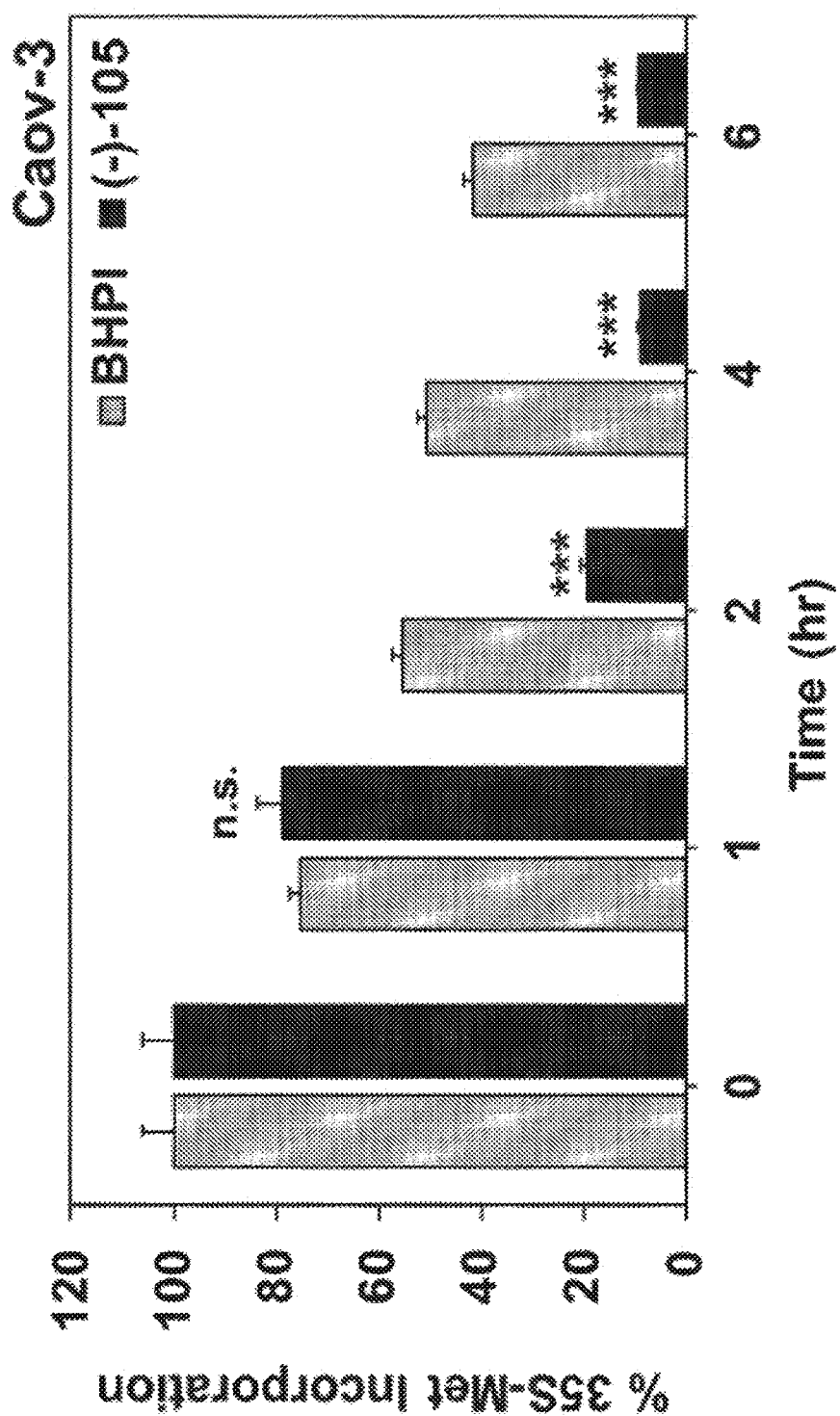
FIG. 20. (−)-105 is superior to BHPI in inhibiting protein synthesis in therapy-resistant Caov-3 ERα positive ovarian cancer cells.

FIG. 20 shows (−)-105, but not BHPI induces near-quantitative, inhibition of the synthesis of new proteins. ERα positive Caov-3, human ovarian cancer cells, were treated for the indicated times with 1,000 nM BHPI or 1,000 nM (−)-105. Cells were briefly labeled with $^{35}$S-methionine. Incorporation of labeled $^{35}$S-methionine into protein was determined by trichloroacetic acid precipitation and trapping of precipitated protein, but not free amino acids, in small Whatman hardened ashless filters. After solubilizing the protein in the filters with base and neutralization with acid, the samples were counted in a liquid scintillation counter. Shown is the average (n≥3) percent inhibition of protein synthesis compared to the 0-time sample. The near quantitative inhibition of protein synthesis by (−)-105 is consistent with (−)-105 inducing lethal hyperactivation of the PERK arm of the UPR. Even non-growing cells are constantly degrading protein and making new proteins. Cells in which nearly all (>90%) of protein synthesis is inhibited cannot grow and will ultimately die.

FIG. 21 shows blocking the efflux of calcium from the endoplasmic reticulum with 2-APB inhibits (−)-105-induced cancer cell death. ERα positive MCF-7 and TYS-Luc were treated with DMSO vehicle (Veh), or BHPI or (−)-105 plus or minus 2-APB for the indicated times. Cells death was determined using the instrument-based Trypan Blue exclusion assay. At 30 minutes, 2-APB nearly completely blocked (−)-105-induced cell death and at 45 and 60 min. it partially blocked cell death. This is consistent with (−)-105 inducing powerful lethal activation of the anticipatory UPR pathway. (n=3±SEM).

Figure 22:
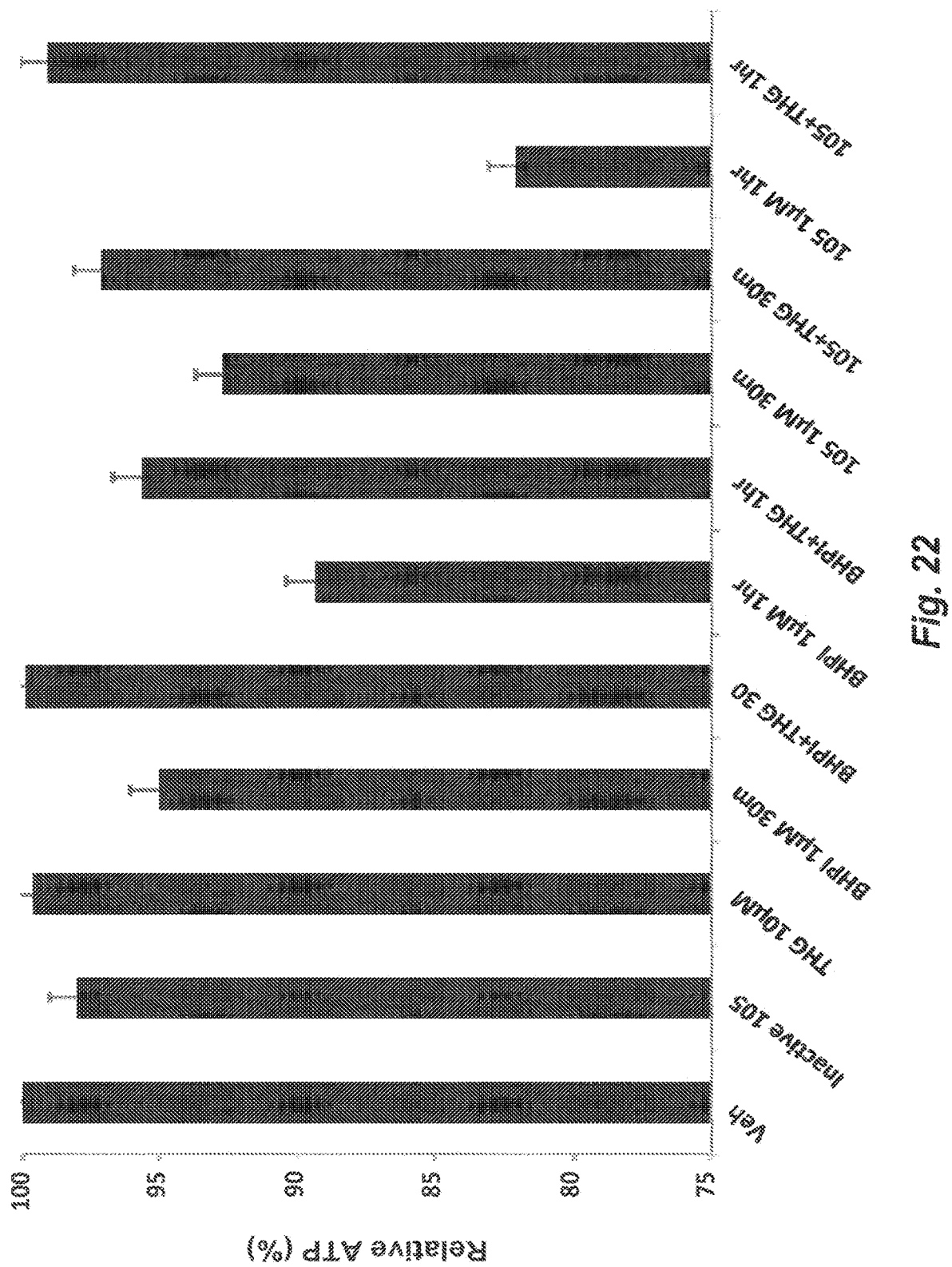
FIG. 22. (−)-105 reduces intracellular ATP levels; this reduction in ATP levels is blocked by inactivating the endoplasmic reticulum SERCA pump with thapsigargin.

FIG. 22 shows (−)-105 reduces intracellular ATP levels; this reduction in ATP levels is blocked by inactivating the SERCA pump with thapsigargin. TYS-Luc cells were maintained DMSO vehicle (Veh), 1,000 nM BHPI, 1,000 nM (−)-105 with and without 10,000 nM thapsigargin (THG) for the indicated times. ATP levels were determines using a kit and relative ATP levels were from a standard curve. Note that at 1 hr, THG completely blocked the (−)-105-induced decline in intracellular ATP levels. (n=3±SEM).

Figure 23:
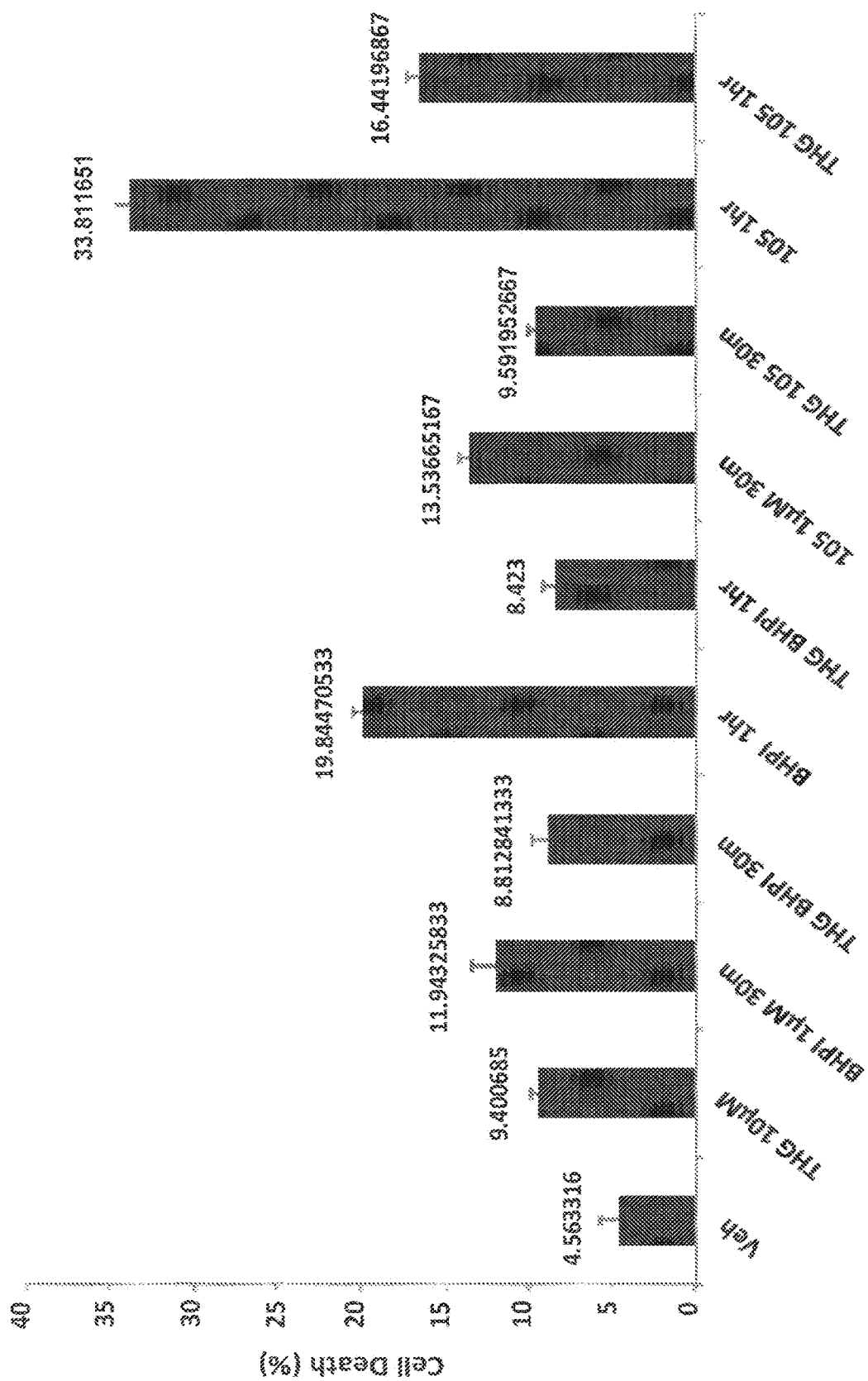
FIG. 23. Blocking the decline in ATP levels with thapsigargin inhibits (−)-105 induced cell death.

FIG. 23 shows blocking the decline in ATP levels with thapsigargin inhibiting (−)-105 induced cell deaths. TYS-Luc cells were maintained in DMSO vehicle (Veh) or BHPI, or (−)-105 with or without thapsigargin (THG) for the indicated times. Blocking the decline in ATP levels (FIG. 19) with THG inhibited (−)-105-induced cell death. Note that when THG was present, there was a strong inhibition of cell (−)-105-induced cell death at 1 hour. (n=3±SEM).

Example 3. Additional Data for Compounds Related to 105

Figure 24:
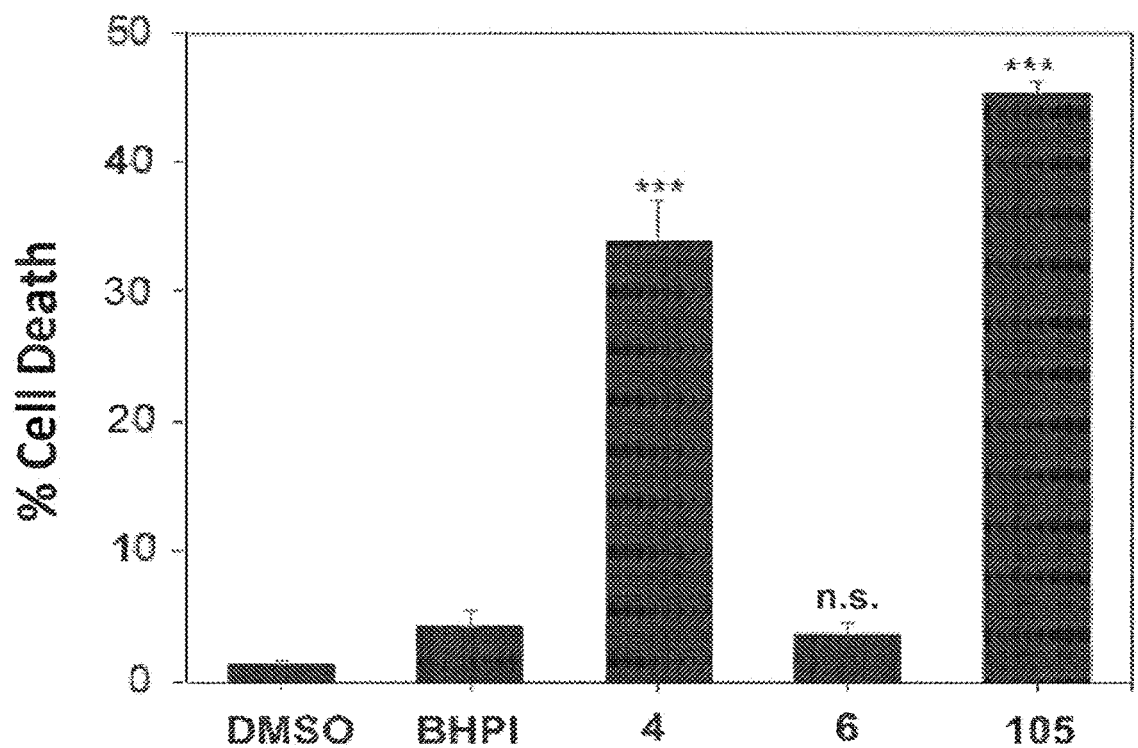
FIG. 24. Comparison of the ability of test compounds and BHPI to kill TDG cells.

FIG. 24 shows a comparison of the ability of test compounds and BHPI to kill TDG cells. TDG cells were incubated for 24 hours with 75 nM of BHPI or 75 nM of each of the indicated test compounds: 4, 6 and (±)-105 (enantiomers not separated). Cell death was determined using the instrument-based Trypan Blue exclusion assay. Structures are in the Synthesis section. Conclusion: Compared to BHPI, compounds 4 and 105 exhibit a greatly increased ability to kill the TDG cells. (n=3±SEM).

Figure 25:
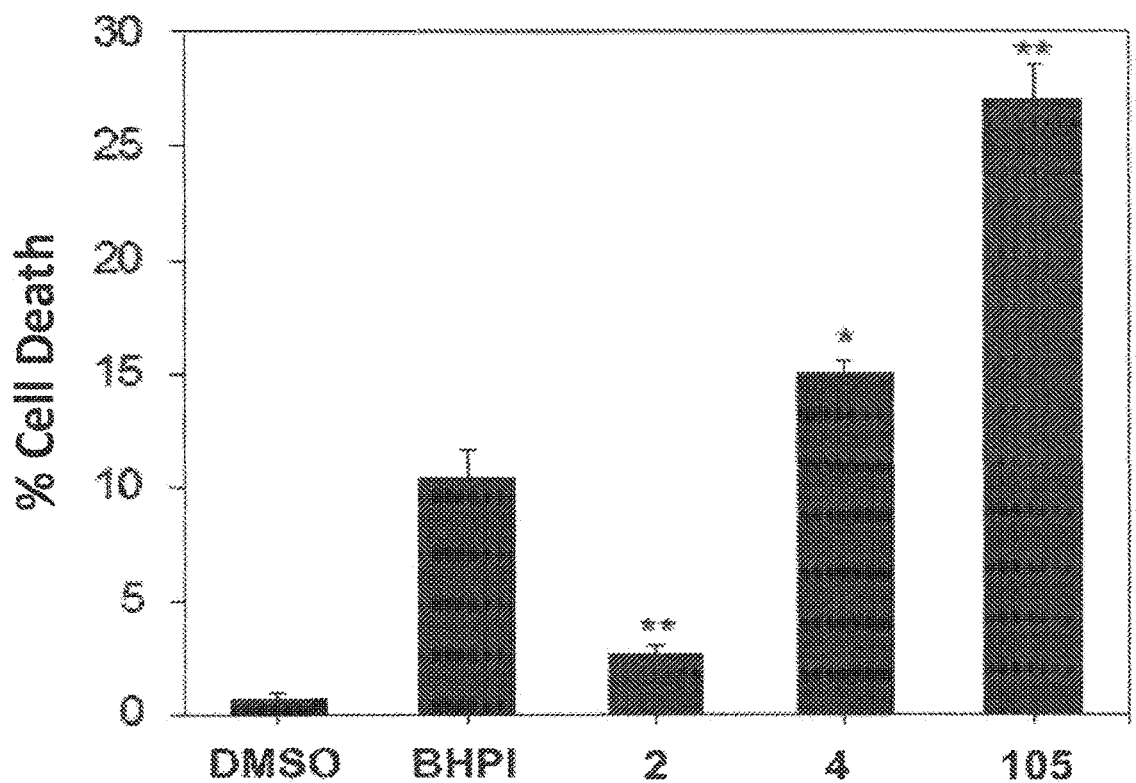
FIG. 25. Comparison of the ability of test compounds and BHPI to kill TYS cells.

FIG. 25 shows a comparison of the ability of test compounds and BHPI to kill TYS cells. TYS cells were incubated for 24 hours with 35 nM of BHPI or 35 nM of each of the indicated test compounds: 2, 4, and 105. Cell death was determined using the instrument-based Trypan Blue exclusion assay. (n=3±SEM). Thus, compared to BHPI, compounds 4 and 105 exhibit a greatly increased ability to kill the TYS cells.

Figure 26:
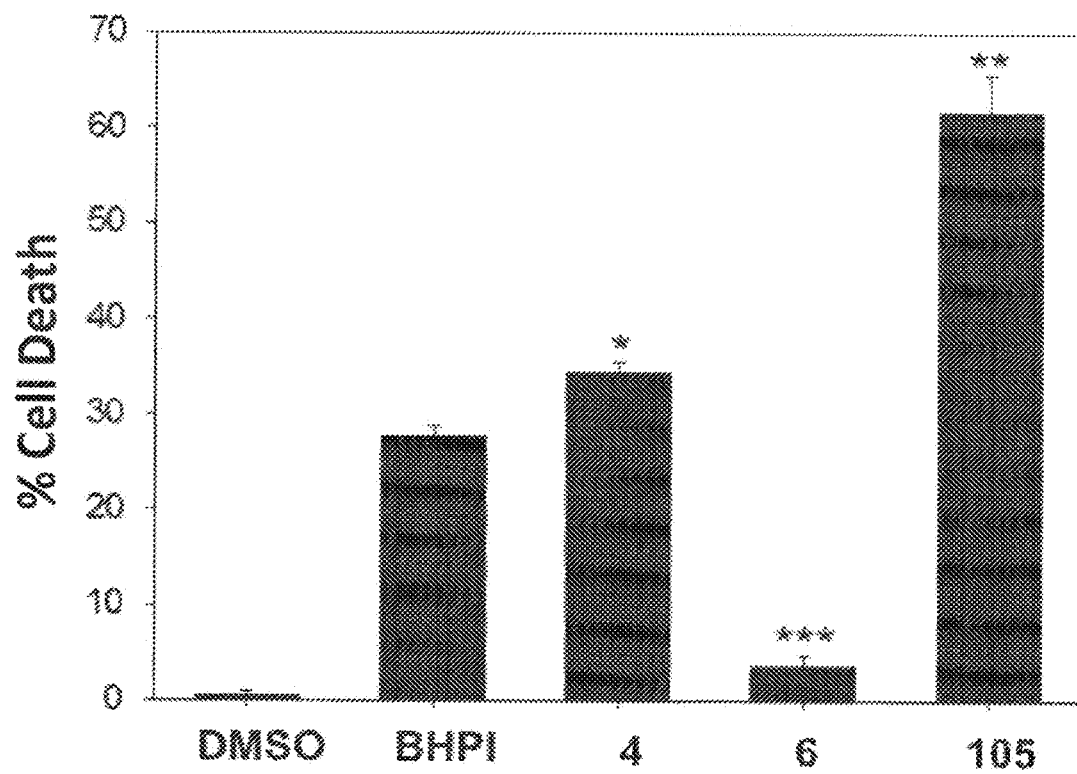
FIG. 26. Comparison of the ability of test compounds 4, 6, 105 and BHPI to kill TYS cells.

FIG. 26 shows a comparison of the ability of test compounds 4, 6, 105 and BHPI to kill TYS cells. TYS cells were incubated for 24 hours with 50 nM of of BHPI or 50 nM of each of the indicated test compounds: 4, 6 and 105. Cell death was determined using the instrument-based Trypan Blue exclusion assay. (n=3±SEM). Thus, compared to BHPI, compounds 4 and 105 exhibit increased ability to kill the TYS cells.

Figure 27:
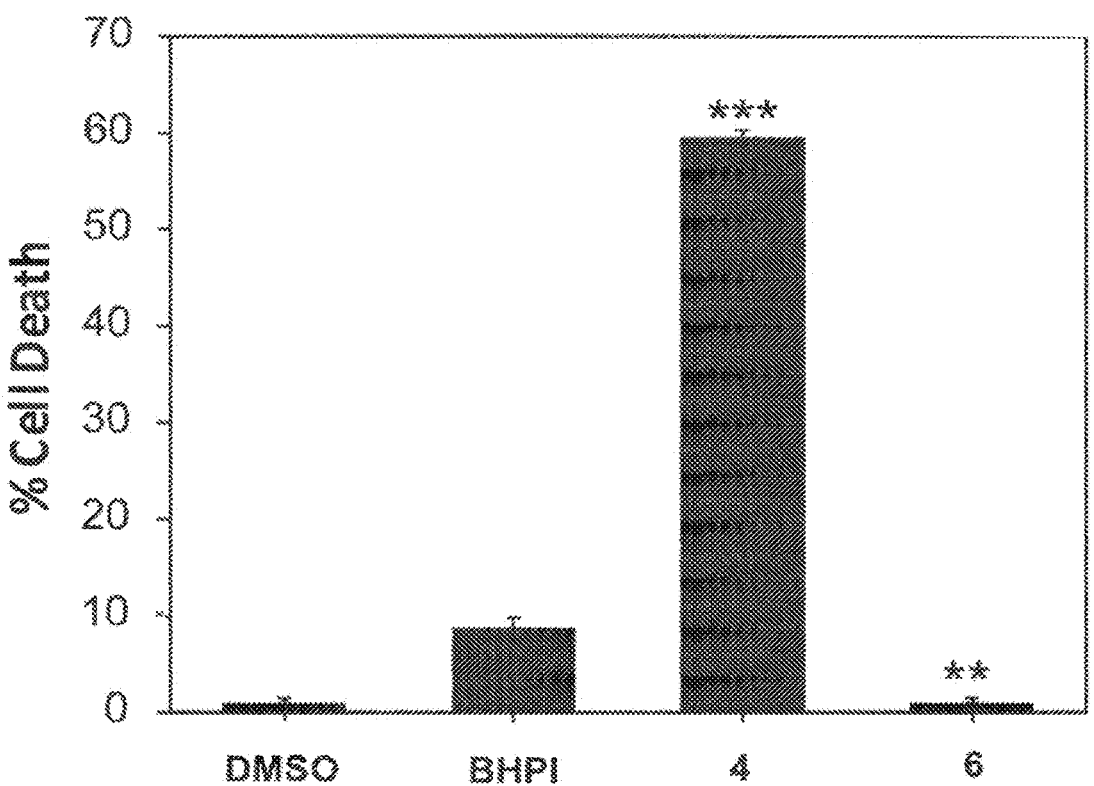
FIG. 27. Comparison of the ability of test compounds and BHPI to kill T47D cells.

FIG. 27 shows a comparison of the ability of test compounds and BHPI to kill T47D cells. T47D cells were incubated for 24 hours with 75 nM of BHPI or 75 nM of each of the indicated test compounds: 4 and 6. Cell death was determined using the instrument-based Trypan Blue exclusion assay. (n=3±SEM). Thus, compound 4 displays a greatly increased ability to kill breast cancer cells containing wild type estrogen receptor.

Figure 28:
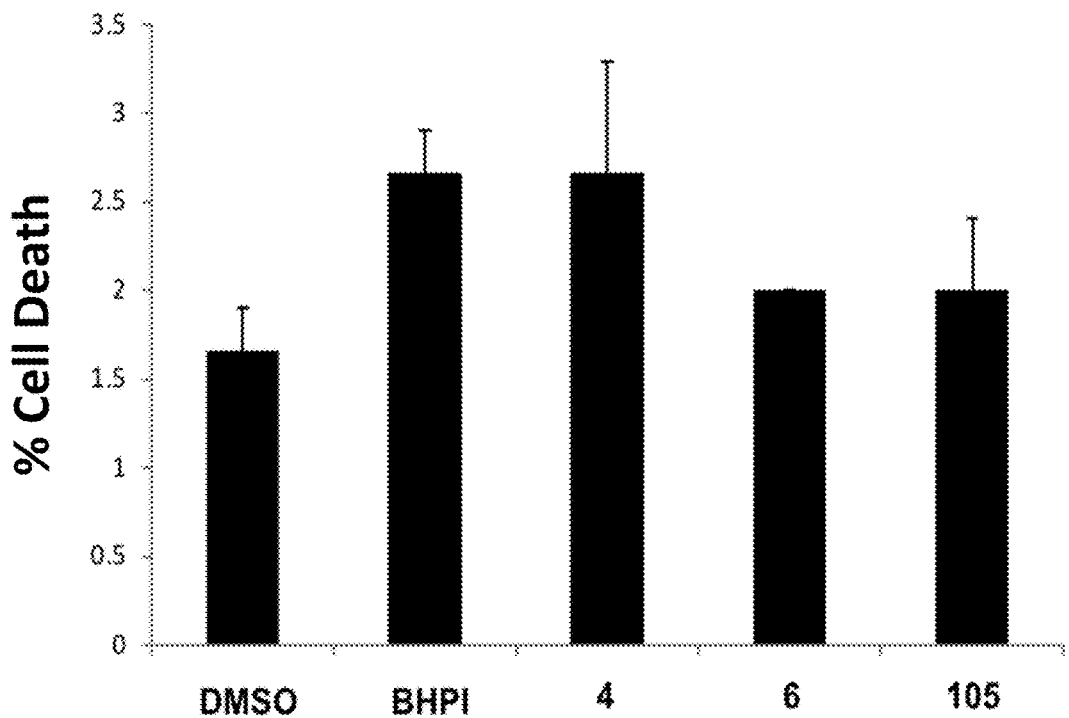
FIG. 28. Neither the test compounds nor BHPI kill ERα negative non-tumorigenic MCF-10A breast cells.

In FIG. 28, neither the test compounds nor BHPI kill non-tumorigenic ERα Negative MCF-10A breast cells. ERα Negative MCF-10A cells were maintained for 24 hours in DMSO vehicle or 75 nM of BHPI or 75 nM of each of the indicated test compounds: 4, 6 and 105. Cell death was determined using the instrument-based Trypan Blue exclusion assay. (n=3±SEM). Thus, at 75 nM, neither BHPI nor any of the test compounds induce significant death of the ERα Negative MCF-10A cells.

Figure 29:
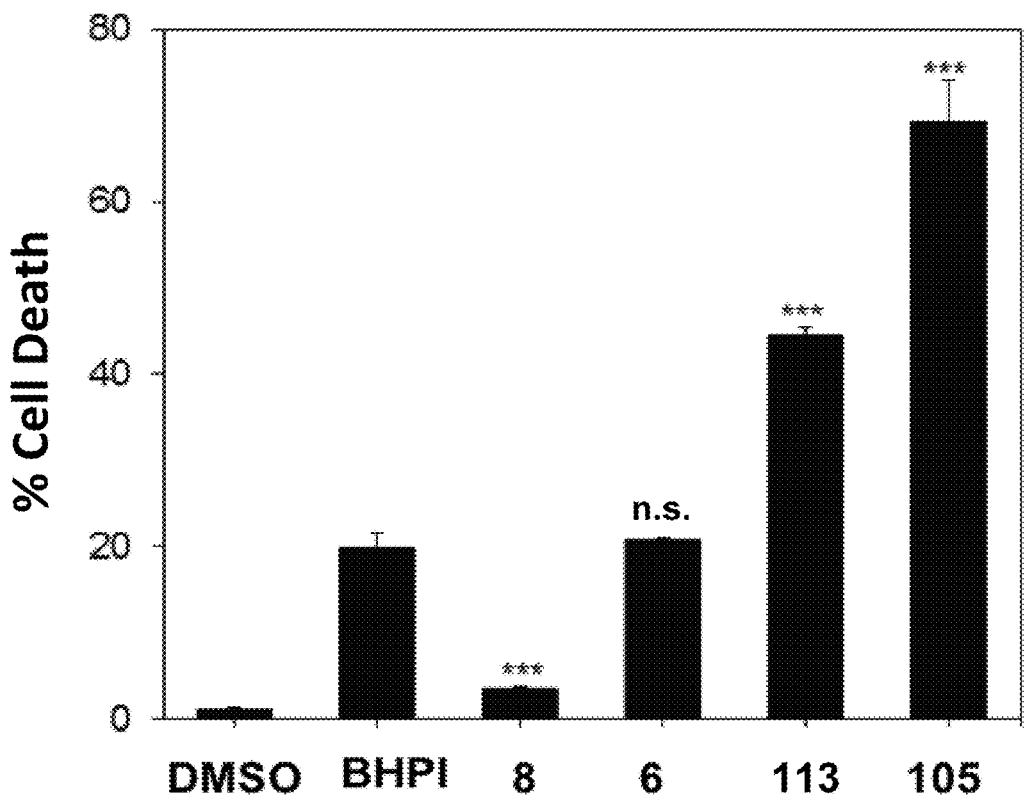
FIG. 29. Evaluation of the ability of test compounds and BHPI to kill T47D cells.

FIG. 29 shows the evaluation of the ability of test compounds and BHPI to kill T47D cells. T47D cells were treated for 24 hours with 100 nM BHPI, or with 100 nM of each of the test compounds: 6, 8, and 105. (n.s. not significant). Cell death was determined using the instrument-based Trypan Blue exclusion assay. (n=3±SEM). Thus, compared to BHPI, compound 105 displays increased ability to kill T47D cells.

Figure 30:
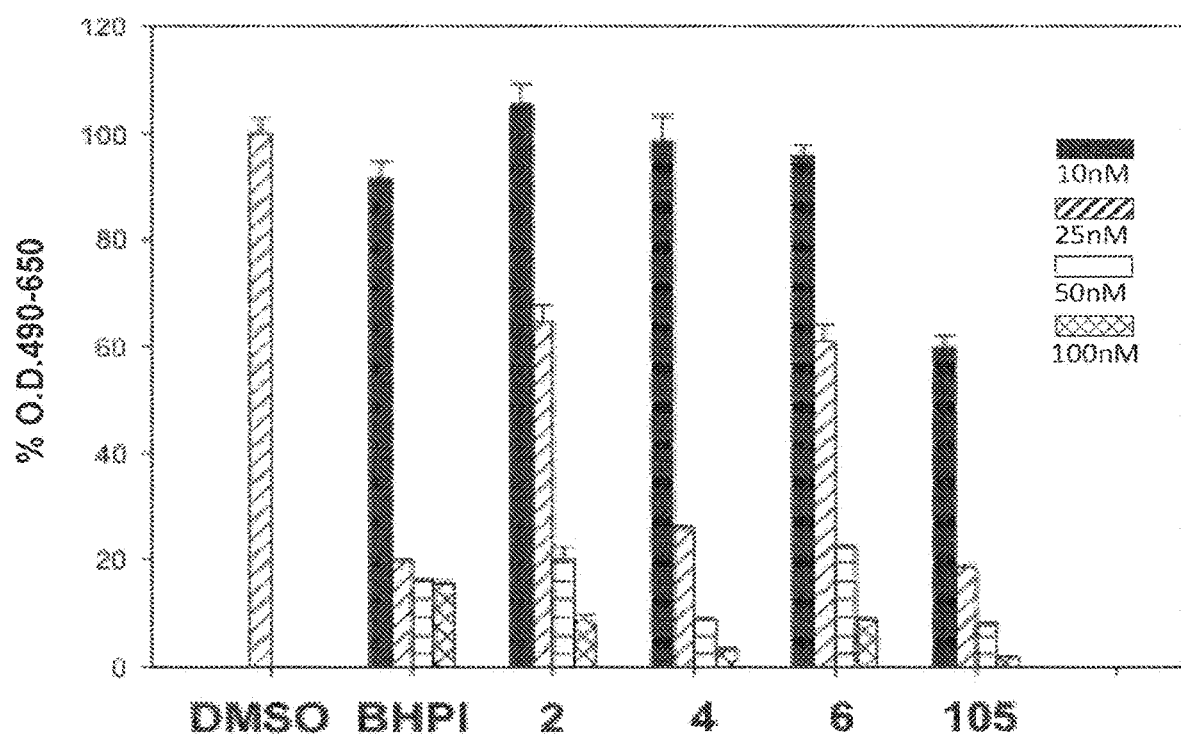
FIG. 30. Dose-response studies comparing the ability of BHPI and test compounds to inhibit proliferation of T47D, TYS and TDG cells.
Figure 31:
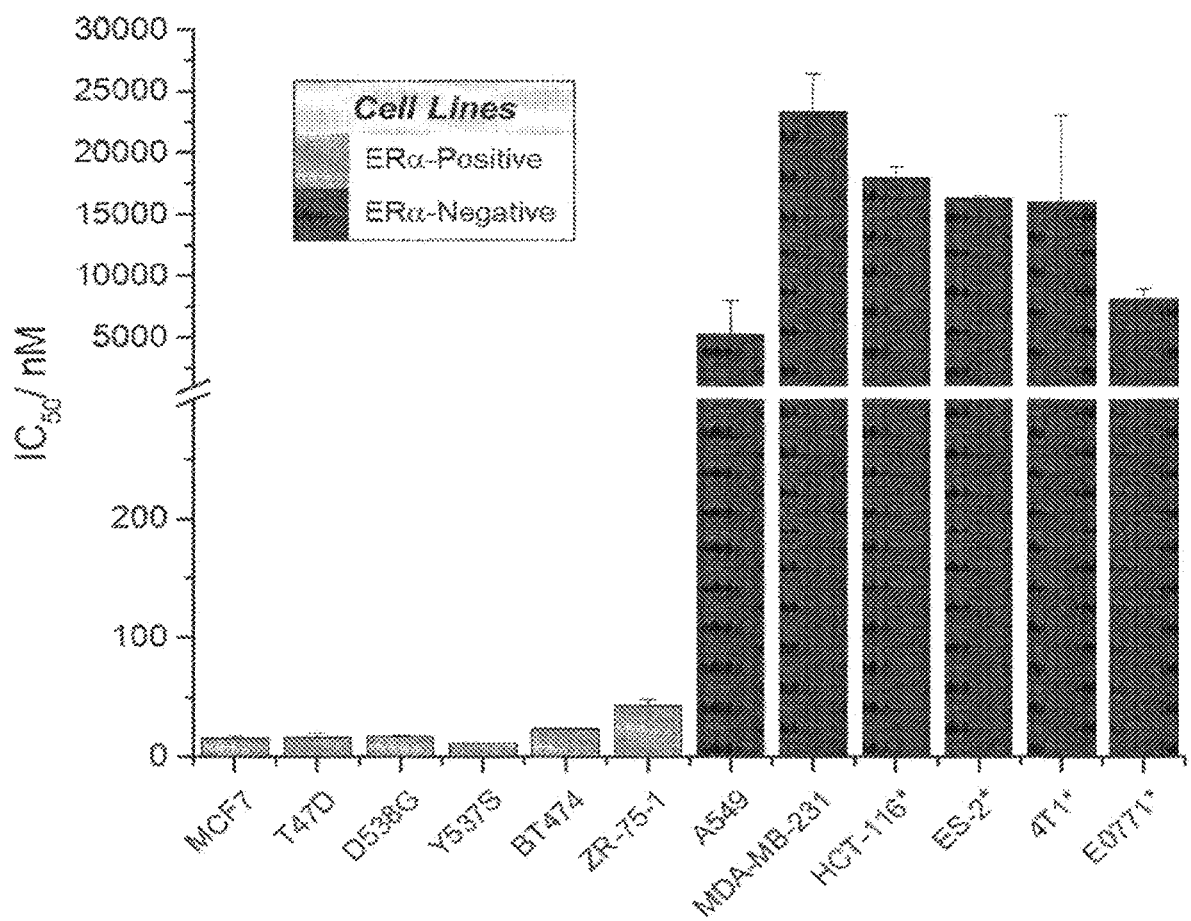
FIG. 31. (−)105 is highly selective for ER+ cancer cells, including vs the deadly ER+ mutants.

FIG. 30 compares the ability of BHPI and test compounds to inhibit proliferation of T47D, TYS and TDG cells. T47D cells were in medium containing 10 FBS (which contains estrogen), TYS-4 and TDG-1 cells were in medium containing 10% cd-FBS (estrogen depleted). Cells are plated at 2,000 cells/well in 96 well plates. After 24 hours in medium containing FBS or charcoal-dextran treated FBS (depleted of endogenous estrogens), the indicated concentration of each compound (in DMSO at $\frac{1}{1000}^{th}$ of the volume of medium) was added. After 2 days the medium was changed, and the compounds were added again. After 2 additional days (4 days total) MTS assays are used to evaluate cell proliferation. (n=6±S.E.M.). Thus, BHPI and the new compounds effectively inhibit proliferation of the T47D, TYS-4 and TDG-1 cell. The data suggests that compounds 2, 4, 6 and 105 are more effective than BHPI in killing these ERα positive breast cancer cells.

Additional data are shown in FIG. 31 and FIGS. 33-43. Through a medicinal chemistry campaign, (±)-1 was discovered to show an unexpected cytotoxic phenotype (FIG. 36A). All known targeted therapies for estrogen receptor alpha (ERα) are cytostatic, meaning they only prevent cell growth and do not kill cancer cells. Preparative chiral column chromatography provided access to enantiomerically pure material (Example 4) identified by polarimetry as (−)-105 and (+)-105. Chemical derivatization and x-ray crystallography further characterized the active enantiomer having the (R)-configuration and the inactive enantiomer having the (S)-configuration (Scheme 5). Biological data (FIG. 36B and Example 4) demonstrate that (R)-1 is cytotoxic to ERα positive cells (MCF-7) with minimal effects seen in ERα negative cells (MDA-MB-231). Therefore, the compound was renamed as SERK-F6 for Selective Estrogen Receptor Killer with this version having six fluorines). The dose dependent activity of SERK-F6 was determined against a panel of cancer cell lines (FIG. 36C and FIG. 37A) for ERα.

An important aspect for cytotoxic therapy is the ability to quantitatively kill a cell population. SERK-F6 quantitatively kills ERα cell lines in a rapid 24-hour crystal violet assay (FIG. 36D) and in long-term cell culturing experiments (FIGS. 36E-F and FIG. 37B). SERK-F6 kills via anticipatory unfolded protein response (UPR) activation (FIG. 38). Important markers of this mechanism are the increased levels of spliced XBP1 (sp-XBP1) (FIG. 38A), rapid decreased in cellular ATP levels (FIG. 38B), and rapid inhibition of protein synthesis (FIG. 38C).

The pharmacokinetics of SERK-F6 was measured in mice (FIG. 40A-B). Additional studies showed that SERK-F6 was blood-brain barrier penetrant (FIG. 40C-D). Also, long-term treatment of SERK-F6 does not ablate ERα tissues as measured by circulating estradiol levels (FIG. 40E). These data demonstrate that SERK-F6 can achieve biologically relevant concentrations in-vivo and be well-tolerated.

To probe the efficacy of SERK-F6 for killing ERα positive tumors, large MCF-7 tumors were grown and then intervened with therapy. SERK-F6 treatment results in dramatic tumor regressions (FIG. 39A and FIG. 40F-G). Because current therapy (i.e. fulvestrant, Fulv.) is cytostatic, dramatic effects against these large and established tumors are not obtained. Additionally, daily SERK-F6 treatment did not lead to any change in murine weight during the study, demonstrating the tolerance of SERK-F6 in-vivo (FIG. 40H).

Furthermore, to demonstrate in-vivo mechanism of action of SERK-F6, MCF-7 tumors were grafted in mice and then treated with SERK-F6. The mice were then sacrificed prior to complete tumor eradication. This data showed activation of the UPR with increases in P-PERK and P-eiF2alpha levels (FIGS. 39B-E and FIGS. 40I-J).

Because ERα mutations leading to constitutive activation and therapy resistance represent a clinical challenge, it was demonstrated that SERK-F6 can also address these resistant tumors. Thus, SERK-F6 eradicates Y537S tumors (i.e. TYS cell line) in a dose-dependent manner and in multiple dosing administrations (i.e., i.p. and oral administration) and was also tolerated (FIGS. 41A-D and FIGS. 42B-C). Upon treatment cessation, tumors did not regrow, indicating complete tumor eradications (FIG. 42A). With a lower subtherapeutic dose of SERK-F6 (i.e. 10 mg/kg oral), tumors did regrow but retreatment of these tumors with higher doses of SERK-F6 demonstrated that these regrown tumors are still sensitive to SERK-F6 and are not resistant (FIG. 42D). This result shows the importance of complete cell killing for eradicating cancers. SERK-F6 treatment also leads to destruction of D538G mutant tumors (TDG cell line) (FIGS. 41D-E). SERK-F6 treatment was again tolerated (FIG. 42E) at higher doses and enough to eradicate tumors (FIG. 42F). While lower doses do not completely eradicate tumors, retreatment of these tumors with higher doses of SERK-F6 regresses the tumors (FIGS. 42G-H).

To confirm that tumor regressions are not just seen with T47D background cell lines (TYS and TDG), MCF-7 cells were treated with Y537S or D538G mutations in their ERα proteins (MYS and MDG cells, respectively) with SERK-F6. Dramatic tumor regressions were observed (FIGS. 41F-G, and FIGS. 43A-D). Again, higher doses are necessary for complete tumor responses, while lower doses lead to non-resistant tumor growth (FIG. 43 B-D). SERK-F6 treatment also eradicates metastatic tumor burden (FIG. 41I).

Example 4. Determination of Absolute Configuration and IC50s of Enantiomers of Compound 1 (105)

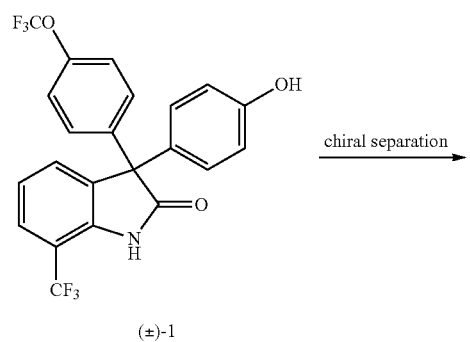 [SMILES: O=C1Nc2c(C(F)(F)F)cccc2C1(c1ccc(O)cc1)c1ccc(OC(F)(F)F)cc1]

(±)-1 chiral separation

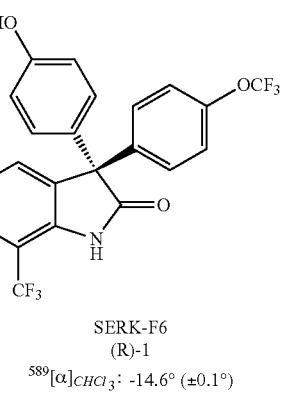

SERK-F6
(R)-1
$^{589}[\alpha]_{CHCl_3}$: −14.6° (±0.1°)

(S)-1
$^{589}[\alpha]_{CHCl_3}$: +13.8° (±0.1°)

| Species | IC$_{50}$ (nM) | S.E.M. |
|---|---|---|
| (±)-1 | 42.6 | 1.9 |
| (R)-1 | 20.3 | 0.9 |
| (S)-1 | >1000 | — |

Preparative gram-scale chiral separation of (±)-1 yields enantiopure (R)-1 and (S)-1 with opposite optical rotations (Scheme 5). IC$_{50}$ values of (±)-1, (R)-1, and (S)-1 against MCF-7 cells reveals (R)-1 is the active species, referred to as SERK-F6. Values were obtained after 24-hour incubation utilizing Alamar blue fluorescence assay normalized to live and death controls (vehicle and raptinal treated). (S)-1 IC$_{50}$ is >1 µM. Error shown as S.E.M.

Scheme 5. Synthetic sequence to access crystallizable (R)-1 and (S)-1 derivatives: X-ray determination of structures of (R)-2 and (S)-2.

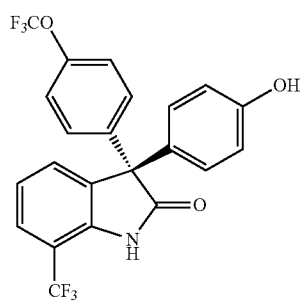

n-BuLi
THF,
-78° C. to r.t.,
1 h
then

TfOH
CH$_2$Cl$_2$, r.t.
1 h

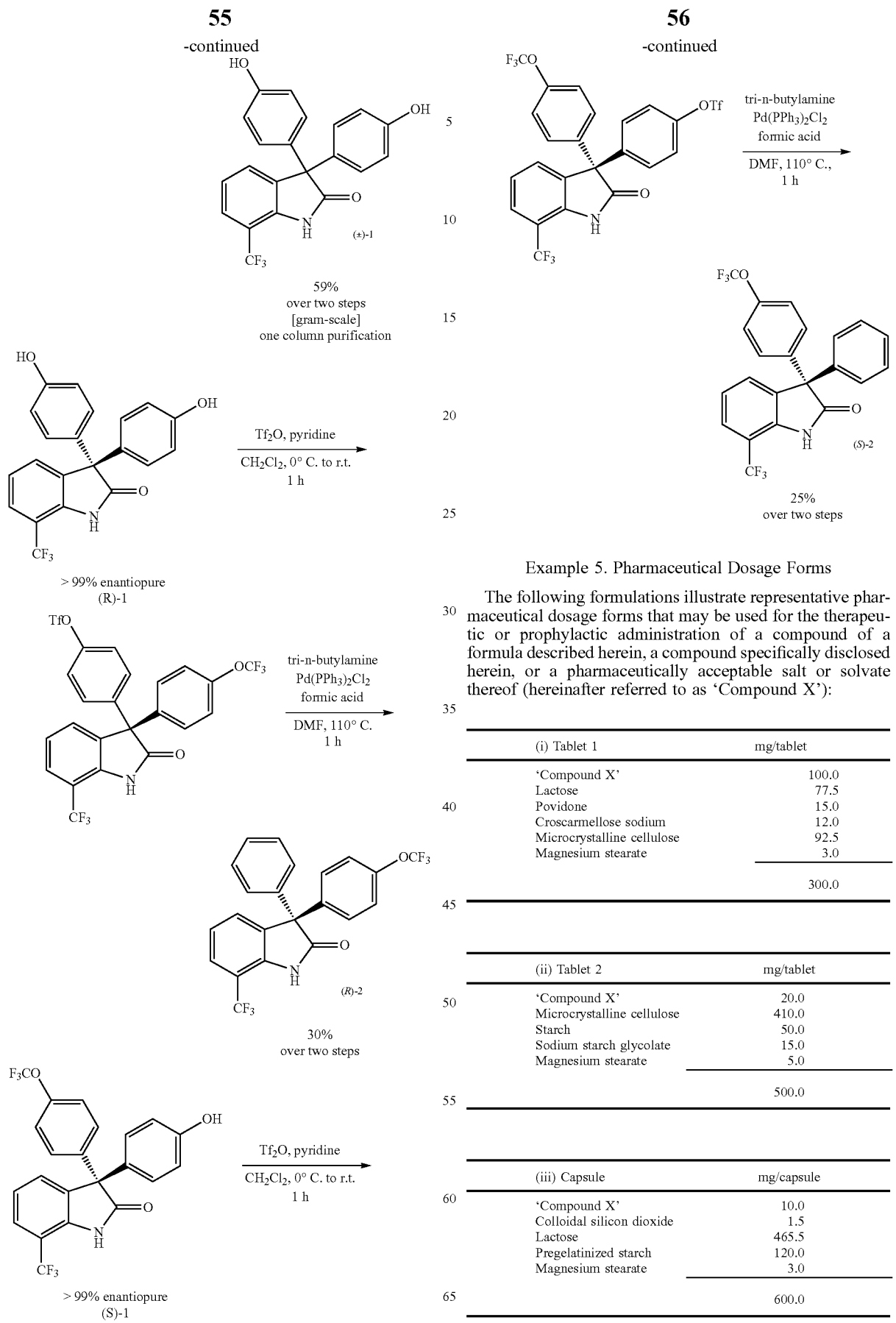

Example 5. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of treating a cancer comprising administering to an ERα positive cancer subject in need thereof a therapeutically effective amount of a compound of Formula (I):

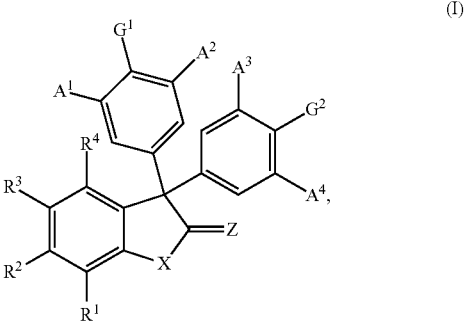

or a salt or solvate thereof,
wherein
$R^1$, $R^2$, $R^3$ and $R^4$ are each independently H, halo, —$OR^A$, —$SR^A$, —$N(R^A)_2$, alkyl, cycloalkyl, heterocyclyl, aryl, or heteroaryl;
$A^1$, $A^2$, $A^3$ and $A^4$ are each independently H, halo, or alkyl;
$G^1$ is halo, —$OR^B$, —$SR^B$, —$S(=O)_2R^B$, or alkyl;

$G^2$ is halo, $-OR^C$, $-SR^C$, $-S(=O)_2R^C$, or alkyl;
X and Z are each independently O, S, or $-NR^D$; and
$R^A$, $R^B$, $R^C$ and $R^D$ are each independently H or alkyl,
wherein, when present, $-OR^B$ and $-OR^C$ are not both $-OH$;
wherein each alkyl, cycloalkyl, heterocyclyl, aryl, and heteroaryl is optionally substituted with one or more substituents,
thereby treating the cancer in the subject.

2. The method of claim 1 wherein the compound kills or inhibits growth of ERa positive cancer by hyperactivation of the unfolded protein response (UPR) in the endoplasmic reticulum.

3. The method of claim 1 wherein the compound is a racemic mixture of (R)-105 and (S)-105:

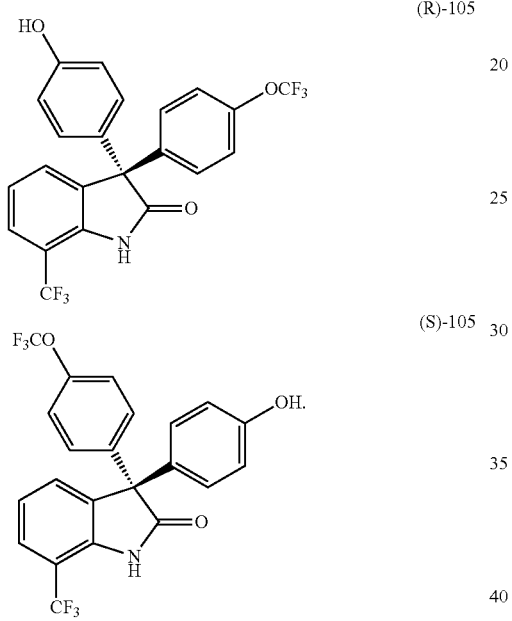

4. The method of claim 1 wherein the ERa positive cancer is a breast cancer, ovarian cancer, uterine cancer, cervical carcinoma, or endometrial cancer.

5. The method of claim 1 wherein the compound is administered orally or by injection.

6. The method of claim 1 wherein $R^1$ is $-(C_1-C_6)$alkyl substituted with one to three halo groups.

7. The method of claim 6 wherein $R^1$ is $CF_3$.

8. The method of claim 7 wherein $R^2$, $R^3$, $R^4$, $A^1$, $A^2$, $A^3$, and $A^4$ are H.

9. The method of claim 8 wherein X is $-NR^D$ wherein $R^D$ is H, and Z is O.

10. The method of claim 9 wherein $G^1$ is $-OR^B$ wherein $R^B$ is $CF_3$.

11. The method of claim 10 wherein $G^2$ is $-OR^C$ wherein $R^C$ is H.

12. The method of claim 11 wherein the ERα positive cancer is a breast cancer, ovarian cancer, uterine cancer, cervical carcinoma, or endometrial cancer.

13. The method of claim 6 wherein $R^1$ is $CF_3$ or $CH_3$; $R^2$, $R^3$, and $R^4$ are H; $A^1$, $A^2$, $A^3$, and $A^4$ are H; X is $-NH$; Z is O; $G^1$ is $-OCF_3$; and $G^2$ is $-OH$.

14. The method of claim 13 wherein the ERα positive cancer is a breast cancer, ovarian cancer, uterine cancer, cervical carcinoma, or endometrial cancer.

15. The method of claim 1 wherein administering the compound of Formula (I) comprises administering a composition comprising the compound of Formula (I) in combination with a pharmaceutically acceptable diluent, carrier, excipient, or buffer.

16. The method of claim 15 wherein the composition comprises the compound (R)-105:

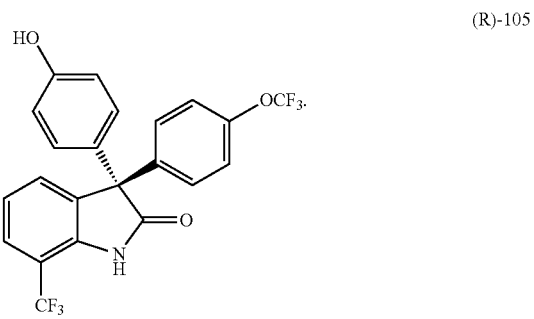 [SMILES: O=C1Nc2c(C(F)(F)F)cccc2[C@@]1(c1ccc(O)cc1)c1ccc(OC(F)(F)F)cc1]

17. The method of claim 16 wherein the ERα positive cancer is a breast cancer, ovarian cancer, uterine cancer, cervical carcinoma, or endometrial cancer.

18. The method of claim 15 wherein the composition comprises the compound (S)-105:

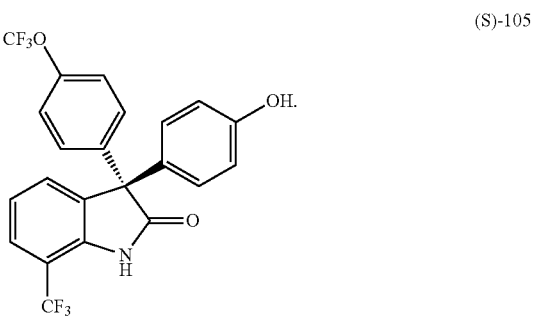

19. The method of claim 18 wherein the ERα positive cancer is a breast cancer, ovarian cancer, uterine cancer, cervical carcinoma, or endometrial cancer.

20. A method of treating a cancer comprising administering to an ERα positive cancer subject in need thereof a therapeutically effective amount of the compound (R)-105 or (S)-105:

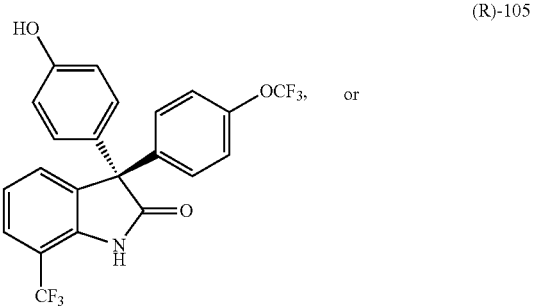

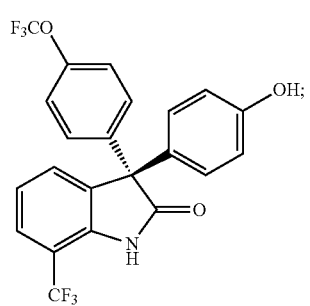 (S)-105
wherein the ERα positive cancer is a breast cancer, ovarian cancer, uterine cancer, cervical carcinoma, or endometrial cancer, thereby treating the cancer in the subject.
* * * * *